(12) United States Patent
Kiani et al.

(10) Patent No.: US 12,275,957 B2
(45) Date of Patent: Apr. 15, 2025

(54) NEXT GENERATION DESIGNER LIVER ORGANOIDS AND THEIR METHODS OF PREPARATION AND USE

(71) Applicants: ARIZONA BOARD OF REGENTS ON BEHALF OF ARIZONA STATE UNIVERSITY, Scottsdale, AZ (US); The Johns Hopkins University, Baltimore, MD (US)

(72) Inventors: Samira Kiani, Scottsdale, AZ (US); Mo R Ebrahimkhani, Scottsdale, AZ (US); Jeremy Velazquez, Pittsburgh, PA (US); Ryan LeGraw, Pittsburgh, PA (US); Patrick Cahan, Baltimore, MD (US)

(73) Assignees: ARIZONA BOARD OF REGENTS ON BEHALF OF ARIZONA STATE UNIVERSITY, Scottsdale, AZ (US); The Johns Hopkins University, Baltimore, MD (US)

( * ) Notice: Subject to any disclaimer, the term of this patent is extended or adjusted under 35 U.S.C. 154(b) by 707 days.

(21) Appl. No.: 16/973,421

(22) PCT Filed: Jun. 10, 2019

(86) PCT No.: PCT/US2019/036410
§ 371 (c)(1),
(2) Date: Dec. 8, 2020

(87) PCT Pub. No.: WO2019/237124
PCT Pub. Date: Dec. 12, 2019

(65) Prior Publication Data
US 2021/0254012 A1    Aug. 19, 2021

Related U.S. Application Data

(60) Provisional application No. 62/775,505, filed on Dec. 5, 2018, provisional application No. 62/682,916, filed on Jun. 9, 2018.

(51) Int. Cl.
| | |
|---|---|
| *C12N 5/071* | (2010.01) |
| *A61K 35/407* | (2015.01) |
| *C12N 15/113* | (2010.01) |
| *C12N 15/86* | (2006.01) |
| *C12N 15/90* | (2006.01) |
| *G01N 33/50* | (2006.01) |

(52) U.S. Cl.
CPC .......... *C12N 5/0671* (2013.01); *A61K 35/407* (2013.01); *C12N 15/86* (2013.01); *C12N 15/907* (2013.01); *G01N 33/5014* (2013.01); *G01N 33/5067* (2013.01); *G01N 33/5088* (2013.01); *C12N 2310/20* (2017.05); *C12N 2501/15* (2013.01); *C12N 2501/727* (2013.01); *C12N 2506/45* (2013.01); *C12N 2740/15043* (2013.01); *C12N 2800/80* (2013.01)

(58) Field of Classification Search
CPC .............. C12N 5/0671; C12N 2310/20; C12N 2506/45; C12N 2310/16; A61K 35/407
See application file for complete search history.

(56) References Cited

U.S. PATENT DOCUMENTS

| | | |
|---|---|---|
| 2,045,926 A | 6/1936 | Reutter |
| 2017/0218333 A1 | 8/2017 | Deng et al. |
| 2018/0066233 A1 | 3/2018 | Ortega et al. |

FOREIGN PATENT DOCUMENTS

| | | |
|---|---|---|
| CN | 107964534 | 4/2018 |
| WO | 2016176690 A2 | 11/2016 |
| WO | 2018026723 A1 | 2/2018 |
| WO | 2018085615 | 5/2018 |
| WO | 2019237124 A1 | 12/2019 |

OTHER PUBLICATIONS

Takayama et al (Enrichment of high-functioning human iPS cell-derived hepatocyte-like cells for pharmaceutical research. Biomaterials, vol. 161, Jan. 2018) (Year: 2018).*
Guye et al (Genetically engineering self-organization of human pluripotent stem cells into a liver bud-like tissue using Gata6. Nature Communications, vol. 7, Jan. 2016), (Year: 2016).*
Nakamori et al (Hepatic maturation of human iPS cell-derived hepatocyte-like cells by ATF5, c/EBPa, and PROX1 transduction. Biochemical and Biophysical Research Communications, vol. 469, Dec. 2015) (Year: 2015).*
Han et al (Enhanced intrinsic CYP3A4 activity in human hepatic C3A cells with optically controlled CRISPR/dCas9 activator complex. Integr. Biol., vol. 10, 2018). (Year: 2018).*
Addgene Protocols-Infecting Target cell, pLKO.1 protocol, Published Dec. 2006. (Year: 2006).*
Kramer et al (In Vitro and in Vivo Comparative Study of Chimeric Liver-Specific Promoters. Molecular Therapy vol. 7, No. 3, Mar. 2003). (Year: 2003).*
Leite et al (Novel human hepatic organoid model enables testing of drug-induced liver fibrosis in vitro. Biomaterials, 2016) (Year: 2016).*
Hoffman (Hepatic stellate cell hypertrophy is associated with metabolic liver fibrosis. Sci Rep, 2020) (Year: 2020).*
CYP3A4 gene locus (Year: 2023).*
Schneider, A short history of guide RNAs. EMBO reports, vol. 21, 2020 (Year: 2020).*

(Continued)

*Primary Examiner* — Emily A Cordas
*Assistant Examiner* — Matasha Dhar
(74) *Attorney, Agent, or Firm* — Quarles & Brady, LLP

(57) ABSTRACT

The present disclosure relates to synthetic liver organoids and methods of using such synthetic liver organoids for various applications including drug discovery and modeling human liver development. In particular, provided herein are methods of producing and using synthetic mature liver organoids comprising mature, functional cells found in the human liver.

15 Claims, 29 Drawing Sheets
(20 of 29 Drawing Sheet(s) Filed in Color)
Specification includes a Sequence Listing.

(56) References Cited

OTHER PUBLICATIONS

Liu et al (CRISPR-ERA: a comprehensive design tool for CRISPR-mediated gene editing, repression and activation. Bioinformatics, 31(22), 2015, 3676-3678) (Year: 2015).*
List of CYP3A4 sgRNAs for gene activation generated by CRISPR-ERA (Year: 2015).*
Roost, M.S., van Iperen, L., Ariyurek, Y., Buermans, H.P., Arindrarto, W., Devalla, H.D., Passier, R., Mummery, C.L., Carlotti, F., de Koning, E.J., et al. (2015). KeyGenes, a Tool to Probe Tissue Differentiation Using a Human Fetal Transcriptional Atlas. Stem Cell Reports 4, 1112-1124.
Sarma, J.V., and Ward, P.A. (2011). The complement system. Cell Tissue Res 343, 227-235.
Satija, R., Farrell, J.A., Gennert, D., Schier, A.F., and Regev, A. (2015). Spatial reconstruction of single-cell gene expression data. Nat Biotechnol 33, 495-502.
Sawitza, I., Kordes, C., Gotze, S., Herebian, D., and Haussinger, D. (2015). Bile acids induce hepatic differentiation of mesenchymal stem cells. Sci Rep 5, 13320.
Schwank et al., "Functional Repair of CFTR by CRISPR/Cas9 in Intestinal Stem Cell Organoids of Cystic Fibrosis Patients", Cell Stem Cell 13, 653-658 (2013).
Seth, A., Ye, J., Yu, N., Guez, F., Bedford, D.C., Neale, G.A., Cordi, S., Brindle, P.K., Lemaigre, F.P., Kaestner, K.H., et al. (2014). Prox1 ablation in hepatic progenitors causes defective hepatocyte specification and increases biliary cell commitment. Development 141, 538-547.
Shen, L., Shao, N., Liu, X., and Nestler, E. (2014). ngs.plot: Quick mining and visualization of next-generation sequencing data by integrating genomic databases. BMC Genomics 15, 284.
Si-Tayeb, K., Lemaigre, F.P., and Duncan, S.A. (2010a). Organogenesis and development of the liver. Dev Cell 18, 175-189.
Si-Tayeb, K., Noto, F.K., Nagaoka, M., Li, J., Battle, M.A., Duris, C., North, P.E., Dalton, S., and Duncan, S.A. (2010b). Highly efficient generation of human hepatocyte-like cells from induced pluripotent stem cells. Hepatology 51, 297-305.
Takayama et al., "Enrichment of high-functioning human iPS cell-derive hepatocyte-like cells for pharmaceutical research", Biomaterials 161 (2018) 24-32.
Takebe, T., Sekine, K., Enomura, M., Koike, H., Kimura, M., Ogaeri, T., Zhang, R.R., Ueno, Y., Zheng, Y.W., Koike, N., et al. (2013). Vascularized and functional human liver from an iPSC-derived organ bud transplant. Nature 499, 481-484.
Trapnell, C., Pachter, L., and Salzberg, S.L. (2009). TopHat: discovering splice junctions with RNA-Seq. Bioinformatics 25, 1105-1111.
Vogel, A., van Den Berg, I.E., Al-Dhalimy, M., Groopman, J., Ou, C.N., Ryabinina, O., Iordanov, M.S., Finegold, M., and Grompe, M. (2004). Chronic liver disease in murine hereditary tyrosinemia type 1 induces resistance to cell death. Hepatology 39, 433-443.
Wang, W., Du, Z., Yan, J., Ma, D., Shi, M., Zhang, M., Peng, C., and Li, H. (2014). Mesenchymal stem cells promote liver regeneration and prolong survival in small-for-size liver grafts: involvement of C-Jun N-terminal kinase, cyclin D1, and NF-kappaB. PLoS One 9, e112532.
Wilson, E.M., Bial, J., Tarlow, B., Bial, G., Jensen, B., Greiner, D.L., Brehm, M.A., and Grompe, M. (2014). Extensive double humanization of both liver and hematopoiesis in FRGN mice. Stem Cell Res 13, 404-412.
Wobus, A.M., and Loser, P. (2011). Present state and future perspectives of using pluripotent stem cells in toxicology research. Arch Toxicol 85, 79-117.
Zanger, U.M., and Schwab, M. (2013). Cytochrome P450 enzymes in drug metabolism: regulation of gene expression, enzyme activities, and impact of genetic variation. Pharmacol Ther 138, 103-141.
Zhang, Y., Liu, T., Meyer, C.A., Eeckhoute, J., Johnson, D.S., Bernstein, B.E., Nusbaum, C., Myers, R.M., Brown, M., Li, W., et al. (2008). Model-based analysis of ChIP-Seq (MACS). Genome Biol 9, R137.
Zhao et al., "Establishment and Dysfunction of the Blood-Brain Barrier", Cell 163, (2015).
Zheng, G.X., Terry, J.M., Belgrader, P., Ryvkin, P., Bent, Z.W., Wilson, R., Ziraldo, S.B., Wheeler, T.D., McDermott, G. P., Zhu, J., et al. (2017). Massively parallel digital transcriptional profiling of single cells. Nat Commun 8, 14049.
Zhu, S., Rezvani, M., Harbell, J., Mattis, A.N., Wolfe, A.R., Benet, L.Z., Willenbring, H., and Ding, S. (2014). Mouse liver repopulation with hepatocytes generated from human fibroblasts. Nature 508, 93-97.
Akbari, S., Sevinc, G.G., Ersoy, N., Basak, O., Kaplan, K., Sevinc, K., Ozel, E., Sengun, B., Enustun, E., Ozcimen, B., et al. (2019). Robust, Long-Term Culture of Endoderm-Derived Hepatic Organoids for Disease Modeling. Stem Cell Reports 13, 627-641.
Asai, A., Aihara, E., Watson, C., Mourya, R., Mizuochi, T., Shivakumar, P., Phelan, K., Mayhew, C., Helmrath, M., Takebe, T., et al. (2017). Paracrine signals regulate human liver organoid maturation from induced pluripotent stem cells. Development 144, 1056-1064.
Bijsmans et al., "Characterization of stem cell-derived liver and intestinal organoids as a model system to study nuclear receptor biology", Biochimica et Biophysica Acta 1863 (2017) 687-700.
Bodin, K., Lindbom, U., and Diczfalusy, U. (2005). Novel pathways of bile acid metabolism involving CYP3A4. Biochim Biophys Acta 1687, 84-93.
Bolger, A.M., Lohse, M., and Usadel, B. (2014). Trimmomatic: a flexible trimmer for Illumina sequence data. Bioinformatics 30, 2114-2120.
Bolouri, H., and Davidson, E.H. (2002). Modeling transcriptional regulatory networks. Bioessays 24, 1118-1129.
Butler, A., Hoffman, P., Smibert, P., Papalexi, E., and Satija, R. (2018). Integrating single-cell transcriptomic data across different conditions, technologies, and species. Nat Biotechnol 36, 411-420.
Cahan, P., Li, H., Morris, S.A., Lummertz da Rocha, E., Daley, G.Q., and Collins, J.J. (2014). CellNet: network biology applied to stem cell engineering. Cell 158, 903-915.
Cakir, B., Xiang, Y., Tanaka, Y., Kural, M.H., Parent, M., Kang, Y.J., Chapeton, K., Patterson, B., Yuan, Y., He, C.S., et al. (2019). Engineering of human brain organoids with a functional vascular-like system. Nat Methods 16, 1169-1175.
Chavez et al., "Highly efficient Cas9-mediated transcriptional programming", Nature Methods, vol. 12, No. 4 (2015).
Chen, E.Y., Tan, C.M., Kou, Y., Duan, Q., Wang, Z., Meirelles, G.V., Clark, N.R., and Ma'ayan, A. (2013). Enrichr: interactive and collaborative HTML5 gene list enrichment analysis tool. BMC Bioinformatics 14, 128.
Coll, M., Perea, L., Boon, R., Leite, S.B., Vallverdu, J., Mannaerts, I., Smout, A., El Taghdouini, A., Blaya, D., Rodrigo-Torres, D., et al. (2018). Generation of Hepatic Stellate Cells from Human Pluripotent Stem Cells Enables In Vitro Modeling of Liver Fibrosis. Cell Stem Cell 23, 101-113 e107.
Davidson, M.D., Ware, B.R., and Khetani, S.R. (2015). Stem cell-derived liver cells for drug testing and disease modeling. Discov Med 19, 349-358.
De Franco, E., Shaw-Smith, C., Flanagan, S.E., Shepherd, M.H., International, N.D.M.C., Hattersley, A. T., and Ellard, S. (2013). GATA6 mutations cause a broad phenotypic spectrum of diabetes from pancreatic agenesis to adult-onset diabetes without exocrine insufficiency. Diabetes 62, 993-997.
Driehuis et al., "Stem Cells, Tissue Engineering, Development, and Cancer CRISPR/Cas 9 genome editing and its applications in organoids", Am J Physiol Gastrointest Liver Physiol, 312: G257-G265, 2017.
Du, Y., Wang, J., Jia, J., Song, N., Xiang, C., Xu, J., Hou, Z., Su, X., Liu, B., Jiang, T., et al. (2014). Human hepatocytes with drug metabolic function induced from fibroblasts by lineage reprogramming. Cell Stem Cell 14, 394-403.
Fagerberg, L., Hallstrom, B.M., Oksvold, P., Kampf, C., Djureinovic, D., Odeberg, J., Habuka, M., Tahmasebpoor, S., Danielsson, A., Edlund, K., et al. (2014). Analysis of the human tissue-specific expression by genome-wide integration of transcriptomics and antibody-based proteomics. Mol Cell Proteomics 13, 397-406.
Guye, P., Ebrahimkhani, M.R., Kipniss, N., Velazquez, J.J., Schoenfeld, E., Kiani, S., Griffith, L.G., and Weiss, R. (2016). Genetically

(56) References Cited

OTHER PUBLICATIONS engineering self-organization of human pluripotent stem cells into a liver bud-like tissue using Gata6. Nat Commun 7, 10243.
Han, C.Y. (2018). Update on FXR Biology: Promising Therapeutic Target? Int J Mol Sci 19.
Holt, J.A., Luo, G., Billin, A.N., Bisi, J., McNeill, Y.Y., Kozarsky, K.F., Donahee, M., Wang, D.Y., Mansfield, T.A., Kliewer, S.A., et al. (2003). Definition of a novel growth factor-dependent signal cascade for the suppression of bile acid biosynthesis. Genes Dev 17, 1581-1591.
Horlbeck et al., "Compact and highly active next-generation libraries for CRISPR-mediated gene repression and activation", eLife 2016; 5:e19760. doi: 10.7554/eLife. 19760.
Huang, J., Zhao, X., Wang, J., Cheng, Y., Wu, Q., Wang, B., Zhao, F., Meng, L., Zhang, Y., Jin, M., et al. (2019). Distinct roles of Dlk1 isoforms in bi-potential differentiation of hepatic stem cells. Stem Cell Res Ther 10, 31.
Huch, M., Gehart, H., van Boxtel, R., Hamer, K., Blokzijl, F., Verstegen, M.M., Ellis, E., van Wenum, M., Fuchs, S.A., de Ligt, J., et al. (2015). Long-term culture of genome-stable bipotent stem cells from adult human liver. Cell 160, 299-312.
Inagaki, T., Choi, M., Moschetta, A., Peng, L., Cummins, C.L., McDonald, J.G., Luo, G., Jones, S.A., Goodwin, B., Richardson, J.A., et al. (2005). Fibroblast growth factor 15 functions as an enterohepatic signal to regulate bile acid homeostasis. Cell Metab 2, 217-225.
International Search Report and Written Opinion dated Oct. 2, 2019 for International Application No. PCT/US2019/036410.
Kamiya, A., Kakinuma, S., Onodera, M., Miyajima, A., and Nakauchi, H. (2008). Prospero-related homeobox 1 and liver receptor homolog 1 coordinately regulate long-term proliferation of murine fetal hepatoblasts. Hepatology 48, 252-264.
Kiani et al., "Cas9 gRNA engineering for genome editing, activation and repression", Nature Methods, vol. 12, No. 11 (2015).
Kiani, S., Beal, J., Ebrahimkhani, M.R., Huh, J., Hall, R.N., Xie, Z., Li, Y., and Weiss, R. (2014). CRISPR transcriptional repression devices and layered circuits in mammalian cells. Nat Methods 11, 723-726.
Konermann, S., Brigham, M.D., Trevino, A.E., Joung, J., Abudayyeh, O.O., Barcena, C., Hsu, P.D., Habib, N., Gootenberg, U.S., Nishimasu, H., et al. (2015). Genome-scale transcriptional activation by an engineered CRISPR-Cas9 complex. Nature 517, 583-588.
Kuleshov, M.V., Jones, M.R., Rouillard, A.D., Fernandez, N.F., Duan, Q., Wang, Z., Koplev, S., Jenkins, S.L., Jagodnik, K.M., Lachmann, A., et al. (2016). Enrichr: a comprehensive gene set enrichment analysis web server 2016 update. Nucleic Acids Res 44, W90-97.
Langmead, B., and Salzberg, S.L. (2012). Fast gapped-read alignment with Bowtie 2. Nat Methods 9, 357-359.
Li, B., and Dewey, C.N. (2011). RSEM: accurate transcript quantification from RNA-Seq data with or without a reference genome. BMC Bioinformatics 12, 323.
Li, B., Dorrell, C., Canaday, P.S., Pelz, C., Haft, A., Finegold, M., and Grompe, M. (2017). Adult Mouse Liver Contains Two Distinct Populations of Cholangiocytes. Stem Cell Reports 9, 478-489.
Li, H., and Durbin, R. (2009). Fast and accurate short read alignment with Burrows-Wheeler transform. Bioinformatics 25, 1754-1760.
Li, H., Handsaker, B., Wysoker, A., Fennell, T., Ruan, J., Homer, N., Marth, G., Abecasis, G., Durbin, R., and Genome Project Data Processing, S. (2009). The Sequence Alignment/Map format and SAMtools. Bioinformatics 25, 2078-2079.
Liu, X., Xu, J., Rosenthal, S., Zhang, L.J., McCubbin, R., Meshgin, N., Shang, L., Koyama, Y., Ma, H.Y., Sharma, S., et al. (2020). Identification of Lineage-specific Transcription Factors That Prevent Activation of Hepatic Stellate Cells and Promote Fibrosis Resolution. Gastroenterology.
Love, M.I., Huber, W., and Anders, S. (2014). Moderated estimation of fold change and dispersion for RNA-seq data with DESeq2. Genome Biol 15, 550.
MacParland, S.A., Liu, J.C., Ma, X.Z., Innes, B.T., Bartczak, A.M., Gage, B.K., Manuel, J., Khuu, N., Echeverri, J., Linares, I., et al. (2018). Single cell RNA sequencing of human liver reveals distinct intrahepatic macrophage populations. Nat Commun 9, 4383.
Maeder et al., "CRISPR RNA-guided activation of endogenous human genes", Nature Methods, vol. 10, No. 10 (2013).
Meng et al., "CircRNA: functions and properties of a novel potential biomarker for cancer", Molecular Cancer (2017) 16:94.
Nakamori, D., Takayama, K., Nagamoto, Y., Mitani, S., Sakurai, F., Tachibana, M., and Mizuguchi, H. (2016). Hepatic maturation of human iPS cell-derived hepatocyte-like cells by ATF5, c/EBPalpha, and PROX1 transduction. Biochem Biophys Res Commun 469, 424-429.
Nissim, L., Perli, S.D., Fridkin, A., Perez-Pinera, P., and Lu, T.K. (2014). Multiplexed and programmable regulation of gene networks with an integrated RNA and CRISPR/Cas toolkit in human cells. Mol Cell 54, 698-710.
Ouchi, R., Togo, S., Kimura, M., Shinozawa, T., Koido, M., Koike, H., Thompson, W., Karns, R.A., Mayhew, C.N., McGrath, P.S., et al. (2019). Modeling Steatohepatitis in Humans with Pluripotent Stem Cell-Derived Organoids. Cell Metab 30, 374-384 e376.
Pascual, M., Gomez-Lechon, M.J., Castell, J.V., and Jover, R. (2008). ATF5 is a highly abundant liver-enriched transcription factor that cooperates with constitutive androstane receptor in the transactivation of CYP2B6: implications in hepatic stress responses. Drug Metab Dispos 36, 1063-1072.
Patro, R., Duggal, G., Love, M.I., Irizarry, R.A., and Kingsford, C. (2017). Salmon provides fast and bias-aware quantification of transcript expression. Nat Methods 14, 417-419.
Peter, I.S., and Davidson, E.H. (2011). A gene regulatory network controlling the embryonic specification of endoderm. Nature 474, 635-639.
Radley, A.H., Schwab, R.M., Tan, Y., Kim, J., Lo, E.K.W., and Cahan, P. (2017). Assessment of engineered cells using CellNet and RNA-seq. Nat Protoc 12, 1089-1102.
Rizzo, G., Renga, B., Mencarelli, A., Pellicciari, R., and Fiorucci, S. (2005). Role of FXR in regulating bile acid homeostasis and relevance for human diseases. Curr Drug Targets Immune Endocr Metabol Disord 5, 289-303.
Robinson, J.T., Thorvaldsdottir, H., Winckler, W., Guttman, M., Lander, E.S., Getz, G., and Mesirov, J.P. (2011). Integrative genomics viewer. Nat Biotechnol 29, 24-26.
Robinson, M.D., McCarthy, D.J., and Smyth, G.K. (2010). edgeR: a Bioconductor package for differential expression analysis of digital gene expression data. Bioinformatics 26, 139-140.

\* cited by examiner

FIGS. 6A-6E
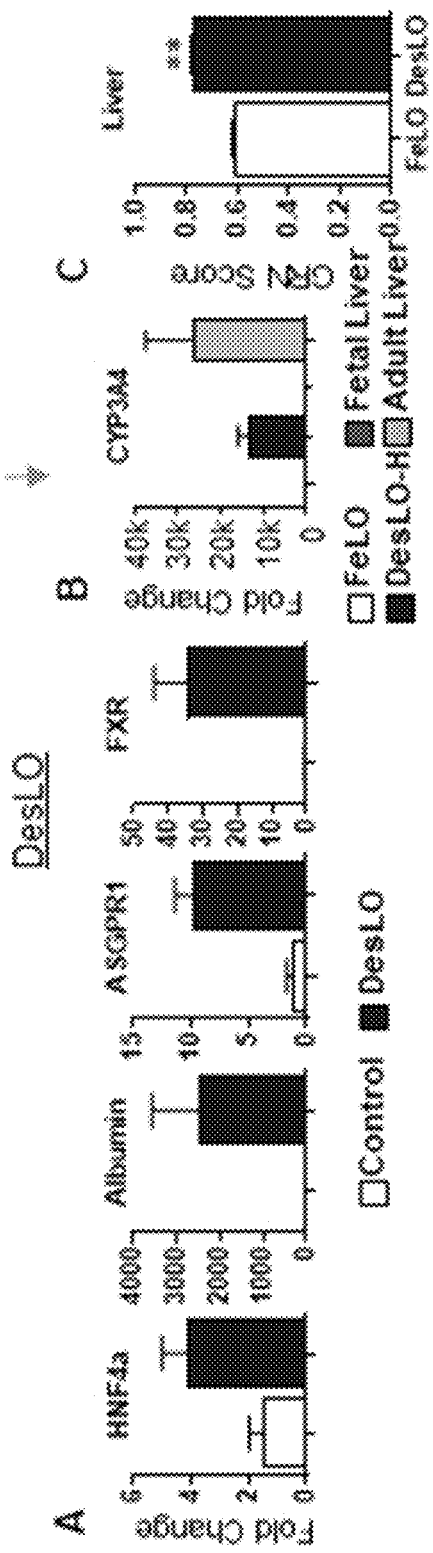
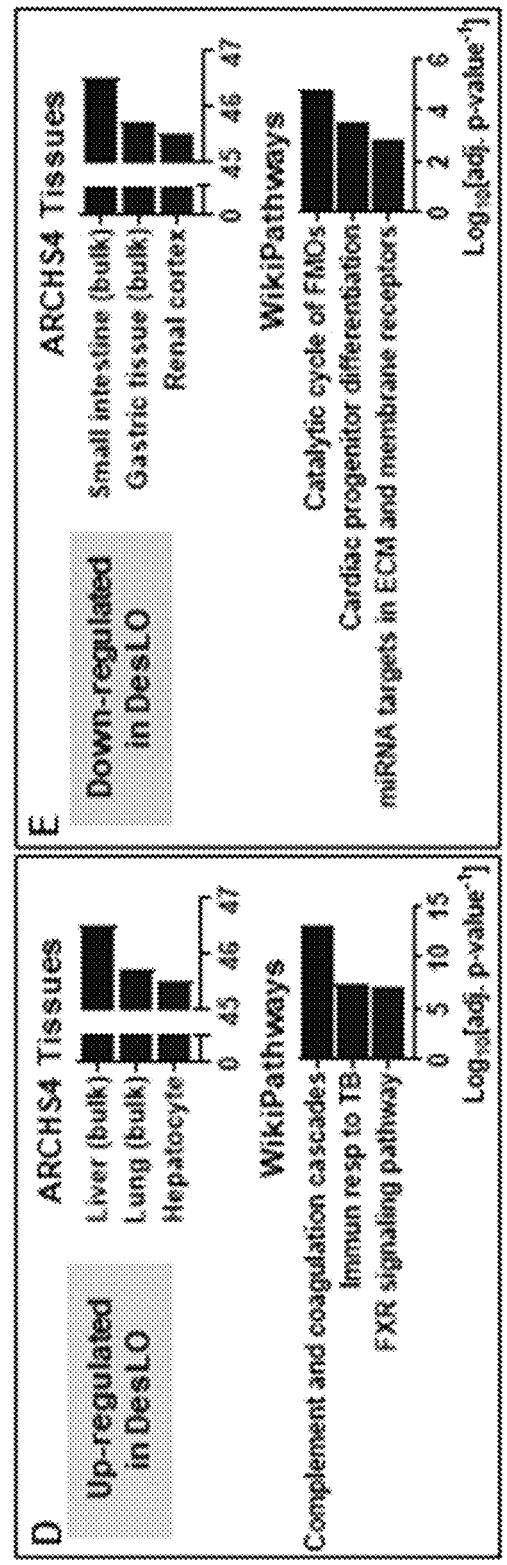

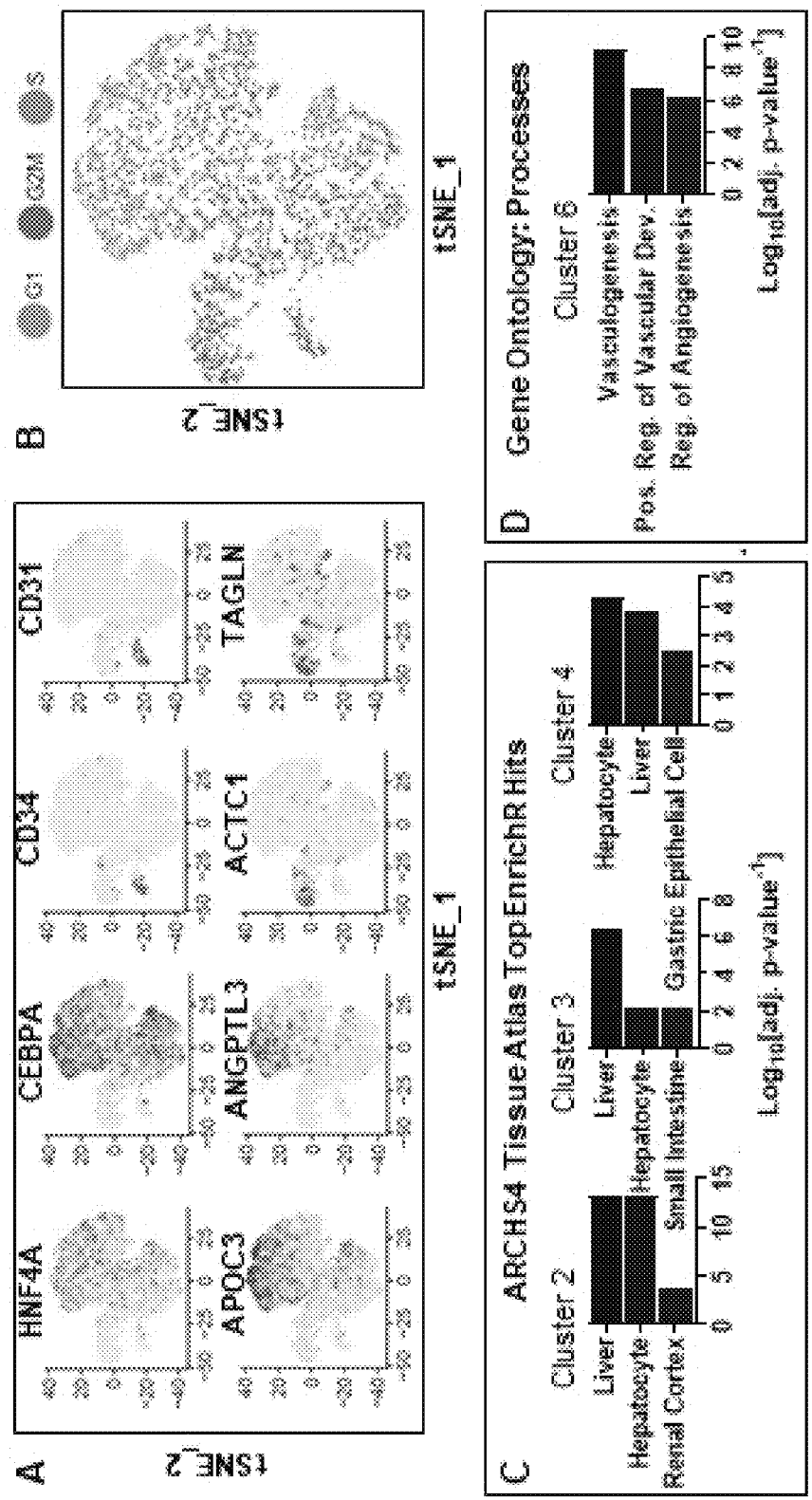
FIGS. 15A-15D (S4)

NEXT GENERATION DESIGNER LIVER ORGANOIDS AND THEIR METHODS OF PREPARATION AND USE

CROSS-REFERENCE TO RELATED APPLICATIONS

This application is a national stage filing under 35 U.S.C. § 371 of International Application No. PCT/US2019/036410, filed Jun. 10, 2019, which claims priority to U.S. Provisional Application Nos. 62/682,916, filed Jun. 9, 2018, and 62/775,505, filed Dec. 5, 2018, each of which is incorporated herein by reference as if set forth in its entirety.

REFERENCE TO A SEQUENCE LISTING SUBMITTED VIA EFS-WEB

The content of the ASCII text file of the sequence listing named "112624-01231 seglist.TXT" which is 5.13 kb in size was created on Dec. 8, 2020, and electronically submitted via EFS-Web with the application is incorporated herein by reference in its entirety.

BACKGROUND

To date, primary human hepatocytes serve as the gold standard for studying liver biology or drug induced liver toxicity/injury. Hepatocytes are metabolically active cells that execute such functions as glucose homeostasis, bilirubin excretion, protein synthesis, and secretion of major plasma proteins. However, in conventional two-dimensional (2D) in vitro cell cultures, primary hepatocytes dedifferentiate rapidly and lose hepatocyte-specific functions. This problem has led to development of new in vitro culture systems for maintaining human hepatocytes function over an extended period of time. These culture systems use three-dimensional (3D) spheroid formation, specific medium conditions (e.g., addition of dexamethasone), scaffolds, and co-culturing with other cell types to maintain hepatocytes functional over weeks. However, the cost of acquiring and accessibility to primary human hepatocytes limit the success of these efforts and complicate scaling up practices. Furthermore, primary human hepatocytes do not provide patient-specific information of liver metabolic activity or drug induced toxicity.

Recently, multiple versions of stem cell-derived hepatocytes and liver organoids have been developed that serve as invaluable platforms for disease modeling and parsing developmental processes in a personalized manner. However, many of these systems fail to demonstrate a mature liver phenotype, and these system mostly retain fetal phenotypes. Importantly, many of these systems also lack mature Cytochrome P450 (CYP) enzymatic activity and require either induction through non-physiological medium components or in vivo transplantation to achieve desired adult level activity. Thus, organoids generated so far lack spatiotemporal control, robustness, and diverse heterotypic cellular populations that exist in vivo and importantly exhibit fetal and immature phenotype in vitro. As such, these in vitro systems fall short in delivering their promises for pharmaceutical applications, regenerative medicine or human development and disease modeling. Therefore, there is an unmet need in the art to develop human stem cell derived systems that can recapitulate adult level function and activity ex vivo. Novel technologies that surpass these limitations would provide immense opportunities to advance translational utility of these human liver models for precision medicine.

SUMMARY

A patient-matched stem cell-derived liver organoid could be used to uncover individual disease mechanisms, transform drug discovery and facilitate therapeutic transplantations. However, obtaining fully mature and functional stem cell-derived liver cells and organoids is a major challenge. The present disclosure relates to the development of methods in which, by turning on specific set of genes, in vitro-engineered liver tissues can be developmentally steered towards human in vivo phenotypes.

In a first aspect, provided herein is a method for producing a synthetic mature liver organoid. The method can comprise, or consist essentially of, the steps of: (a) introducing into cells of a Day-5 fetal liver organoid one or more lentiviral constructs comprising an inducible transgene encoding at least one transcription factor selected from ATF5, Prox1, MLXIPL1, and CREB3L3, wherein, prior to introducing the one or more lentiviral constructs, the Day-5 fetal liver organoid comprising a cell population comprising at least 70% CXCR4" cells; (b) inducing expression of the inducible transgene by contacting the fetal liver organoid of step (a) to a small-molecule inducer of transgene expression; (c) culturing the induced organoid of step (b) for about 5 days; (d) transducing cells of the cultured organoid of step (c) one or more CRISPR cassettes comprising a nucleic acid sequence encoding dCas9 and one or more gRNAs that bind to the human CYP3A4 locus; and (e) culturing the transduced cultured organoids of step (d) for at least 5 days, thereby producing a mature liver organoid comprising albumin$^+$/FGF21$^+$/G6PC$^+$/FXR$^+$ hepatocytes and augmented vasculature and exhibiting CYP3A4 protein metabolizing activity. The transgene can be inducible by doxycycline. The one or more gRNAs can be under control of a constitutively active promoter such as phEFla. The one or more gRNAs is under control of a tissue-specific promoter such as pAAT.

The mature liver organoid can exhibit one or more properties selected from the group consisting of: (i) an interconnected, augmented vasculature; (ii) differentiated cells within the mature liver organoid mutually contact each other in three dimensions; (iii) more than one layer of cells; and (iv) a function or property characteristic of human liver tissue in vivo or in situ. The mature liver organoid can express CYP7A1, NR1H4 (FXR), and NROB2 (SHP) and exhibit bile acid synthesis. The method can further comprise contacting a TGFβ to a mature liver organoid, whereby fibrogenesis and expression of Desmin increased in the contacted organoid relative to an uncontacted control.

The Day-5 fetal liver organoid can be obtained according to the following steps: (a) introducing into human pluripotent stem cells one or more lentiviral constructs comprising an inducible transgene encoding GATA-binding protein 6 (GATA6); (b) inducing expression of the GATA6 transgene in the hiPSCs; and (c) culturing the induced hiPSCs in the presence of a pluripotency supporting medium for about 5 days, whereby a cell population comprising at least 70% CXCR4$^+$ cells is obtained. The hPSCs of step (a) can be cultured in a chemically defined medium comprising a Rho Kinase (ROCK) inhibitor. The ROCK inhibitor can be Y-27632. The human pluripotent stem cells can be human embryonic stem cells or human induced pluripotent stem cells.

In some cases, the method of obtaining a Day-5 fetal liver organoid further comprises the step of (d) culturing the cell population of step (c) in a basal cell culture medium for about 10 days, whereby a cell population comprising CD34$^+$/CD93$^+$ endothelial-like cells, CD51$^+$/NES$^+$/

PDGFRα+ mesenchymal stem cell-like cells, DES+ stellate-like cells, and CEBPα+ hepatocyte-like cells is obtained.

In another aspect, provided herein is a synthetic mature liver organoid obtained according to any of the methods provided herein.

In a further aspect, provided herein is a method of in vitro screening of an agent. The method can comprise or consist essentially of the following steps: (a) contacting a test agent to a synthetic mature liver organoid obtained according to a method provided herein; and (b) detecting an effect of the agent on one or more cell types within the contacted mature liver organoid. The agent can be screened for toxicity to human liver tissue. Detecting can comprise detecting at least one effect of the agent on morphology or life span of cells or tissues within the contacted mature liver organoid, whereby an agent that reduces the life span of the cells or tissues or has a negative impact on the morphology of the cells or tissues is identified as toxic to human liver tissue. Detecting can comprise performing a method selected from RNA sequencing, gene expression profiling, transcriptome analysis, metabolome analysis, detecting a reporter or sensor, protein expression profiling, Förster resonance energy transfer (FRET), metabolic profiling, and microdialysis. The agent can be screened for an effect on gene expression and wherein detecting comprises assaying for differential gene expression relative to an uncontacted mature liver organoid.

In another aspect, provided herein is a method for producing functional liver tissue in vivo, the method comprising transplanting into a mammal a synthetic mature liver organoid obtained according to any method of this disclosure, whereby the transplanted organoid induces production of liver tissue at the site of transplantation, wherein the produced liver tissue exhibits exhibiting CYP3A4 protein metabolizing activity, hepatic bile acid receptor FXR activity, and bile acid synthesis. The mammal can be a human and the synthetic mature liver organoid can comprise human cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features and advantages of the present disclosure will be more fully understood from the following detailed description of illustrative embodiments taken in conjunction with the accompanying drawings.

FIGS. 6A-6K. (A) qRT-PCR panel for the indicated genes for hEF1a ATF5 DesLO relative to transduction control FeLO shows upregulation of liver-related genes (n=3-5). (B) CYP3A4 expression measured by qPCR in FeLO, high MOI DesLO (DesLO-H; MOI=100 or 200), fetal liver, and adult liver shows DesLO CYP3A4 expression in range of adult liver tissue is obtainable. (n=3-4). (C) Graphical depiction of the CellNet GRN scores for the liver in D17 FeLO and DesLO tissues sets show significant increased liver identity in DesLO. Significance relative to FeLO; **p<0.01. (n=2) two-tail T-test. (D) EnrichR generated adjusted p-values of D17 DesLO upregulated genes (qualified by >2 fold change over D0 with at least 2 mean transcript reads per million) used to predict upregulated tissue identity and functions using the ARCHS4 and WikiPathways libraries. (E) EnrichR generated adjusted p-values of D17 DesLO downregulated genes (qualified by <0.5 fold change over D0 with at least 2 mean transcript reads per million) used to predict downregulated tissue identity and functions using the ARCHS4 and WikiPathways libraries. (F) Lipid droplet visualization in DesLO via Oil Red O staining. (G) AAT promoter (pAAT)-driven YFP expression shown with phase/YFP overlay. (H) Immunofluorescence staining of AAT and YFP shows that AAT promoter-driven YFP co-expresses with AAT and does not express in the endothelial cells within the multicellular culture, confirming the specificity of the AAT promoter system. (I) Graphical depiction of the CellNet GRN scores for the liver in D17 DesLO with ATF5 driven by either the hEF1a or AAT promoter (n=2). (J) qRT-PCR for CYP3A4 for FeLO and DesLO transduced with pAAT dCas9 at two different MOI regimes. pAAT-L indicates CYP3A4 gRNA and pAAT dCas9 at 9 MOI (n=2) and pAAT-H indicates CYP3A4 gRNA and pAAT dCas9 at 100 or 200 MOI (n=6). FeLO n=3. ([J] K) qRT-PCR panel for the indicated genes for pAAT_ATF5 DesLO relative to transduction control FeLO shows upregulation of liver-related genes (n=3-4).

FIGS. 15A-15I. (A) t-distributed Stochastic Neighbor Embedding plot indicated genes shows regionalization and specificity of genes correlated with hepatic and stromal identities to particular clusters. (B) t-distributed Stochastic Neighbor Embedding plot showing the cell cycle state of each cell indicating that cluster 1 is enriched for S-phase genes. (C) EnrichR generated adjusted p-values of clusters 2-4 (qualified by >2 fold change over D0 with at least 2 mean transcript reads per million) for enriched ARCHS4 tissues. (D) EnrichR generated adjusted p-values of cluster 6 (qualified by >2 fold change over D0 with at least 2 mean transcript reads per million) for enriched ARCHS4 tissues. (E) Binary heat map for the indicated tissues and tissue-specific genes shows that DesLO clusters align with the putative tissue identities. Selection and expression criteria explained in materials and methods. (F-I) Immunofluorescence staining showing the associations of hepatocyte like, pericyte-like, and endothelial-like cells through staining of cell-type specific markers.

DETAILED DESCRIPTION

I. Definitions

Figure 1:
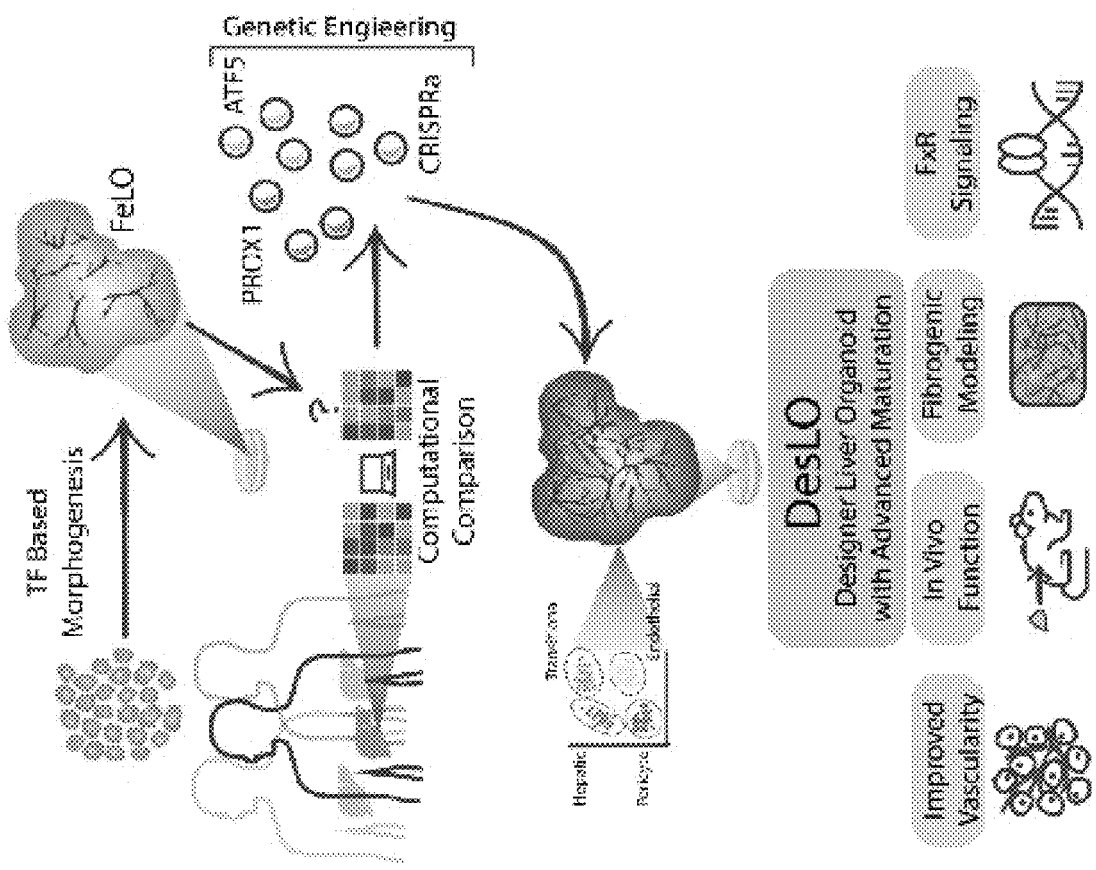
FIG. 1 is a schematic illustration of an exemplary workflow for obtaining a synthetic designer liver organoid with advanced maturation ("mature liver organoid") in vitro using transcription factor-based morphogenesis and CRISPR-based genetic engineering, which is in some cases informed by computational analysis of synthetic fetal liver organoids to identify gene products, signaling factors, and gene regulatory networks of interest.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "autologous" is meant to refer to any material derived from the same individual to which it is later to be re-introduced into the individual.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of cells (e.g., gene edited hepatocytes). In one embodiment, the cells that are expanded ex vivo increase in number relative to the number originally present in the culture. In another embodiment, the cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the terms "genetically engineered" and "genetically modified" are used interchangeably and refer to a cell that has been modified to comprise a non-naturally occurring nucleic acid molecule that has been created or modified by the hand of man (e.g., using recombinant or gene editing DNA technology) or is derived from such a molecule (e.g., by transcription, translation, etc.). A cell that contains an exogenous, recombinant, synthetic, and/or otherwise modified polynucleotide is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart).

"Insertion/deletion", commonly abbreviated "indel," is a type of genetic polymorphism in which a specific nucleotide sequence is present (insertion) or absent (deletion) in a genome.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell. Molecules may be modified in many ways, including chemically, structurally, and functionally. Cells may be modified through the introduction of nucleic acids. In certain embodiments, a modified cell may be "genetically modified" or "genetically edited", wherein one or more nucleic acids in the cell are altered.

By the term "modulating," as used herein, is meant mediating a detectable increase or decrease in the level of an expression level or response in a cell or subject compared with the level of an expression level or response in the cell or subject in the absence of a treatment or compound, and/or compared with the level of expression or response in an otherwise identical but untreated cell or subject. The term encompasses perturbing and/or affecting a native signal, native expression level, or response thereby mediating a beneficial therapeutic response in a subject, preferably, a human.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "pluripotency" refers to a cell's ability to differentiate into form all lineages of the body or soma (i.e., the embryo proper), including cells of all three germ layers (the ectoderm, endoderm, and mesoderm).

As used herein, the term "pluripotent stem cell" refers to a cell capable of continued self-renewal and of capable, under appropriate conditions, of differentiating into cells of all three germ layers. Examples of pluripotent stem cells (PSCs) include embryonic stem cells (ESCs) and induced pluripotent stem cells (iPSCs). As used herein, "embryonic stem cells" or "ESCs" mean a pluripotent cell or population of pluripotent cells derived from an inner cell mass of a blastocyst. See, e.g., Thomson et al., Science 282:1145-1147 (1998). These cells express Oct-4, SSEA-3, SSEA-4, TRA-1-60, and TRA-1-81, and appear in vitro as compact colonies having a high nucleus to cytoplasm ratio and prominent nucleolus. As used herein, the term "iPS cell" or "iPSC" refers to a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., Science 318:1917-1920 (2007). iPSCs are substantially genetically identical to their respective differentiated somatic cell of origin, display characteristics similar to higher potency cells, such as ES cells, and cells are obtained by reprogramming non-pluripotent cells (e.g., multipotent cells, oligopotent cells, unipotent cells, and terminally differentiated cells) such as somatic cells. ESCs and iPSCs are available from various commercial suppliers.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

II. Compositions and Methods of Making Them

Liver transplantation is the only therapeutic option for patients with end-stage liver disease but shortages of matched donors limit its use. The current drug development pipeline lacks tools to assess human tissue-level toxicities and inter-individual variations. Enormous amounts of money (~$3-5B) and time (12-15 years) are devoted to drug discovery, but many candidate drugs fail when tested on human subject, primarily due to organ toxicity, liver toxicity in particular.

The rapid advancement of the stem cell-derived organoid field has opened up an unmatched possibility to generate complex human tissues from stem cells opening myriad novel biomedical applications. Several examples of human organoids have been developed that can emulate structures and functions associated with human organs such as gut, kidney, liver, lung, and brain. Organoid technology has enabled us to begin to understand multiple facets of diseases such as microcephaly, autism, ulcerative colitis, and Crohn's disease and cancer. Overall, they exhibit exciting potential to model key aspects of human development and disease processes, as well as advance efforts towards precision medicine and human disease modeling.

While hepatocyte-only cultures are an invaluable cell system, unfortunately a single cell population like hepatocytes cannot fully capture the complexity of a human organ such as liver. The use of hepatocytes for cell therapies and drug discovery are limited because the cell dedifferentiate and lose liver-specific functionality when cultured in vitro. Moreover, hepatocytes are incapable of replicating ex vivo. The addition of non-physiological levels of molecules such as dexamethasone and the reconstitution of a subset of liver cell types can slow the dedifferentiation process, but these steps are insufficient to sustain long term in vitro culture or to support large scale cell production. Additionally, due to large inter-individual differences for personalized medicine, patient-matched cells are required. These challenges leave us with a very limited cell source for precision drug testing and for regenerative therapies. To solve this dilemma, innovative strategies for generating functionally mature liver tissues and cells are in high demand. Hepatocytes or liver tissues developed from genetically identical human induced pluripotent stem cells (hiPSCs) might surpass inter-individual differences in drug metabolism, which are a foremost basis of unpredictable side effects in the pharmacological field, and also empower cell transplantation therapy for metabolic or lethal liver diseases without rigorous immunosuppressive strategies. A patient-matched stem cell-derived liver organoid could be used to uncover individual disease mechanisms, transform drug discovery and facilitate therapeutic transplantations. However, obtaining fully mature and functional stem cell-derived liver cells and organoids is a major challenge with no fundamental solution.

The inventors previously developed a self-organizing "fetal" liver organoid that emerges from co-differentiation of multiple progenitor cells following about 5 days of expression of a doxycycline-inducible GATA6 transgene in a culture medium containing bFGF/FGF2 and TGF-β. The "fetal" liver organoids comprise human endodermal and mesodermal layers, hepatoblasts, endothelial, biliary and stellate (-like) cells, mirroring true complexity of a human fetal liver. However, synthetic liver organoids generated to date lack key characteristics of adult liver tissue such as active P450 enzymes, hepatic bile acid receptor FXR, and drug metabolizing functions. Since they lack adult cell types and functional characteristics of adult liver tissue, such liver organoids are incapable of modeling complex multicellular diseases of adulthood.

The present disclosure relates to the discovery that by turning on specific set of genes, the development of in vitro-engineered liver tissues can be steered towards human in vivo phenotypes of mature liver tissue. Accordingly, provided herein are methods of producing liver organoids that exhibit mature, enhanced, and prolonged liver-specific function ex vivo without a need for complex culture medium use or in vivo implantation (Designer Liver Organoids or abbreviated as "DesLOs"). As illustrated in FIG. 1, the methods comprise obtaining a synthetic designer liver organoid with advanced maturation ("mature liver organoid") in vitro using transcription factor-based morphogenesis and CRISPR-based genetic engineering, which is in some cases informed by computational analysis of synthetic fetal liver organoids to identify gene products, signaling factors, and gene regulatory networks of interest. The resulting DesLO exhibits improved vascularity relative to the fetal liver organoid, in vivo function as demonstrated using transplantation into animal models, FxR signaling, bile acid production, and fibrogenesis. As used herein, the term "organoid" refers to a tissue-like structure (i.e., exhibiting structural and functional properties of a particular tissue type) that is assembled in vitro by the separate addition and self-organization of various cell populations including, but not limited to, pluripotent stem cells, fetal stem cells, tissue-specific progenitors, and differentiated cells. As used herein, the term "population" refers to a collection of cells, such as a collection of progenitor and/or differentiated cells. As used herein, the term "differentiated" as it relates to the cells of this disclosure can refer to cells that have developed to a point where they are programmed to develop into a specific type of cell and/or lineage of cells. Similarly, the term "non-differentiated" or "undifferentiated" as it relates to the cells of this disclosure can refer to progenitor cells, i.e., cells having the capacity to develop into various types of cells within a specified lineage.

In a first aspect, provided herein is a method for producing mature multicellular liver organoids, where the method comprises or consists essentially of modulating expression of one or more genes in cells of an in vitro-engineered liver organoid. In particular, the methods provided herein comprise modifying gene expression in cells of an in vitro-engineered liver organoid using Clustered Regularly Interspaced Short Palindromic Repeat (CRISPR)-based epigenetic modulation. The growth and differentiation of hepatoblasts are regulated by various extrinsic signals. Accordingly, the methods provided herein employ CRISPR-based techniques to modulate expression of one or more genes that encode hepatocyte maturation factors and/or are known to be differentially expressed in mature hepatocytes relative to "fetal" cell types (e.g., hepatoblasts) in order to promote formation of DesLOs. For example, CRISPR can be used to modulate expression of one or more genes selected from ATF5 (Activating Transcription Factor 5), PROX1 (Prospero Homeobox 1), Onecut1 (One Cut Homeobox 1; also known as Hepatocyte Nuclear Factor 6), Onecut2 (One Cut Homeobox 2; also known as Hepatocyte Nuclear Factor 6-Beta), FXR (farnesoid X receptor), NR112 (encoding pregame X receptor or "PXR"), NR113 (encoding constitutive androstane receptor or "CAR"), ZGPAT (Zinc Finger CCCH-Type And G-Patch Domain Containing), MLXIPL.I (MLX Interacting Protein), and/or CREB3L3 (CAMP Responsive Element Binding Protein 3 Like 3). Upregulation of particular genes will promote maturation of fetal hepatic stem/progenitor cells to mature, differentiated hepatocytes. For example, ATF5 is an abundant liver-enriched transcription factor that is upregulated in mature hepatocytes. Overexpression of this maturation factor will promote maturation of cells within the liver organoid to differentiated, "adult" hepatocytes, thus forming a DesLOs. In other cases, CRISPR-based technology is used to suppress or downregulate expression of particular genes in cells of a fetal liver organoid. For example, PROX1 is highly expressed in hepatoblasts (liver progenitor cells) and is believed to support long-term proliferation of fetal hepatic stem/progenitor cells. In some cases, CRISPR-based technology can be used to increase expression of PROX1 in cells of a fetal liver organoid. In other cases, CRISPR-based technology can be used to suppress expression of PROX1 in cells of a fetal liver organoid. In some cases, it can be useful to detect expression of hepatocyte-specific markers such as albumin and apolipoprotein B (APOB) in gene edited cells. Albumin and APOB should not be expressed in liver non-parenchymal cells (e.g., Kupffer cells, hepatic stellate cells (HSCs), sinusoidal endothelial cells, myofibroblasts). Exemplary ATF5 and PROX1 coding sequences are provided in the concurrently filed sequence listing as SEQ ID NOs: 4 and 5.

In some cases, the methods further comprise using Clustered Regularly Interspaced Short Palindromic Repeat (CRISPR)-based techniques to modulate expression of one or more genes associated with liver function. In some cases, the CRISPR-based techniques comprising introducing synthetic gene circuits for efficient transcriptional activation of target genes. As described herein, CRISPR-based transcriptional modulators permit spatiotemporal control of expression of particular endogenous genes in iPSC-derived multicellular tissues and organoids. For example, the methods comprise transducing into cells of a liver organoid a CRISPR transcriptional activation cassette to increase transcription of the human gene encoding of enzyme CYP3A. The inventors previously described that fusion of a transcriptional activation or repression domain to a catalytically inactive Cas9 protein (dCas9) enables site-specific gene activation or repression by binding endogenous or synthetic promoter regions. dCas9 retains its DNA binding capacity and can be targeted to any DNA sequence of interest by means of altering the 20nt sequence on the 5' end of gRNA. Expression of gRNAs from RNA Pol II- and Pol III-based promoters to achieve dCas9/gRNA mediated transcriptional repression from a library of synthetic promoters.

In some cases, the CRISPR cassette comprises a nucleic acid sequence encoding dCas9, an RNA binding aptamer sequence (e.g., encoding a MS2 bacteriophage coat protein) fused to a transcriptional repressor or activation domains (e.g., VP64, VP 16, p65-), and specific guide RNAs. In a particular embodiment, the CRISPR cassette comprises nucleic acid sequence encoding dCas9, MS2-P65-HSF1, and one or more gRNAs that bind to the human CYP3A4 locus. In some cases, the promoter is a constitutively active promoter such as a phEF1a promoter. In some cases the promoter is a cell-type specific promoter such as a pAAT promoter.

In some cases, cells are transduced with lentiviral delivery of a cassette carrying gRNAs that bind around 200bps upstream of transcriptional start site (TSS) of Cytochrome P450 3a4 (CYP3A4), an important gene for metabolic activity of mature liver. In some cases, the cassette comprises nucleic acid sequence encoding dCas9, an aptamer-mediated recruitment construct comprising an activation domain (e.g., MS2-P65-HSF1), and 2 gRNAs targeted to CYP3A4 promoters. Exemplary gRNAs are provided in the concurrently filed sequence listing as SEQ ID NOs: 2 and 3.

In some embodiments, the method for producing a mature liver organoid comprises, or consists essentially of, the steps of
(a) introducing into cells of a Day-5 fetal liver organoid one or more lentiviral constructs comprising an inducible transgene encoding at least one transcription factor selected from ATF5, Prox1, MLXIPL1, and CREB3L3, wherein, prior to introducing the one or more lentiviral constructs, the Day-5 fetal liver organoid comprising a cell population comprising at least 70% CXCR4+ cells;
(b) inducing expression of the inducible transgene by contacting the fetal liver organoid of step (a) to a small-molecule inducer of transgene expression;
(c) culturing the induced organoid of step (b) for about 5 days;
(d) transducing cells of the cultured organoid of step (c) with one or more CRISPR cassettes comprising nucleic acid sequence encoding dCas9, and a gRNA that binds to the human CYP3A4 locus under control of a promoter; and
(e) culturing the transduced cultured organoids of step (d) for at least 7 days, thereby producing a mature liver organoid comprising albumin$^+$/FGF21$^+$/G6PC$^+$/FXR$^+$ hepatocytes and augmented vasculature and exhibiting CYP3A4 protein metabolizing activity.

Figure 7:
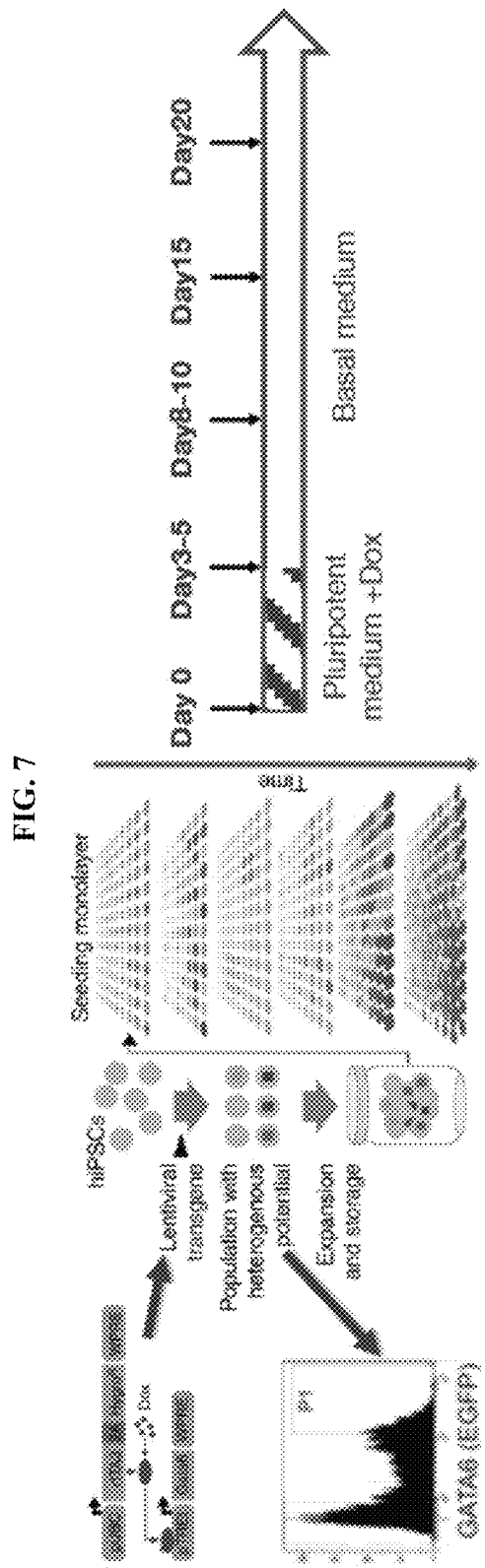
FIG. 7 demonstrates Piggybac-based engineering of heterogeneous GATA6 expression.
Figure 8:
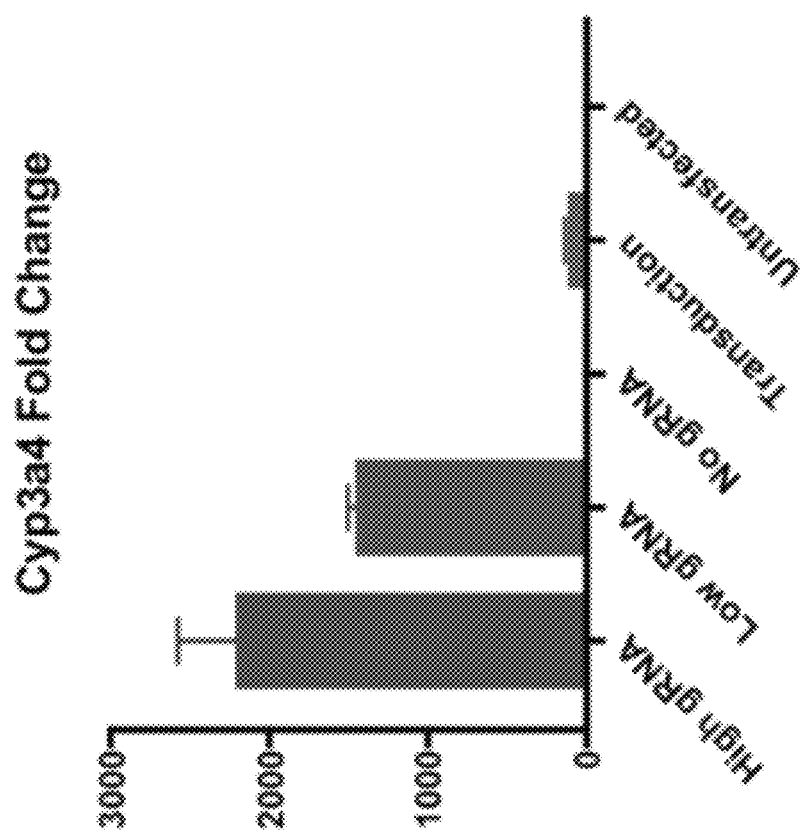
FIG. 8 demonstrates that Cas9-based activation in HEK is a function of gRNA mass transfected, and that transduction is less efficient than transfection.
Figure 9:
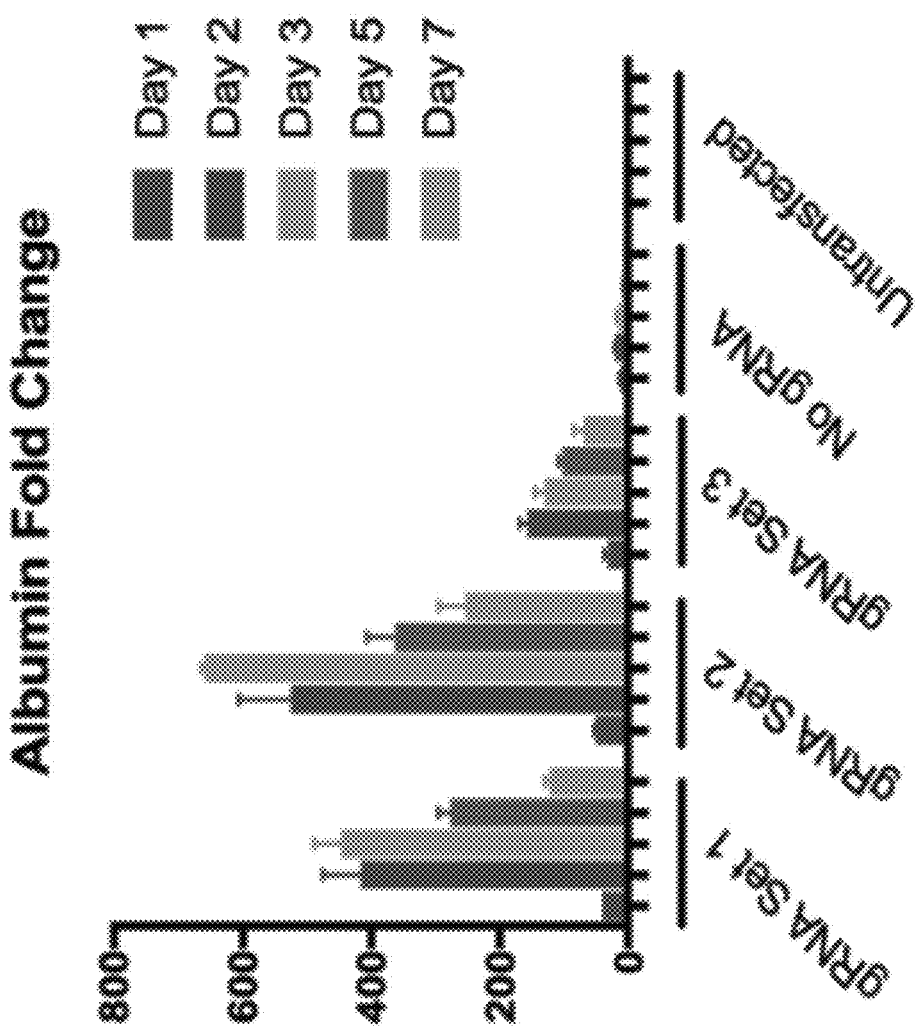
FIG. 9 demonstrates that gene activation efficacy depends on gRNA target sites, and transfection demonstrates time-dependent activation.
Figure 10:
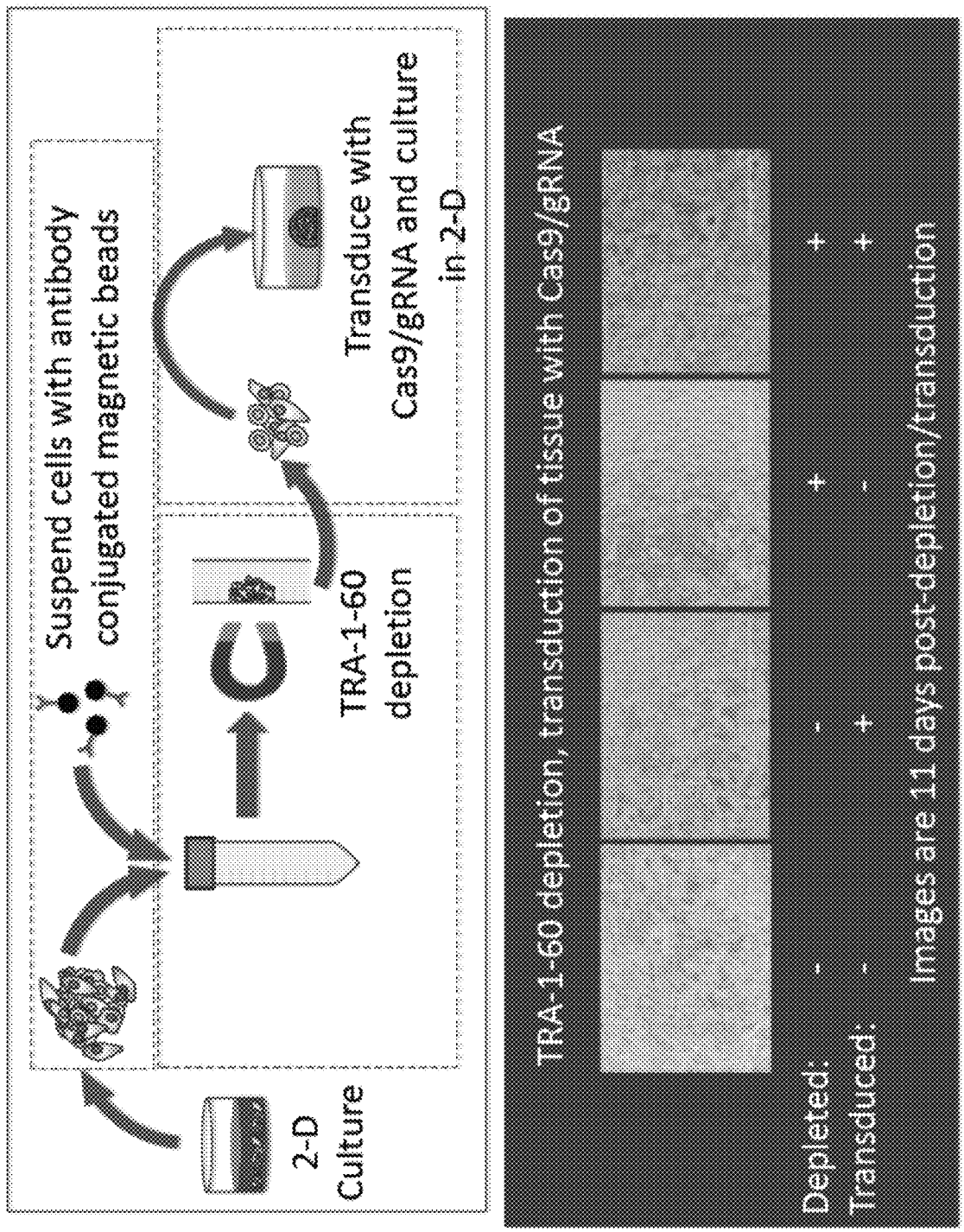
FIG. 10 demonstrates (top) day 5 MACS depletion of undifferentiated cells from tissue, and (bottom) TRA-1-60 depletion with or without transduction of tissue with Cas9/gRNA.
Figure 11:
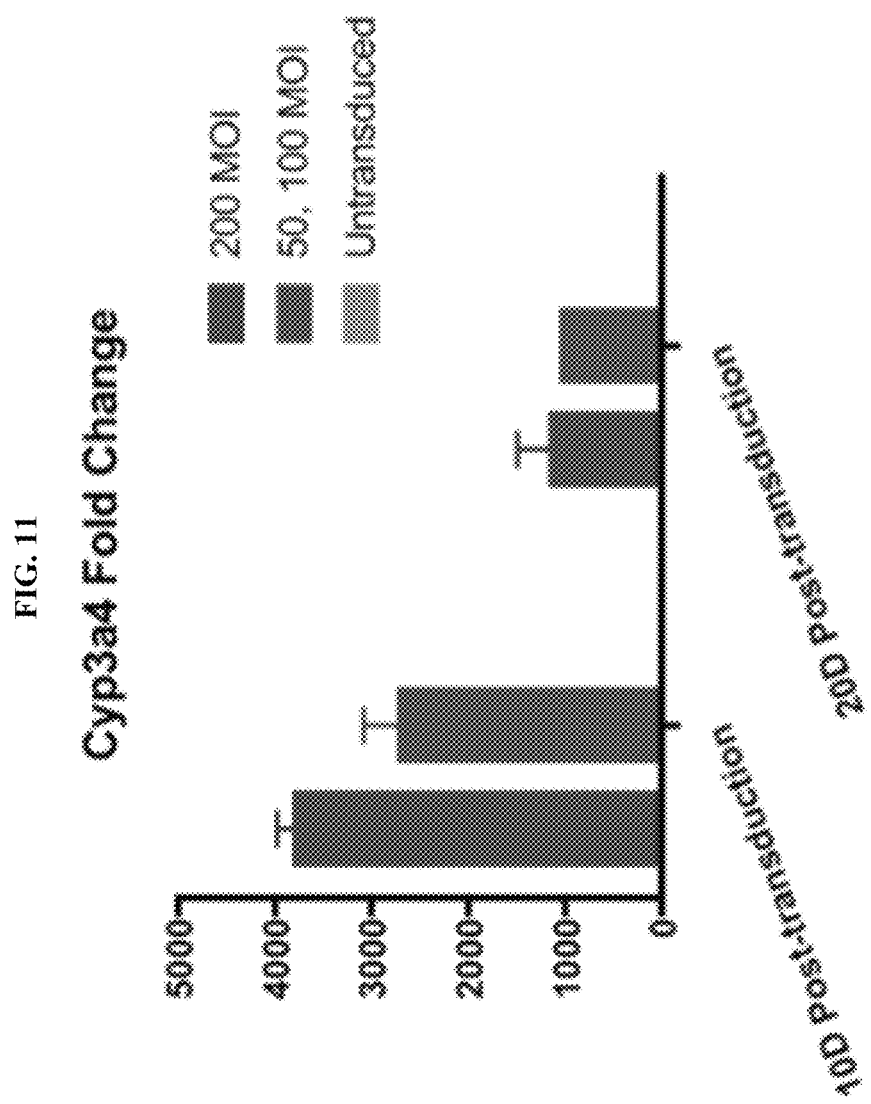
FIG. 11 demonstrates that transduction of Day 10 organoids with dCas9/gRNA lentivirus allows for sustained endogenous gene activation.
Figure 12:
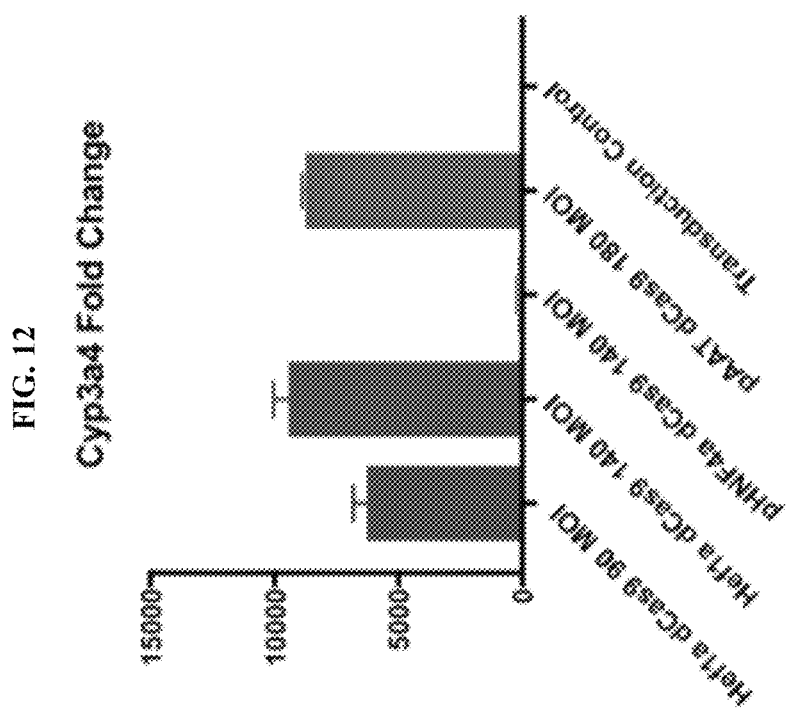
FIG. 12 demonstrates Cy3a4 activation as a function of transduction MOI and dCas9 promoter.
Figure 13:
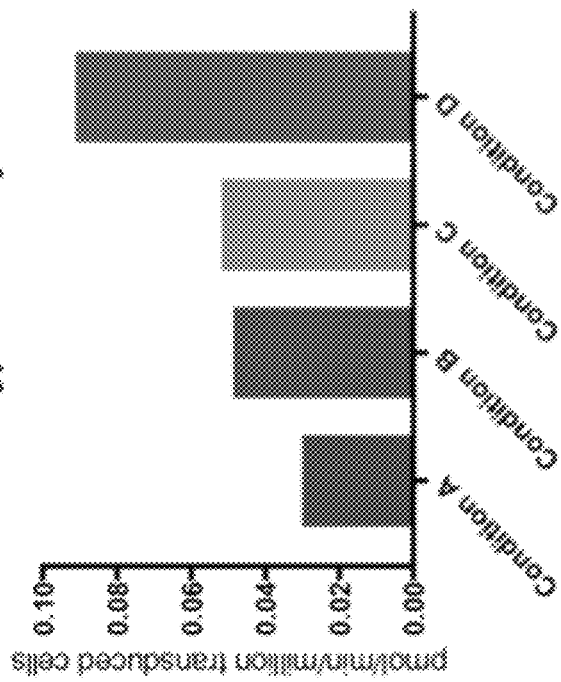
FIG. 13 demonstrates metabolic activity in engineered organoids as a function of dCas9 promoter and culture medium.

In some cases, the transduced cultured organoids of step (d) are cultured for at least 7, 8, 9, 10, 11, 12, 13, 14, 15, 16, 17, 18, 19, or 20 days or more (see FIG. 7) to produce a mature liver organoid comprising albumin$^+$/FGF21$^+$/G6PC$^+$/FXR$^+$ hepatocytes, augmented vasculature, and exhibiting CYP3A4 protein metabolizing activity. As used herein, the term "augmented vasculature" refers to differential gene expression and distinct vascular phenotypes exhibited in mature liver organoids relative to fetal liver organoids. For example, as described herein, it was determine that DesLOs exhibit different angiogenesis-related transcriptional signatures than fetal liver organoids. In particular, DesLOs exhibit increased expression of angiogenic growth factors such as VEGFA, PDGFB, and FGF2, as well as endothelial identity markers ERG, TIE1, PECAM1, VWF, and notably, the liver sinusoidal endothelial cell marker LYVE-1 (see FIG. 16A). Without being bound to any particular theory or mechanism of action, it is believed that distinct expression of cognate ligands and receptors is indicative of complex intercellular signaling networks in DesLO (see FIG. 16B).

In some cases, one or more transgenes for modulating expression of transcription factors ATF5, Prox1, MLXIPL1, and CREB3L3 and/or the CRISPR cassette for modulating human CYP3A4 are introduced sequentially. In other cases, one or more transgenes and/or CRISPR cassettes are introduced in tandem.

In some cases, the inducible transgene encoding Prox1, and the CRISPR cassette is configured to repress expression of Prox1. As used herein, the term "CRISPR cassette" refers to any engineered nucleic acid comprising elements of a synthetic regulatory circuit configured for more efficient gene expression modulation and/or gene editing by CRISPR.

In some cases, cells are transduced with lentiviral delivery of a synthetic regulatory circuits comprising gRNAs that bind around 200bps upstream of transcriptional start site (TSS) of Cytochrome P450 3a4 (CYP3A4), an important gene for metabolic activity of mature liver. In some cases, the cassette comprises nucleic acid sequence encoding dCas9, an aptamer-mediated recruitment construct comprising an activation domain (e.g., MS2-P65-HSF1), and 2 gRNAs targeted to CYP3A4 promoters. Commercially available software and known gRNA design protocols can be used to design gRNAs suitable for use in these methods.

Figures 4A, 4B, 4C, 4D:
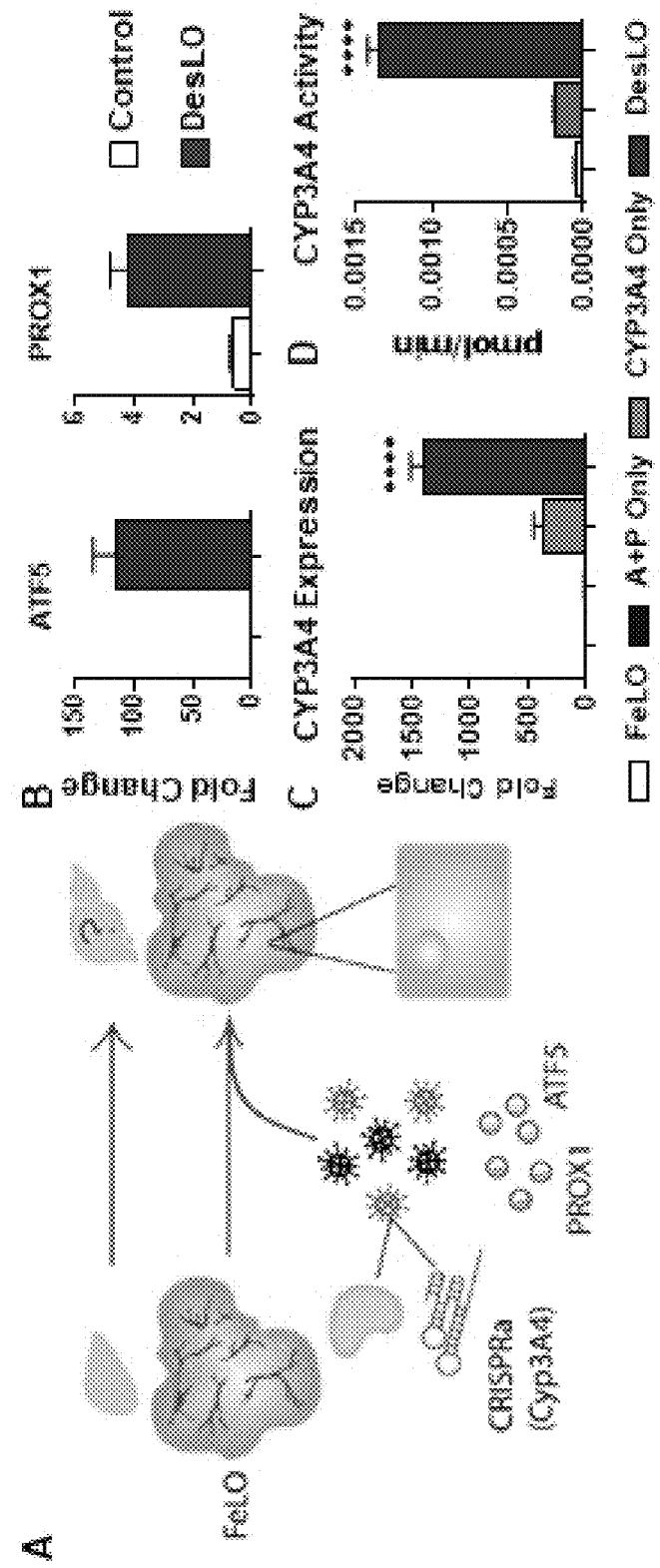
FIGS. 4A-4K. (A) Schematic of workflow for incorporation of ATF5, PROX1, and CYP3A4 to develop designer liver organoid (DesLO) tissue. Full details are included in methods. (B) Gene expression of ATF5 and PROX1 in DesLO tissues versus transduction control FeLO (n=3-8). (C) Synergistic effect for CYP3A4 activation observed when CYP3A4 gRNA/dCas9 ('CYP3A4') transduced in tandem with ATF5 and PROX1 ('A+P'). Significance relative to CYP3A4 gRNA/dCas9 only transduction. Multiplicity of infection (MOI) of all transductions is 9. **p<0.0001, (n=3-8). (D) CYP3A4 enzymatic activity observed when CYP3A4 gRNA/dCas9 ('CYP3A4') transduced in tandem with ATF5 and PROX1 ('A+P') compared with FeLO and CYP3A4 gRNA/dCas9 only transduced tissues. Significance relative to CYP3A4 gRNA/dCas9 only transduction. MOI of all transductions is 9. **p<0.0001, (n=3). (E) Heatmap of gene expression in FeLO and DesLO from RNA sequencing data highlighting increased DesLO expression of important liver genes (n=2). (F) Heatmap of gene expression in FeLO and DesLO from RNA sequencing data highlighting decreased DesLO expression of aberrant lineages (n=2). (G) Heatmap showing the CellNet GRN scores for the listed tissues or cell types for Day 17 FeLO and DesLO. DesLO has increased liver and decreased fibroblast GRN scores relative to FeLO (n=2). (H) Heatmap showing the Keygenes scores for the listed tissues or cell types for Day 17 FeLO, DesLO, and pAAT ATF5 DesLO. DesLO has increased liver and decreased intestine scores relative to FeLO (n=2). (I) Heatmap showing the trimester 1 (T1) Keygenes scores for the listed tissues or cell types for FeLO and DesLO. DesLO has increased liver and decreased stomach and heart scores FeLO (n=2). (J) Heatmap showing the trimester 2 (T2) Keygenes scores for the listed tissues or cell types for FeLO and DesLO. DesLO shows high identity with T2 and shows increased liver identity compared to FeLO (n=2). (K) Heatmap showing the adult Keygenes scores for the listed tissues or cell types for FeLO and DesLO. DesLO shows the highest identity with adult liver whereas FeLO shows highest score for adult intestine (n=2).

In such cases, the CRISPR cassettes are configured to activate endogenous CYP3A4 locus in liver organoids. Referring to FIGS. 4A-4D, such CRISPR cassettes boost expression of CYP3A4 by at least 500 fold and up to about 1500 fold (FIG. 4C). The cassettes also increased activity of CYP3A4 protein in the organoids (FIG. 4D). Increasing CRISPR dosage further increased expression and CYP3A4 protein activity. In some cases, cell type specific promoters (e.g., hepatocyte specific promoter pAAT) can be used to spatially limit CRISPR activity to particular cell types (e.g., hepatocytes). In other cases, CRISPR cassettes are configured to activate endogenous expression of other CYP enzymes such as CYP1A2, CYP2B6, CYP2C9, and CYP2C19.

Hepatocyte immaturity is classically defined by the limited amount of urea and albumin production, a low level of Cytochrome p450 activity (i.e., CYP3A4) and/or by inferior inducibilty in response to drugs compared to adult counterparts. Any appropriate assay for detecting and measuring a change in cytochrome P450 activity can be used to study cells following CRISPR-based gene editing. In general, the physiological functionality of cultured hepatocytes is assessed by measuring the activity of one or more of five key CYP enzymes: CYP1A2, CYP2B6, CYP2C9, CYP2C19, and CYP3A4. These five key CYPs are major phase I enzymes that account for 60% of human drug oxidation. To examine drug metabolizing enzyme activities, luminescence-based assays for CYP3A4 (luciferin-IPA), CYPs 1A1, 1A2, 2B6, and 2D6 (luciferin-ME-EGE) and CYP2C9 (luciferin-H) can be performed. In some cases, a commercially available kit for assessing CYP3A4 activity in modified human hepatocytes, such as a P450-Glo CYP3A4 Assay from Promega (Madison, WI, USA), can be used. Images can be collected to investigate vascular formation and the number of non-parenchymal cells (e.g., $Desmin^+$ cells). In some cases, immunofluorescence staining and imaging is followed by image analysis using a software program such as CellProfiler/Analyst.

In some cases, CRISPR cassettes comprise a constitutively active promoter such as hEF1a, PGK, or CAG promoters. In other cases, promoters on the synthetic regulatory circuit are replaced with a cell type specific promoter. For example, a synthetic RNA Pol II or Pol III promoter can be swapped with a cell type- or context-specific promoter. A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

The terms "Cas9 molecule" or "Cas9 polypeptide", as used herein, refer to a polypeptide that can bind (1) a PAM (a pro to spacer adjacent motif) in a nucleic acid, and (2) a guide RNA (gRNA) molecule. In an embodiment, in concert with the gRNA molecule, a Cas9 molecule or Cas9 polypeptide can localize to a site which comprises a target domain. Cas9 may be a nuclease (an enzyme that cleaves both strands of a double-stranded nucleic acid), a nickase (an enzyme that cleaves one strand of a double-stranded nucleic acid), or an enzymatically inactive (or dead) molecule. In some cases, the Cas9 molecule is an altered, engineered, or modified Cas9 molecule. As used herein, the terms altered, engineered, or modified refers merely to a difference from a reference or naturally occurring sequence, and impose no specific process or origin limitations.

"Domain", as used herein, is used to describe segments of a protein or nucleic acid. Unless otherwise indicated, a domain is not required to have any specific functional property.

CRISPR systems belong to different classes, with different repeat patterns, sets of genes, and species ranges. A CRISPR enzyme is typically a type I or III CRISPR enzyme. The CRISPR system is derived advantageously from a type II CRISPR system. The type II CRISPR enzyme may be any Cas enzyme. The terms "Cas" and "CRISPR-associated Cas" are used interchangeably herein. The Cas enzyme can be any naturally-occurring nuclease as well as any chimeras, mutants, homologs, or orthologs. In some embodiments, one or more elements of a CRISPR system is derived from a particular organism comprising an endogenous CRISPR system, such as *Streptococcus pyogenes* (SP) CRISPR systems or *Staphylococcus aureus* (SA) CRISPR systems. The CRISPR system is a type II CRISPR system and the Cas enzyme is Cas9 or a catalytically inactive Cas9 (dCas9). Other non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1. Csb2, Csb3, Csx17, Csx14, Csx10, Csx16, CsaX, Csx3, Csx1, Csx15, Csf1, Csf2, Csf3, Csf4, homologues thereof, or modified versions thereof. A comprehensive review of the Cas protein family is presented in Haft et al. (2005) Computational Biology, PLOS Comput. Biol. 1: e60. At least 41 CRISPR-associated (Cas) gene families have been described to date.

It will be understood that the CRISPR-Cas system as described herein is non-naturally occurring in a cell, i.e. engineered or exogenous to the cell. The CRISPR-Cas system as referred to herein has been introduced in a cell. Methods for introducing the CRISPR-Cas system in a cell are known in the art, and are further described herein elsewhere. The cell comprising the CRISPR-Cas system, or having the CRISPR-Cas system introduced, comprises or is capable of expressing the individual components of the CRISPR-Cas system to establish a functional CRISPR complex, capable of modifying (such as cleaving) a target DNA sequence. Accordingly, as referred to herein, the cell comprising the CRISPR-Cas system can be a cell comprising the individual components of the CRISPR-Cas system to establish a functional CRISPR complex, capable of modifying (such as cleaving) a target DNA sequence. Alternatively, as referred to herein, and preferably, the cell comprising the CRISPR-Cas system can be a cell comprising one or more nucleic acid molecule encoding the individual components of the CRISPR-Cas system, which can be expressed in the cell to establish a functional CRISPR complex, capable of modifying (such as cleaving) a target DNA sequence Components of any of the synthetic regulatory circuits described herein are preferably provided in a single amplicon. In some cases, however, the components may be in the form of two or more polynucleotide sequences. The synthetic regulatory circuit can be an engineered polynucleotide. As used herein, the terms "engineered nucleic acid" and "engineered polynucleotide" are used interchangeably and refer to a nucleic acid that has been designed and made using known in vitro techniques in the art. In some embodiments, an engineered polynucleotide, also referred to as a circuit herein, is a nucleic acid that is not isolated from the genome of an organism. In some embodiments, the engineered polynucleotide is introduced to a cell, plurality of cells, an organ or an organism to perform diverse functions (e.g., differentiation of cells, as sensors within cells, program a cell to act as a sensor, and delivery of selective cell-based therapies).

In some cases, components of any of the synthetic regulatory circuits described herein are provided in a single amplicon that is packaged in a delivery vector for introduction into a cell (e.g., a mammalian cell). Any appropriate delivery vector can be used with the systems and methods described herein. For example, delivery vectors include exosomes, viruses (viral vectors), and viral particles. Preferably, the delivery vector is a viral vector, such as a lenti- or baculo- or preferably adeno-viral/adeno-associated viral (AAV) vectors, but other means of delivery are known (such as exosomes, yeast systems, microvesicles, gene guns/ means of attaching vectors to gold nanoparticles) and are provided. For example, an amplicon comprising circuit components as described herein can be delivered/introduced into a cell via liposomes, nanoparticles, exosomes, microvesicles, or a gene-gun. In certain preferred embodiments, the circuit components are packaged in an amplicon for delivery to a cell in one or more viral delivery vectors. Suitable viral delivery vectors include, without limitation, adeno-viral/ adeno-associated viral (AAV) vectors, lentiviral vectors, and Herpes Simplex Virus 1 (HSV-1) vectors.

In some cases, the inducible transgene is inducible by doxycycline (e.g., a doxycycline-inducible GATA6 transgene, a doxycycline-inducible ATF5 transgene, a doxycycline-inducible PROX1 transgene).

In some cases, a mature liver organoid (or "DesLOs") is produced by inducing expression of a Gata6 transcription factor in cells of a fetal liver organoid for about five days, depletion of aberrant cell types (those expressing TRA-1-60 or other pluripotent stem cells markers) on or after day 3, and delivery of CRISPR transcriptional activators specific for CYP3A4 or another Cyp or other drug metabolizing enzymes and at least one other transcription factor (for example, ATF5, prox1, MLXIPL1, and/or CREB3L3). As demonstrated in the Examples, overexpression of a subset of these transcription factors can globally advance tissue phenotype towards adult liver-like identity ex vivo. By initiating maturation of liver organoids in vitro in just a few days, the methods and compositions provided herein decreasing the cost and time associated with mature liver organoid preparation and eliminate the need for in vivo transplantation for maturation.

In preferred embodiments, fetal liver organoids used for the methods described herein are prepared by directing in vitro differentiation of human progenitor cell types such as human pluripotent stem cells. Heterogeneous GATA6 expression can be genetically engineered in human induced pluripotent cells (hiPSCs) through lentivirally transducing of an inducible GATA6 cassette. When cultured in the presence of doxycycline (DOX) in a culture medium comprising bFGF and TGF-β (e.g., mTeSR medium) and, optionally, a Rho kinase (ROCK) inhibitor (e.g., Y-27632) for about 5 days, the transfected cells differentiate into endodermal and mesodermal progenitors. Following the five-day induction of GATA6 in pluripotency medium by addition of doxycycline, the progenitor cells co-differentiate and self-organize sequentially into vascularized fetal liver tissue in vitro without supplementation of any growth factor, thus forming a complex, fetal liver-like tissue organoid. See also Guye et al. (Genetically engineering self-organization of human pluripotent stem cells into a liver bud-like tissue using Gata6. Nat Commun, 7:10243 (2016)), which is incorporated herein in its entirety. The fetal liver organoid contains hepatoblasts, desmin+ stellate-like cells and CD34+ hemogenic endothelium. Within about two weeks, CD34+ endothelial tubes constrict and generate small spherical cells expressing CD45 or hemoglobin gamma, supportive of definitive fetal erythropoiesis. The resulting fetal liver organoid is a vascularized liver-like tissue comprising CEBP-$\alpha^+$/AAT$^+$ hepatoblasts, CK19$^+$/CK7$^+$ cholangiocytes, CD34$^+$ endothelium, and Desmin stellate (-like) cells with hematopoiesis-like processes. Accordingly, GATA6-derived liver organoids provide a multicellular human tissue that closely mimics key features of the fetal liver such as several subsets of stromal cells, endothelial cells, and vital cell signaling cues in a 3D configuration.

In some cases, pluripotent stem cells (e.g., hiPSCs) used to produce a fetal liver organoid or mature liver organoid as described herein are cultured in a chemically defined medium comprising a Rho Kinase (ROCK) inhibitor for about 1 day (about 24 hours) prior to start of a differentiation protocol as provided herein. In some cases, the chemically defined medium is mTeSR-1 and the ROCK inhibitor is Y-27632. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino) ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl) homopiperazine dihydrochloride (informal name: glycyl H-1152) and (+)-(R)-trans-4-(1-aminoethyl)-N-(4-pyridyl) cyclohexanecarboxamide dihydrochloride (informal name: Y-27632). Kinase inhibitors, such as ROCK inhibitors, are known to protect single cells and small aggregates of cells, including pluripotent stem cells. The kinase inhibitor can be provided at a concentration sufficiently high that the cells survive and remain attached to the surface. An inhibitor concentration between about 3 μM to about 10 μM can be suitable. At lower concentrations, or when no ROCK inhibitor is provided, undifferentiated cells typically detach, while differentiated cells remain attached to the defined surface.

It will be advantageous in some cases to use one or more cell types derived from a particular mammalian subject (e.g., a particular human subject). In such cases, the cells may exhibit one or more specific phenotypes associated with or resulting from a particular disease or disorder of the particular mammalian subject. Subject-specific cells can be obtained or isolated from a target tissue of interest by biopsy or other tissue sampling methods. In some cases, subject-specific cells are manipulated in vitro prior to use in a liver organoid of this disclosure. For example, subject-specific cells can be expanded, differentiated, genetically modified, contacted to polypeptides, nucleic acids, or other factors, cryopreserved, or otherwise modified prior to use in a liver organoid of this disclosure. In some cases, it will be advantageous to use cells derived from iPS cells obtained from individuals having known susceptibilities or resistances to various drugs or diseases for liver organoids of the disclosure. In such cases, liver organoids comprising subject-specific cells can be used to identify genetic factors and epigenetic influences that contribute to variable responses.

In some cases, the pluripotent stem cells are subject-specific pluripotent stem cells (e.g., human induced pluripotent stem cells) obtained by reprogramming somatic cells of the subject according to methods known in the art. Human induced pluripotent stem cells (hiPSCs) allow modeling and study of the responses of cells and tissues to drugs, chemicals, or toxins in a genetically diverse population of individuals, including those individuals with genetic diseases.

In some cases, one or more additional genetic modifications are introduced into liver parenchymal cells (e.g., hepatocytes) and/or one or more types of liver non-parenchymal cells (e.g., Kupffer cells, hepatic stellate cells, sinusoidal endothelial cells, myofibroblasts) of a mature liver organoid of this disclosure.

Although human cells are preferred for use in liver organoids of this disclosure, the cells are not to be limited to cells from human sources. Cells from other mammalian species including, but not limited to, equine, canine, porcine, bovine, feline, caprine, murine, and ovine sources can be used. Cell donors may vary in development and age. Cells can be derived from donor tissues of embryos, neonates, or older individuals including adults.

In some cases, a mature liver organoid is produced in any appropriate cell culture substrate such as a tissue culture dish. In some cases, substrate is coated (partially or fully) with a defined extracellular matrix protein substrate or undefined extracellular matrix protein substrate such as Matrigel®. In other embodiments, the cell culture substrate is coated in material devoid of xenogeneic (e.g., non-human animal-derived) components. Such materials include, but are not limited to, vitronectin, a vitronectin fragment, a vitronectin peptide, and self-coating substrates such as Synthemax® (Corning). Other materials include, without limitation, collagen, fibronectin, laminin, Arg-Gly-Asp (RGD) peptide, Tyr-Ile-Gly-Ser-Arg (YIGSR; SEQ ID NO: 1) peptide, glycosaminoglycans (GAGs), hyaluronic acid (HA), integrins, ICAMs, selectins, cadherins, and cell surface protein-specific antibodies.

Any appropriate method can be used to detect expression of biological markers characteristic of mature liver cell types. For example, the presence or absence of one or more biological markers can be detected using, for example, RNA sequencing, immunohistochemistry, polymerase chain reaction, qRT-PCR, or other technique that detects or measures gene expression. Suitable methods for evaluating the above-markers are well known in the art and include, e.g., qRT-PCR, RNA-sequencing, and the like for evaluating gene expression at the RNA level. Quantitative methods for evaluating expression of markers at the protein level in cell populations are also known in the art. For example, flow cytometry is typically used to determine the fraction of cells in a given cell population that express (or do not express) a protein marker of interest (e.g., hepatocyte expression of albumin). As illustrated in FIG. 1 and demonstrated in the Examples section, maturation of cells in a fetal liver organoid to a mature liver organoid can be confirmed based on the absence of "immature" liver cell types (e.g., hepatoblasts) and the presence of mature liver cell types (e.g., functional hepatocytes), augmented (improved) vascularity relative to the fetal liver organoid, FxR signaling, and fibrogenesis. Differentiated cell identity is also associated with downregulation of pluripotency markers such as TRA-1-60, NANOG, and OCT4 (relative to undifferentiated human ES cells or induced pluripotent stem cells).

III. Methods of Using Compositions

Compositions comprising a mature in vitro-engineered liver tissue or "DesLO" as provided herein are suitable for use in variety of practical applications. For example, DeLOs can be designed to comprise complex tissue phenotypes, such as idiosyncratic drug toxicity, inflammation, and fibrosis. Due to the flexibility in modifying their gene expression, DesLOs also are useful for advancing drug metabolisms to capturing the toxicity effects of the drug. Accordingly, DesLOs of this disclosure are particularly useful for disease modeling applications and for drug discovery and drug toxicity screening applications.

In another aspect, mature in vitro-engineered liver tissues or "DesLOs" are useful for modeling cellular and molecular interactions involved in maturation of fetal tissues. In particular, organoids of this disclosure are well suited to study the effects of modulating gene expression, modulating expression of various transcription factors, and/or modulating expression or function of drug metabolizing enzymes on maturation of liver tissue and the generation of an adult-like human liver model. For example, mature in vitro-engineered liver tissues are useful to study the effects of genetic mutations on development and function of the human liver, to conduct personalized studies using cells derived from induced pluripotent stem cells (iPS cells) of a particular human subject, and to assess toxicity of various agents or other effects on human liver development. In some cases, mature in vitro-engineered liver tissues are useful in drug discovery and development including screening for metabolic stability, drug-drug interactions, toxicity and infectious disease. Exemplary test agents include, without limitation, infectious agents, proteins, peptides, antibodies, small molecules, oligonucleotides, polynucleotides, peptidomimetics, cytotoxic agents, pharmaceutical agents, and xenobiotics (e.g., environmental toxin, chemical/biological warfare agent, a natural compound, and a nutraceutical).

In some cases, mature liver organoids prepared according to the methods provided herein can be screened to identify agents that modulate human liver development. Screening methods can comprise or consist essentially of (a) contacting a test agent to one or more in vitro-derived mature liver organoids; and (b) detecting an effect of the agent on the mature liver organoid or cells derived therefrom (e.g., disrupt or otherwise alter development of the liver-specific cells or liver-specific functionality). In some embodiments, detecting and/or measuring a positive or negative change in a level of expression of at least one gene following exposure (e.g., contacting) of a test compound to a mature liver organoid comprises whole transcriptome analysis using, for example, RNA sequencing. In such cases, gene expression is calculated using, for example, data processing software programs such as Light Cycle, RSEM (RNA-Seq by Expectation-Maximization), Excel, and Prism. See Stewart et al., PLOS Comput. Biol. 9: e1002936 (2013). Where appropriate, statistical comparisons can be made using ANOVA analyses, analysis of variance with Bonferroni correction, or two-tailed Student's 1-test, where values are determined to be significant at $P<0.05$. Any appropriate method can be used to isolate RNA or protein from a mature liver organoid. For example, total RNA can be isolated and reverse transcribed to obtain cDNA for sequencing.

Test compounds can be dissolved in a solvent such as, for example, dimethyl sulfoxide (DMSO) prior to contacting to a mature liver organoid provided herein. In some cases, identifying agents comprises analyzing the contacted mature liver organoid for positive or negative changes in biological activities including, without limitation, gene expression, protein expression, cell viability, and cell proliferation. For example, microarray methods can be used to analyze gene expression profiles prior to, during, or following contacting the plurality of test compounds to the mature liver organoid. In some cases, the method further comprises additional analyses such as metabolic assays and protein expression profiling.

In some embodiments, a mature in vitro-engineered liver tissue composition (e.g., DesLO composition) of this disclosure is used as a model of fibrogenic disease, active bile sensing, the ability of tissues to metabolize drugs and Farnesoid X receptor (FXR) agonists, or liver injury.

In some embodiments, a computational biology platform based on machine learning algorithms such as CellNet is applied to a mature in vitro-engineered liver tissue composition (e.g., DesLO composition) of this disclosure in order to identify differentially expressed genes under various conditions. For example, a computational platform can be used to identify subject-specific gene expression differences associated with particular liver diseases or disorders relative to a healthy liver control. In such cases, cells of the liver organoid can be derived from subject-specific induced pluripotent stem cells, in some cases obtained from a human subject known to have a particular liver disease or disorder.

In some embodiments, it will be advantageous to combine a computational biology platform based on machine learning algorithms (e.g., CellNet) with modulation of organoids' endogenous gene regulatory networks (GRNs) to genetically control and redirect cell and tissue formation towards advanced developmental stages ex vivo. For example, in some cases, differentially expressed genes identified using a computational biology platform such as CellNet are identified as transcriptional modulators that can be spatiotemporally controlled using CRISPR-based techniques in iPSC-derived multicellular liver tissues as described herein. Machine learning algorithms such as CellNet take as input RNA-Seq or microarray expression data from engineered cells or tissue organoids (e.g., a liver organoid). It returns cell and tissue type classifications, GRN statuses, and list of transcription factor candidates whose modulation is predicted to improve the classification of the engineered population.

In some cases, RNA-Seq data obtained from a DesLO of this disclosure is used to develop a liver maturation stage CellNet as a tool for assessing the maturation stage of other liver organoids and to identify novel transcriptional regulators whose modulation will improve maturation. In other cases, RNA-Seq data from a variety of organoids and cell lineages is used to develop a general maturation CellNet which will provide insights into lineage-specific vs. general mechanisms that contribute to tissue maturation.

In some cases, the methods of this disclosure comprise combining such machine learning algorithms (e.g., CellNet) with the methods of directing maturate liver organoid formation to provide a platform for development of a set of gene regulatory tools such as CRISPR-based gene regulators to identify additional genes and signaling pathways important for liver development and liver function. Such platforms can be used to direct or modulate development of in vitro-derived liver organoids in a particular manner to elucidate aspects of liver development including development of augmented vasculature or liver function.

In another aspect, provided herein is a method for using a mature liver organoid obtained according to the methods of this disclosure for transplantation into a living animal. In particular, the methods comprise transplanting a synthetic mature organoid into a living animal (e.g., a mammal) for in vivo development of functional liver tissue. As described in the Examples, in vivo implantation of a mature liver organoid promotes development of functional liver tissue and offers protection to the host mammal from liver failure. Accordingly, this disclosure provides for therapeutic uses of synthetic mature liver organoids to promote production of healthy, functional liver tissue that can protect the mammal receiving the transplanted material from liver failure.

IV. Articles of Manufacture

In another aspect, provided herein is a kit comprising one or more components useful for obtaining a mature liver organoid or a fetal liver organoid. Components of the kit can include one or more lentiviral constructs and/or CRISPR cassettes as described herein. The kit can also contain a chemically defined culture medium and one or more medium additives. In another aspect, provided herein is a kit comprising one or more components useful to prepare a multicellular mature liver organoid or a fetal liver organoid according to the methods provided herein. Components of the kit can include one or more lentiviral constructs and/or CRISPR cassettes as described herein.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The following experimental examples are not intended to be limiting, and relate to compositions and methods for modulating liver organoid composition using CRISPR-based transcriptional modulators that can be spatiotemporally controlled in iPSC-derived multicellular tissues.

CRISPR-based Transcriptional Modulation for Ex vivo Cell Fate Interrogation in Liver Organoids Organoids-complex, self-organized tissue with organ-specific cell types- are increasingly being developed for disease modeling, drug discovery, and therapeutic applications. Vital to this endeavor is the generation of a toolbox for robust manipulation of gene regulatory networks in organoids ex vivo. Such technology will enable generation of designer tissues and steering developmental stages of organoids towards adult phenotypes. Clustered regularly interspaced palindromic repeats (CRISPR) technology has advanced rapidly, providing a powerful method for cell fate engineering. We hypothesized that CRISPR-based epigenome editing can provide opportunity to control and engineer cell fate and function in a complex tissue microenvironment.

We analyzed several components of the system including identity of target gene, location of sgRNA target sites, quantity of sgRNAs delivered, mass of dCas9/gRNA plasmid transfected, transfection vs. transduction, temporal kinetics of activation, and the Synergistic Activation Mediator (SAM) versus the VP64-p65-Rta (VPR) activation domain. Gene expression was assessed using quantitative real time PCR. We transiently transfected human embryonic kidney (HEK) cells or used lentiviral delivery in human liver organoids. Increased expression was achieved for all genes tested, but certain genes could be induced much more than others, perhaps due to varying endogenous expression and distinct epigenetic landscapes. We could stably engineer organoids with the CRISPR system using lentiviral delivery at different time points over a course of at least 20 days. We showed transcriptional remodeling of the Cyp3a4 locus to an active state and metabolism of Cyp3a4 substrates. These data demonstrate that CRISPR-based transcriptional modulation can be employed to genetically modulate specific sets of genes within multicellular complex tissue microenvironments developed from human stem cells (iPSCs). It allows for engineering control over cell fate, developmental stage determination, and global tissue function.

Figures 2A, 2B, 2C, 2D, 2E, 2F, 2G, 2H:
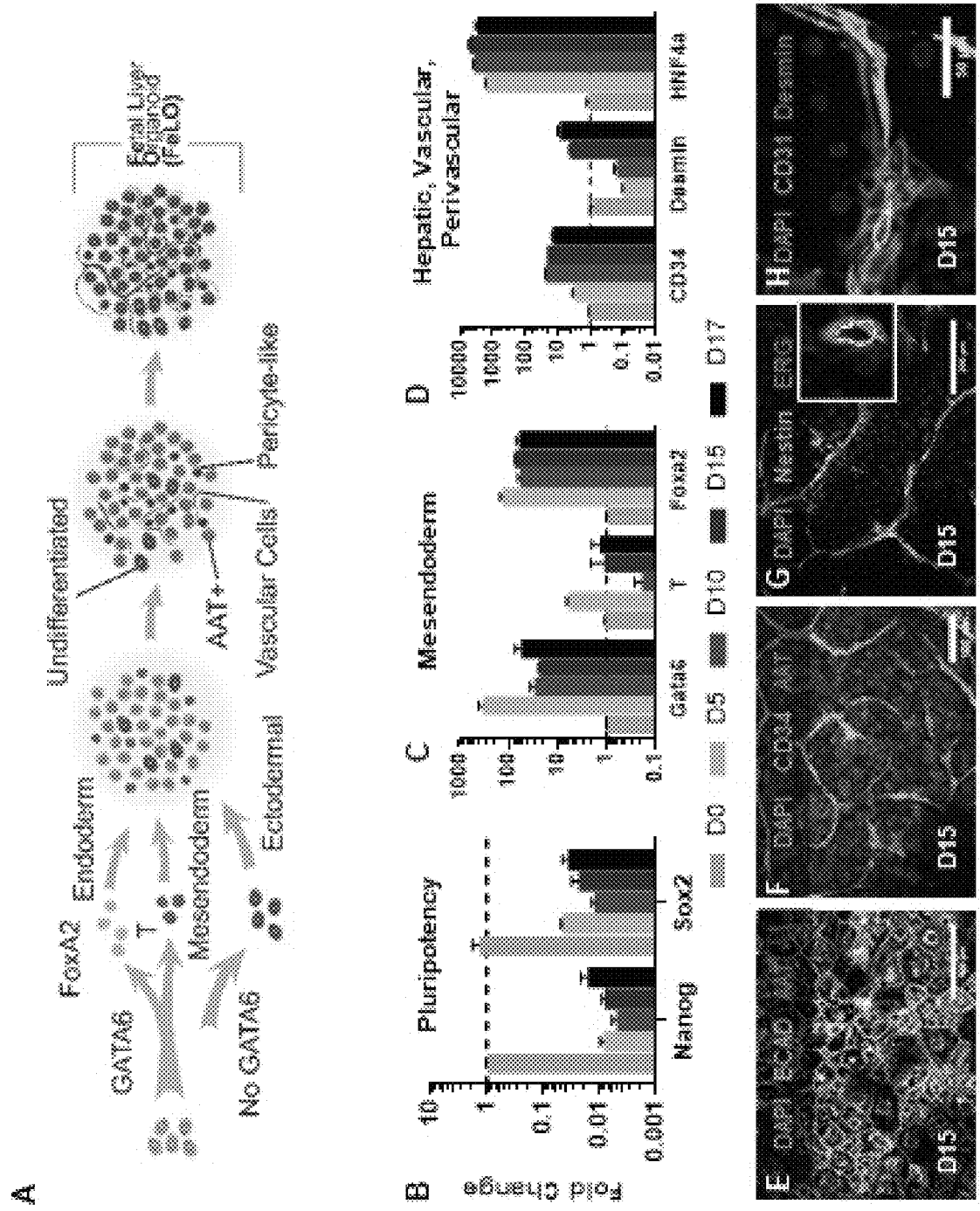
FIGS. 2A-2M demonstrates generation and characterization of Fetal Liver Organoids (FeLO) from GATA6 engineered human induced pluripotent stem cells (hiPSC). (A) Full culture details are listed in the Materials and Methods section. Cultures induced with doxycycline contribute to the formation of all three germ layers, but predominantly endoderm and mesoderm lineages represented by FOXA2 and T. Cultures develop into fetal liver organoids containing hepatocyte-like, endothelial, and pericytes like cells. (B-D) Real time qPCR data of decreasing pluripotency markers NANOG and SOX2 (B), initial increase of early mesendoderm markers GATA6, T, and FOXA2 (C), and increase of endothelial (CD34), stromal (Desmin), and hepatic (HNF4A) transcripts (D). All samples are referenced against the D0 (day 0) uninduced control. (n=3 except n=2 for DO). (E-H) FeLO cultures stained at day 15 show hepatocyte-like E-cadherin (ECAD) tight junctions and AAT expression (E), CD34+ endothelial-like cells (F), and pericyte-endothelial associations of Nestin+ and ERG+ cells (G) and Desmin+ and CD31+ cells (H), highlighting multiple germ layer development and multicellular compartments of FeLO cultures. (I) Concentration of liver secreted protein albumin in the culture medium on days 5, 10, 15, and 17 of FeLO culture. (n=3). (J) Concentration of albumin secreted into the medium by FeLO (day 17) and primary human hepatocyte (PHH) cultures (3 days in culture), normalized by number of hepatic cells. For FeLO, this is by number of HNF4A+ cells counted on day 17, and for PHH this is by number of cell seeded (primary hepatocytes do not proliferate in 2D culture). (n=3). (K) EnrichR-generated D17 FeLO upregulated genes (qualified by >2 fold change over DO) indicate associated KEGG pathways. The most represented pathways, as well as some selected significant pathways related to liver and fetal liver have been included. (L) Heatmap showing the CellNet GRN scores of fetal liver organoids (FeLO) in listed tissues or cell types before induction of Gata6 (Day 0) and at Day 5, 10, and 17 of culture, indicating highest scoring for ESC at days 0 and 5, but highest scores for liver on days 10 and 17. (n=2). (M) Liver GRN Network influence score analysis using CellNet reveals the transcriptional regulators that show deficiency in our D17 FeLO tissue compared to primary human liver. ATF5 and PROX1 are indicated by red arrows. (n=2).

In another set of experiments, we took advantage of a strategy we described recently where FeLOs are developed from hiPSCs in vitro using transient and heterogeneous lentiviral expression of GATA6 in defined culture media (Guye et al., 2016). To refine transgene expression with high and stable integration rate and minimal toxicity, we tested a Piggybac transposition approach. Following transient GATA6 induction by addition of doxycycline in pluripotent medium, we established emergence of endodermal (FoxA2$^+$) and mesodermal (Brachyury(T)$^+$) progenitors (FIGS. 3A-3D). In the course of ~15 days cells co-differentiate and self-organize into a complex tissue that resembles human fetal liver containing cells from three germ layers as previously shown (Guye et al., Nat Commun, 7:10243 (2016)) (FIG. 2A).

Figures 2I, 2J, 2K, 2L, 2M:
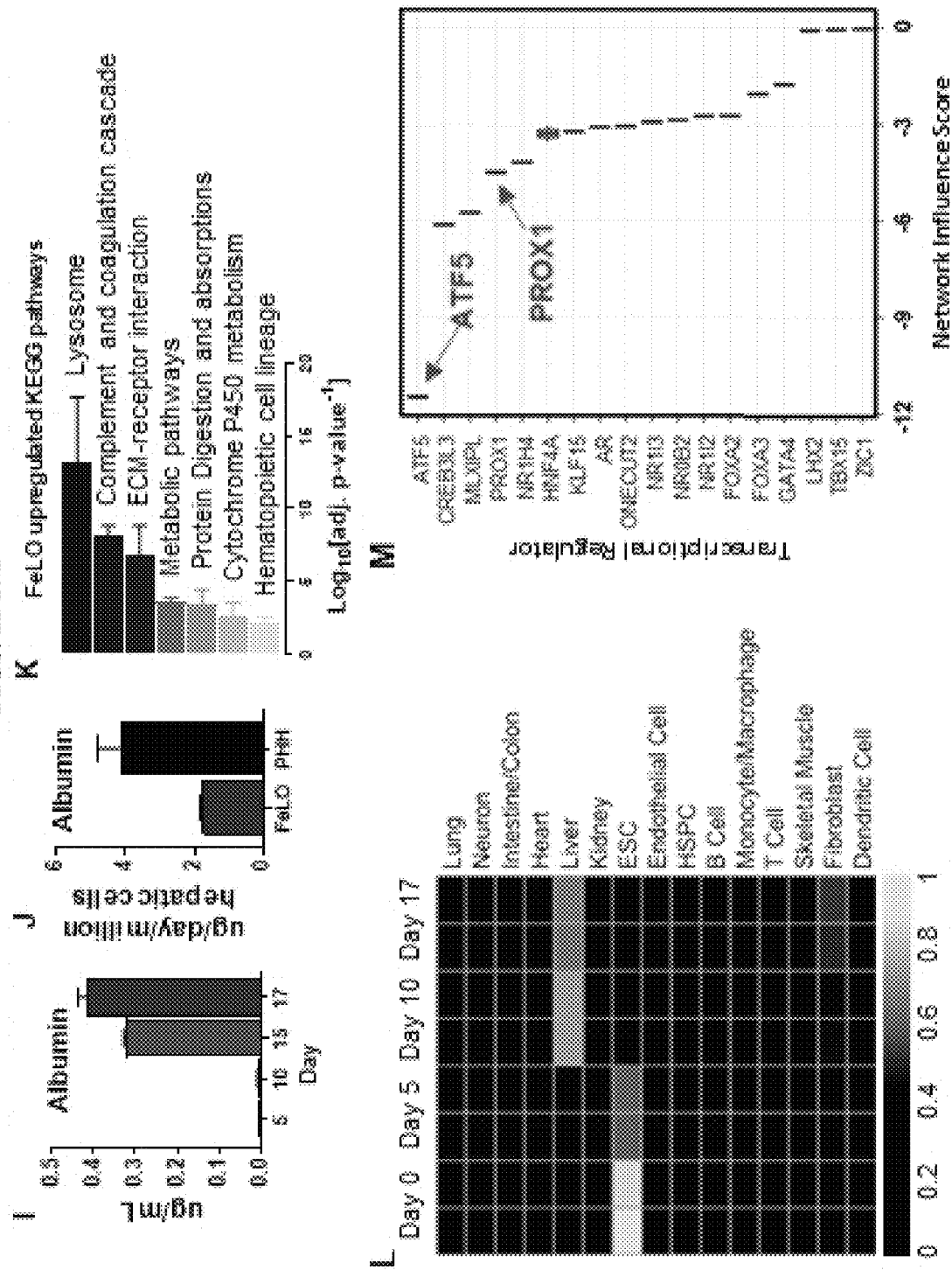

Quantitative PCR analyses accompanied by immunofluorescence staining show downregulation of pluripotency markers NANOG and SOX2, followed by upregulation of mesoderm (T) and endoderm markers (FoxA2) during the initial 5 days (FIGS. 2B-2C, 3A-3D). Markers associated with hepatic, vascular and stromal cell types increase after day 5 (FIG. 2D), suggesting steady differentiation towards complex multicellular liver identity. Immunofluorescence staining analyses on day 15 show hexagonal AAT+ hepatocyte-like cells with E-cadherin expression at cell-cell junctions, hallmark of epithelial morphology (FIGS. 2E, 2F). A network of CD34+CD31+ endothelial cells forms vascular structures associated with Desmin+ stromal cells that integrates into the hepatic layer by day 15 (FIGS. 2F, 2H). Whole transcriptome time course study of the FeLO cultures on D0, D5, D10, and D17 confirms steady differentiation towards fetal liver identity (FIG. 3E) with minimal upregulation of cytochrome P450 (CYP) 3A4 (a key drug metabolizing liver enzyme) expression by day 17 (D17). Albumin secretion also increased over time, but remained lower than primary hepatocytes on day 17 (FIGS. 2J, 2K). AAT secretion similarly increased and passed the level of primary hepatocytes by day 17 (FIGS. 3F, 3G).

Figures 3A, 3B, 3C, 3D, 3E, 3F, 3G, 3H, 3I, 3J, 3K, 3L:
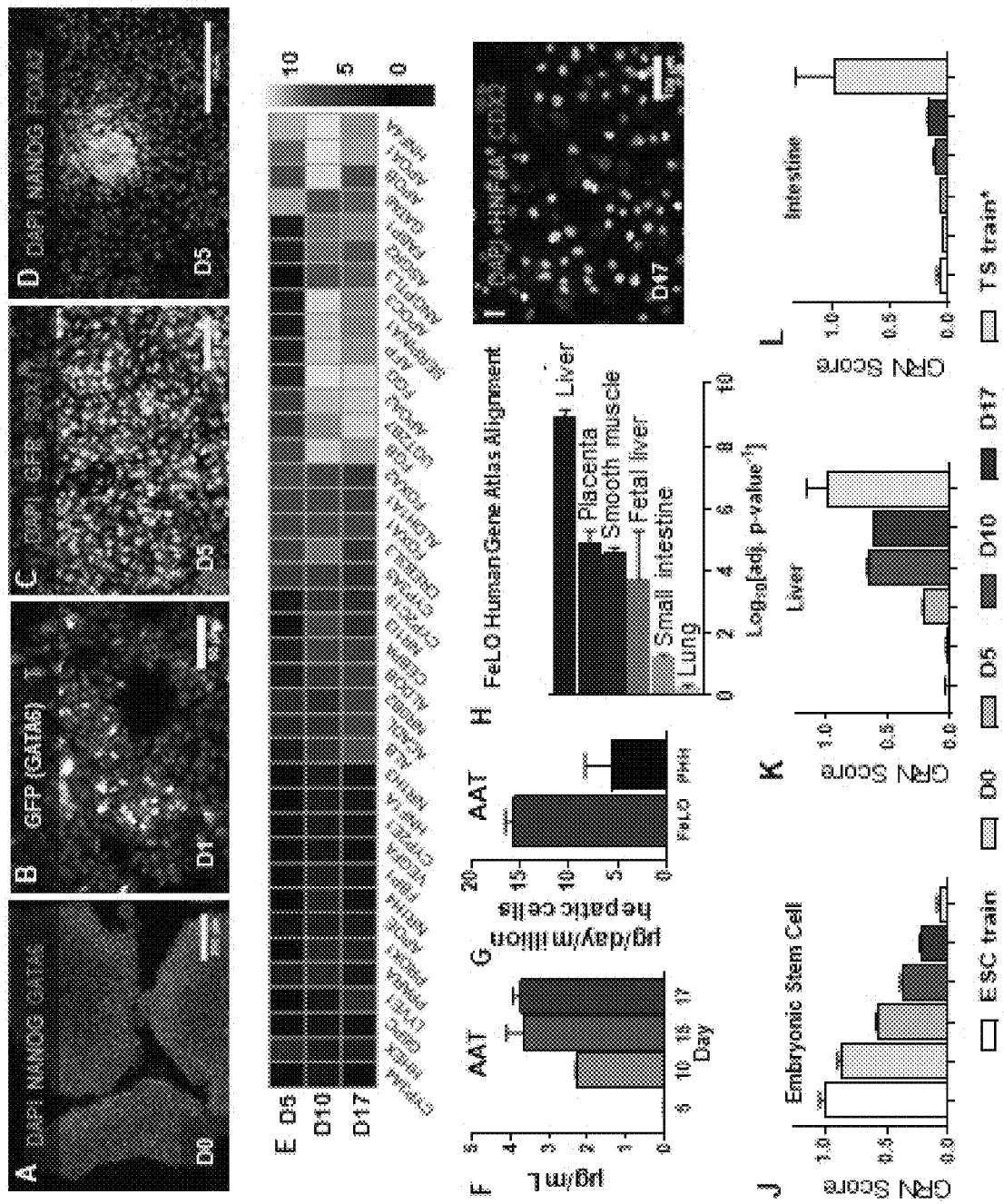
FIGS. 3A-3L. (A-D) Immunofluorescence stains of pluripotency marker NANOG and GATA6 at Day 0 shows no expression of GATA6 prior to induction with dox (A). Mesendodermal markers appear during dox-induced differentiation at Day 1 (B) and Day 5 (C). NANOG and FOXA2 are mutually exclusive (D). (E) Heatmap showing increase in hepatic developmental and functional genes on days 5, 10, and 17. Calculations represent log 2 of the fold change of the indicated aged samples over non-induced cultures (n=2). (F) Concentration of liver secreted protein AAT in the culture medium on days 5, 10, 15, and 17 of FeLO. (n=3). (G) Concentration of AAT secreted into the medium by FeLO (day 17) and PHH cultures (3 days in culture), normalized by number of hepatic cells. For FeLO, this is by number of HNF4A+ cells counted on day 17, and for PHH this is by number of cell seeded (primary hepatocytes to not proliferate in 2D culture) (n=3). (H) EnrichR generated adjusted p-values of D17 FeLO upregulated genes (qualified by >2 fold change over D0) in association with Human Gene Atlas tissue type transcriptome data. The D17 FeLO cultures are most associated with liver identity, but also show significant overlap with Placenta, smooth muscle, and fetal liver tissues. (I) Immunofluorescence stain of Day 17 FeLO show coexpression of liver marker HNF4a and the aberrant intestinal marker CDX2. (J-L) Graphical depiction of the CellNet GRN scores relative to the embryonic stem cell (ESC) (J), liver (K), and intestine (L) training sets maintenance show decreasing ESC, increasing liver, low intestine GRN score in DesLO. Significance relative to FeLO; **p<0.01. (n=2).

Using the web-based gene set enrichment analysis tool, Enrichr, we confirmed the fetal liver identity based on the Human Gene Atlas (FIG. 3H). We detected upregulated KEGG pathways significant for liver function such as complement and coagulation cascades, as well as hematopoietic cell lineage signatures also found in the fetal liver. (FIG. 2L). However, we also detected evidence of aberrant developmental signature such as cells with intestinal marker CDX2 (FIG. 3I). Taken together, we confirm development of multicellular fetal liver-like tissue via GATA6 transposition in hiPSCs. Next, we aimed to devise an approach for rational engineering of FeLO to advance its maturation, cellular composition and tissue identity towards adult liver.

Establishing Spatiotemporally Controlled Transcriptional Modulation

Adult liver is defined by not just one functionality but sets of functional metrics. Therefore, modulation of one gene alone won't be sufficient to reach the true potential of adult liver phenotype. Equally, direct modulation of all genes is not technically feasible. Therefore, we set out to examine whether combinatorial modulation of selected "key" or "global" GRNs can advance fetal liver tissue to adult liver stages. Applying CellNet RNA-Seq data from our liver organoid we found the incomplete establishment of the liver gene regulatory networks (GRN). GRNs define proper lineage commitments in cells, and control behaviors under steady-state as well as environmental perturbations. Algorithms that quantitatively assess GRNs and suggest improvements can be instrumental for rational engineering of morphogenetic events towards adult tissue identity. We previously developed a computational biology platform named CellNet. CellNet uses a machine learning algorithm to develop a training dataset that can present organ specific GRNs. It then analyzes, compares, and ranks tissue identity and the underlying GRNs for query RNA sequencing data. It then identifies key transcription factors amenable for targeting, ranked by Network influence Score (NIS) (i.e., their likelihood to affect a change in GRN), to produce cells that accurately recapitulate their human counterparts.

To quantitatively assess GRNs, we analyzed RNA sequencing data from our uninduced iPSC line (Day 0), and whole FeLO tissue at Day 5, Day 10, and Day 17 of culture. CellNet analysis revealed high GRN scores relative to embryonic stem cells (ESC) for Day 0 and Day 5 samples (FIG. 2L). Liver GRN scores peaked at Day 10 and maintained until D17, emerging as the highest scoring tissue (FIG. 2L, FIG. 3K). ESC GRN scores consistently dropped over the time periods queried (FIG. 3J). While the fibroblast GRN score had also increased slightly by Day 17, other off-target tissues did not display significant changes in GRN score over the culture period (FIG. 2L). CellNet compiled a list of transcription factors for activation to drive FeLO towards a mature liver fate (FIG. 2M). The top five transcription factors have NIS <−4, with activating transcription factor 5 (ATF5) ranked first with a score of almost −12. The other four candidates are CREB3L3, MLXIPL1, Prospero-related homeobox1 (PROX1), and NR1H4 (FXR). ATF5, a member of ATF/cAMP response element binding protein family, is associated with differentiation, survival and maturation of several cell types, including hepatocyte. Similarly, PROX1 is required for hepatocyte migration and endothelial cell development and loss of Prox1 leads to reduced number of hepatocytes and smaller liver. Overexpression of ATF5 and PROX1 has been used to transdifferentiate fibroblasts into functional hepatocytes. These previous findings, in addition to their CellNet Network influence scores, led us to select ATF5 and PROX1 for further genetic reprogramming of FeLOs.

It is commonly considered that a small number of core transcription factors can shape cell identity and control global GRN state (D'Alessio et al., 2015). Manipulation of such factors enables cell fate programming to new cell types with distinct GRN states. This notion has yet to be tested in terms of engineering multicellular systems. Thus, we asked whether engineering a set of genes, selected either by computational analysis or known a priori as important for function of a given organ, can guide maturation of organoids to yield more versatile and useful models for human tissue modeling.

Figures 5A, 5B, 5C, 5D, 5E, 5F, 5G:
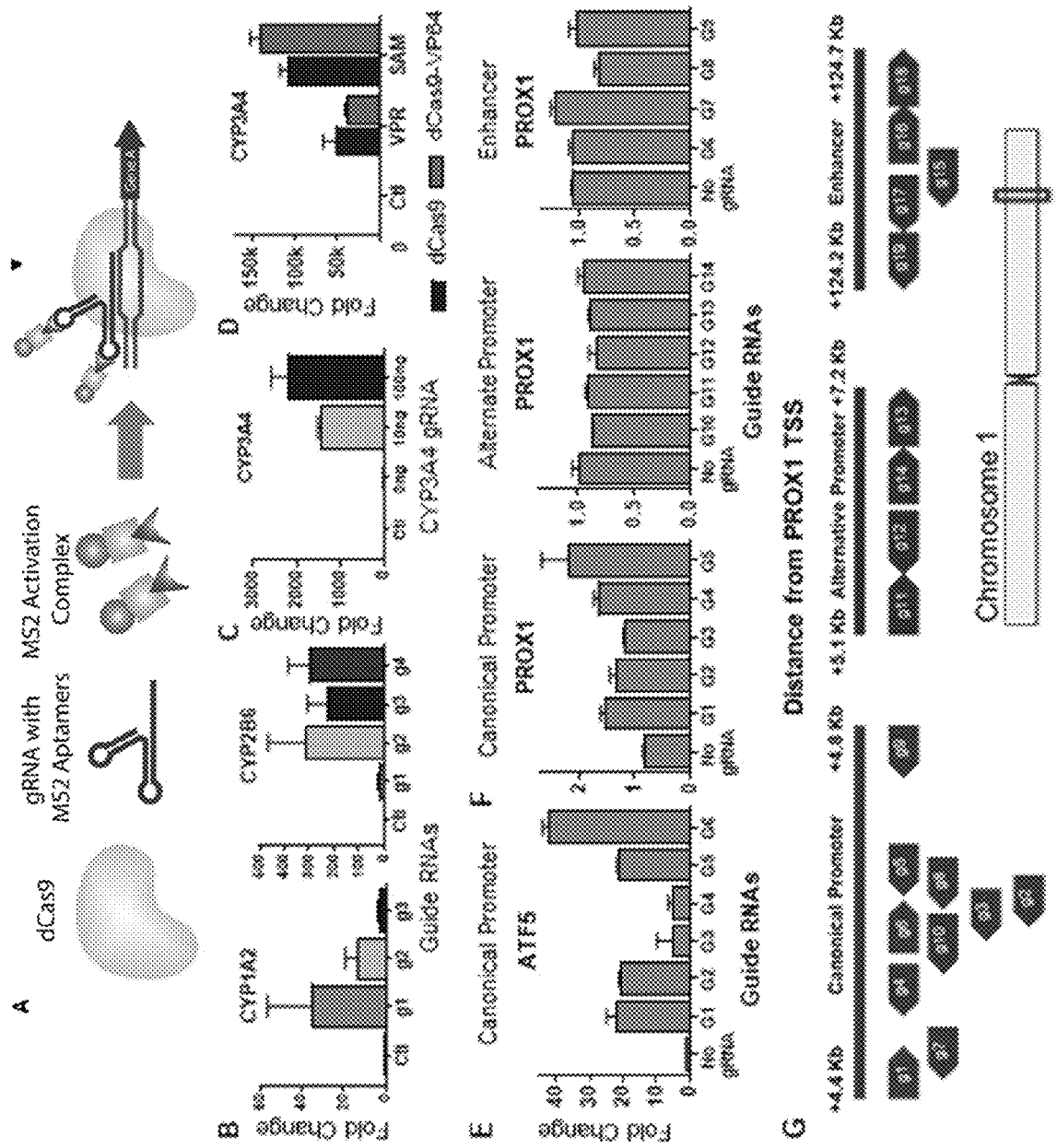
FIGS. 5A-5I. A. Schematic of CRISPRa approach using gRNA containing MS2 aptamers and MS2 fused to transcriptional activators. (B) qPCR data from HEK293FT transfection for screening of sgRNA targeted to CYP1A2 and CYP2B6. Each graph shows the sgRNA screen for the target gene normalized to untransfected HEK293FT (n=2). (C) RT-qPCR data from HEK293FT transfection for screening the effect of mass of sgRNA transfected (either 0, 10, or 100 ng) on CYP3A4 gene activation. Total DNA for transfections were equalized by addition of dummy DNA plasmids. Data are normalized to untransfected HEK293FT. (n=2). (D) RT-qPCR data from HEK293FT transfection for screening the effect of activation complex (either VPR or SAM) and dCas9 variant (either dCas9 or dCas9-VP64) on CYP3A4 gene activation. Total DNA for transfections were equalized by addition. (E) qRT-PCR data for ATF5 gRNA screening in HEK293FT cells targeting the canonical promoter (n=2). (F) qRT-PCR data for PROX1 gRNA screening in HEK293FT cells targeting the canonical promoter, alternative promoter, and enhancer regions (n=2). (G) Schematic showing the PROX1 gRNA target site loci in the canonical promoter, alternative promoter, and enhancer regions on chromosome 1. (H) Schematic showing the CYP3A4 gRNA target site loci in the canonical promoter chosen for upregulation of CYP3A4 on chromosome 7. (I) Fold change in gene expression of CYP3A4, ATF5, and PROX1 when treated with control and gRNA.

We and others have pioneered development of synthetic CRISPR-based epigenetic control that allows for activation of transcription at a target gene (CRISPR) (Chavez et al., 2015; Kiani et al., 2015; Maeder et al., 2013). The CRISPR system has been used in organoids for gene editing (Driehuis and Clevers, 2017; Schwank and Clevers, 2016; Schwank et al., 2013), but its capacity for epigenetic modulation and transcriptional control in a multicellular setting has not been tested. In addition to the CellNet-identified transcription factors, we chose to activate genes imperative for liver function such as cytochrome P450 genes that are upregulated following adult liver development. Specifically, CYP3A4 is a locus that is highly sensitive to environmental stress and its dynamics are key for drug metabolism and detoxification. We employed an approach for screening of different guide RNA (gRNA) target sites predicted by published algorithms that integrate chromatin state, relative position, and other key variables to predict optimal target loci for CRISPR (Horlbeck et al., 2016). We then tested and compared gene activation with different target loci and gRNA delivery amount (FIGS. 5D, 5E). Based on size and high efficacy across loci we decided to utilize an adapted second-generation CRISPR system in which an engineered hairpin aptamer in the gRNA that contains two MS2 domains recruits an MS2-P65-HSF1 transcriptional activation complex (FIG. 5A) (Konermann et al., 2015).

Figures 5H, 5I:
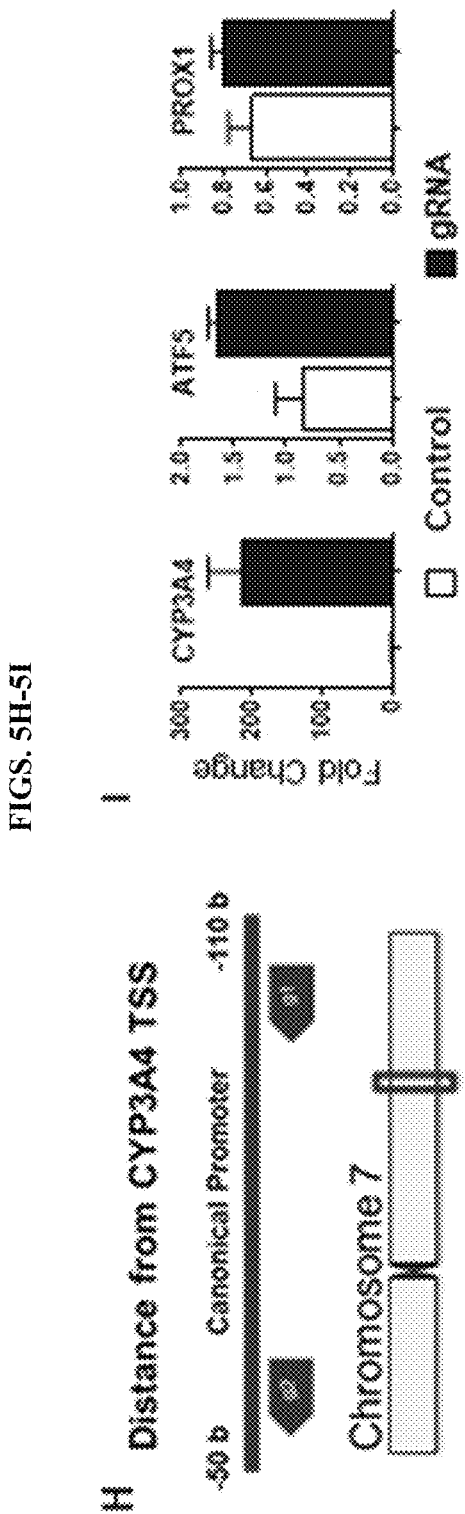

Through these studies we show hepatocyte-related loci are highly permissive to activation in HEK293, a commonly used cell line for CRISPR screens. Among the genes tested we could induce transcriptional activation ranging from 2- to 2000-fold (FIGS. 5D, 5E). We wanted to determine whether CRISPR-mediated transcriptional activation of the endogenous ATF5 and PROX1 loci together with CYP3A4 could develop a FeLO with mature liver GRN. We selected algorithmically determined guides for screening in HEK293 cells (FIGS. 5G, 5H), but observed only modest activation of ATF5 and PROX1 in HEK293 cells, particularly for PROX1 (FIG. 5I). Thus we also attempted to target alternative genetic elements including PROX1 enhancers and non-canonical promoters, however, we did not see further upregulation (FIGS. 5E, 5F) After advancing with the most effective gRNAs tested, we cloned all components into lentiviral vectors for delivery to our tissue on day 5 when hepatic endoderm is developing. While all targets were far less effectively upregulated in the FeLO cultures than in HEK293 cells, increase in CYP3A4 expression remained significant at about 200-fold increased expression (FIG. 5I). However, this translated to a very modest 2-fold increase in measured CYP3A4 enzymatic activity. These experiments suggest that certain genomic structures (i.e., P450 enzymes) may be naturally receptive to epigenetic manipulation and obviate the need for additional parameters controlling dynamics at the ATF5 and PROX1 loci.

Transcription factor overexpression is less dependent to inherent genomic complexity of host cells. Therefore, we decided to increase ATF5 and PROX1 levels via expression of exogenous ATF5 and PROX1 genes. We showed that lentiviral delivery of constitutively active ATF5 and PROX1 transgenes could successfully induce up to 100- and 5-fold changes in expression respectively.

Genetic Engineering Enables Improvement of Hepatic Identity and Tissue Maturation Stage Establishing the ability to genetically manipulate ATF5, PROX1 and endogenous CYP3A4, we next asked whether genetic engineering of ATF5 and PROX1 transcription factors alongside CRISPRa for CYP3A4 can improve FeLO identity. Here we broadly name our rationally-designed, genetically engineered FeLO as Designer Liver Organoids (DesLO) through the rest of this study.

We first examined DesLO expression profiles for select hepatic specific genes via qRT-PCR. We observed significant upregulation of liver genes CYP3A4, HNF4A, Albumin, ASGPR1, and FXR (NR1H4) in DesLO (FIG. 6A, 6B). CYP3A4 activation in DesLO yielded transcript levels higher than FeLO alone (FIG. 4C) or FeLO with CYP3A4-only CRISPR-based activation (FIG. 4D). This is intriguing as ATF5 and PROX1 alone could minimally affect CYP3A4 levels in FeLO. This effect was also observed at the functional protein level, with CYP3A4 enzymatic activity significantly amplified when CYP3A4 activation was performed in tandem with ATF5 and PROX1 expression (FIG. 4D) suggesting genetic and epigenetic engineering work together to ignite CYP3A4 transcriptional output. Various multiplicities of infection (MOI) were tested. MOI refers to the number of vector particles per cell used in a transduction. When MOI in the range of 90-100 were used, we could achieve transcriptional level comparable to human livers and up to 10,000-fold more than fetal livers (data not shown).

Figures 4E, 4F, 4G, 4H, 4I, 4J, 4K:
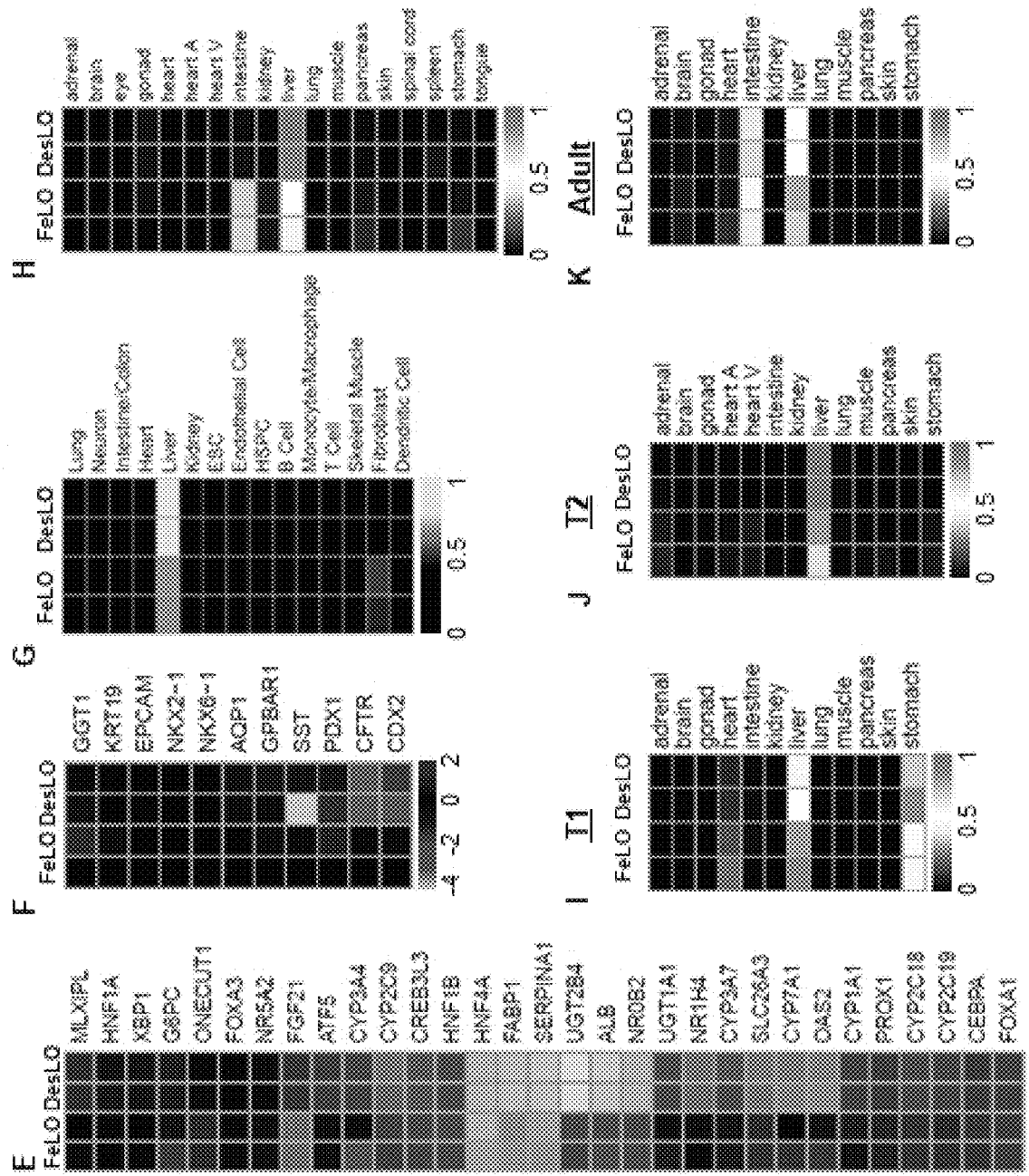

RNA-Seq analyses revealed global increases in hepatic gene expression relative to FeLO, including liver fatty acid binding protein (FABP1; important for metabolic regulation), CYP 2C9 (responsible for metabolizing nonsteroidal anti-inflammatory drugs), phase II metabolic enzyme UDP-glucuronosyltransferases (UGT) 1A1 (for glucuronidation of bilirubin), bile acid nuclear receptor (Farnesoid X Receptor; FXR), and other markers of mature liver function such as albumin (FIGS. 4E, 6A). Furthermore, expression of the other top candidate transcription factors from CellNet (FIG. 4E), cAMP-responsive element-binding protein 3-like protein 3 (CREB3L3) and (MLX Interacting Protein Like) MLXIPL, also rose, reinforcing the desired shift in global GRNs (FIG. 4E). This upregulation occurred in concert with repression of alternate lineage expression such as intestinal marker caudal type homeobox 2 (CDX2) or biliary markers (FIG. 4E).

Genes upregulated from FeLO to DesLO and submitted to EnrichR aligned highest with the RNA-seq and ChIP-seq sample and signature search (ARCHS4) transcriptional libraries for human liver and hepatocytes, while analysis of downregulated genes shared highest identity with off target gastric, renal, and intestinal tissues (FIGS. 6D-6E). EnrichR analysis returned from the WikiPathways library also revealed upregulated hepatic pathways such as the complement and coagulation cascade and FXR signaling pathway, while off-target pathways such as the cardiac progenitor differentiation pathway were downregulated (FIGS. 6D-6E). CellNet analysis performed on the DesLO revealed a significant increase in the liver GRN score, while scores for alternate lineages such as intestine or fibroblast decreased or remained low (FIGS. 4G, 6C).

To cross-validate CellNet findings with an alternative methodology, we used Keygenes, a computational platform developed by Chuva de Sousa Lopes and colleagues. Keygenes collects human fetal transcriptional profiles across different developmental stages and offers a method to quantify the similarity between synthetic cells or tissues and their human fetal counterparts. We thus examined FeLO and DesLO transcriptomic signatures relative to gestational trimesters of human liver development. Using 21 age-combined tissue training sets, Keygenes classified DesLO as liver, demonstrating clear improvement for liver identity and notable removal of intestinal aberrant signatures upon our genetic manipulation (FIG. 4G). We then sought to interrogate changes in liver developmental at trimester one, two, and adult stages following engineering of DesLO, which confirmed improvement of liver identity and maturation at all three-time windows while showing a closest proximity to trimester 2 (FIG. 4I-4K).

Figures 6F, 6G, 6H, 6I, 6J, 6K:
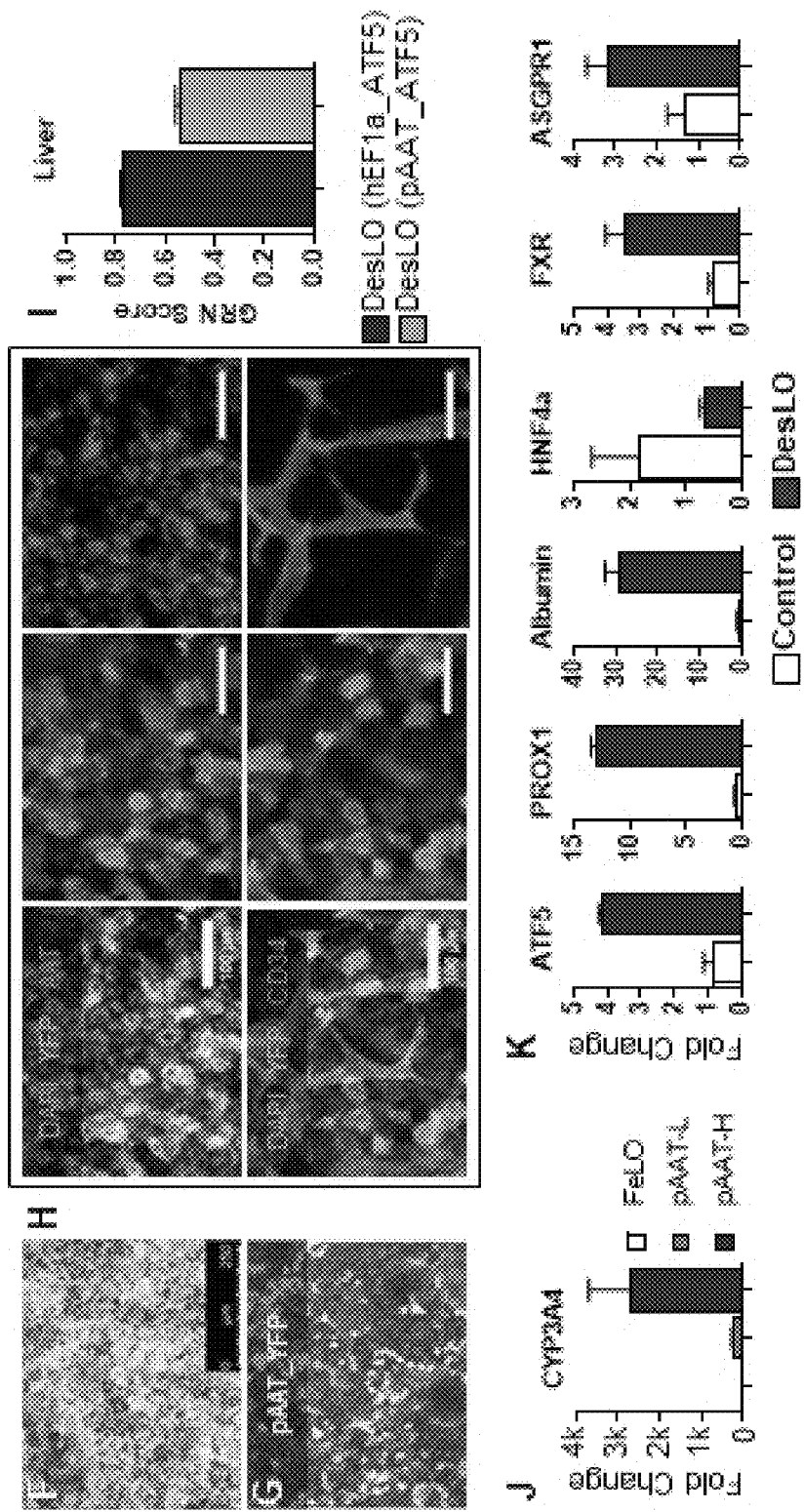

While PROX1 is known important for both hepatocyte and non-hepatocyte (endothelial) cell fate regulation, less data is available regarding the role of ATF5 in nonparenchymal compartments of liver (Meng, 2017). Therefore, we sought to investigate whether confining ATF5 expression to the hepatocyte population can better improve maturation in DesLO. We constructed and validated the human hepatocyte-specific promoter (pAAT) based on AAT expression in native hepatocytes and our FeLO (FIGS. 6F-6H). pATF5 expression vectors showed overlaps with AAT staining in FeLO and exclude vascular CD34 structures. Additionally, pAAT-driven dCas9 showed significant capability for CYP3A4 activation, with higher MOI being more effective (FIG. 6I).

We next compared DesLO generated with hepatocyte confined ATF5 with DesLO that have ATF5 broadly expressed in non-hepatocyte and hepatocyte populations. Broad expression of ATF5 via constitutively active hEFla promoter (hEFla-ATF5) showed higher albumin expression and higher FXR expression when compared to pAAT-ATF5 (FIG. 6K). DesLO CellNet analysis also confirmed these findings. Collectively the data suggest a novel role for ATF5 expression in the non-hepatic population in promoting development of a mature liver GRN. In fact, the limited number of studies so far highlight roles for the ATF family in mesenchymal cells, niche-promoting functions in liver, as well as angiogenesis. For example, ATF4 with pronounced sequence homology to ATF5 induce VEGF and Angptl3 in fetal liver stromal and endothelial cells (Zhao et al., 2015).

Figures 14A, 14B:
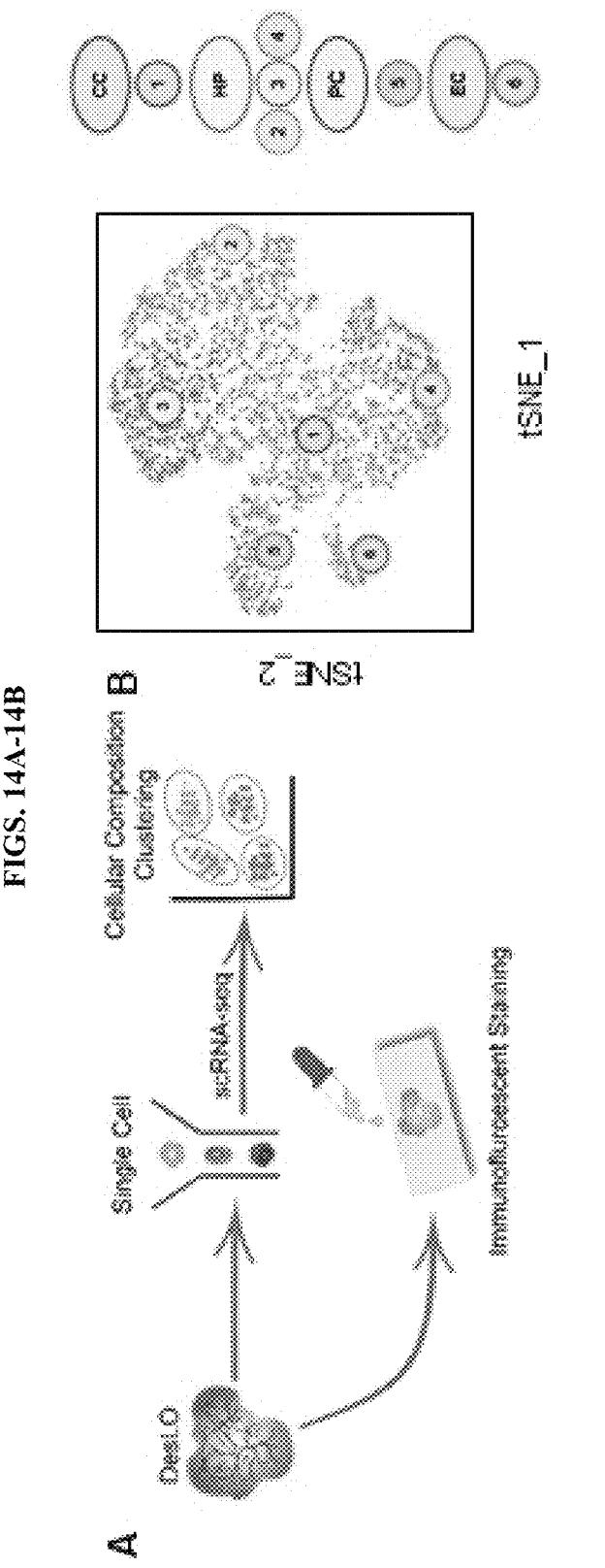
FIGS. 14A-14L. (A) Schematic DesLO single cell analysis pipeline. (B) t-distributed Stochastic Neighbor Embedding plot showing the cell clustering and associated cluster identities. (C) Heatmap showing upregulated genes in each cluster fall. Clusters 2-4 express a significant number of hepatic genes, while clusters 5 and 6 are enriched in stromal cell genes related to endothelial and pericyte identities. (D) Plots showing hepatocyte-specific genes upregulated in hepatocyte-like clusters 2-4, stellate-specific genes upregulated in pericyte cluster 5, and endothelial-specific genes upregulated in endothelial cluster 6. (E) Phase imaging of D12 DesLO cultures shows clear formation of tight junctions, characteristic of hepatic cells in culture. Examples indicated by yellow arrows at cell-cell borders. (F-L) Immunofluorescence staining of Day 17 DesLO cultures showing the associations of hepatocyte like, pericyte-like, and endothelial-like cells through staining of cell-type specific markers.
Figure 14C:
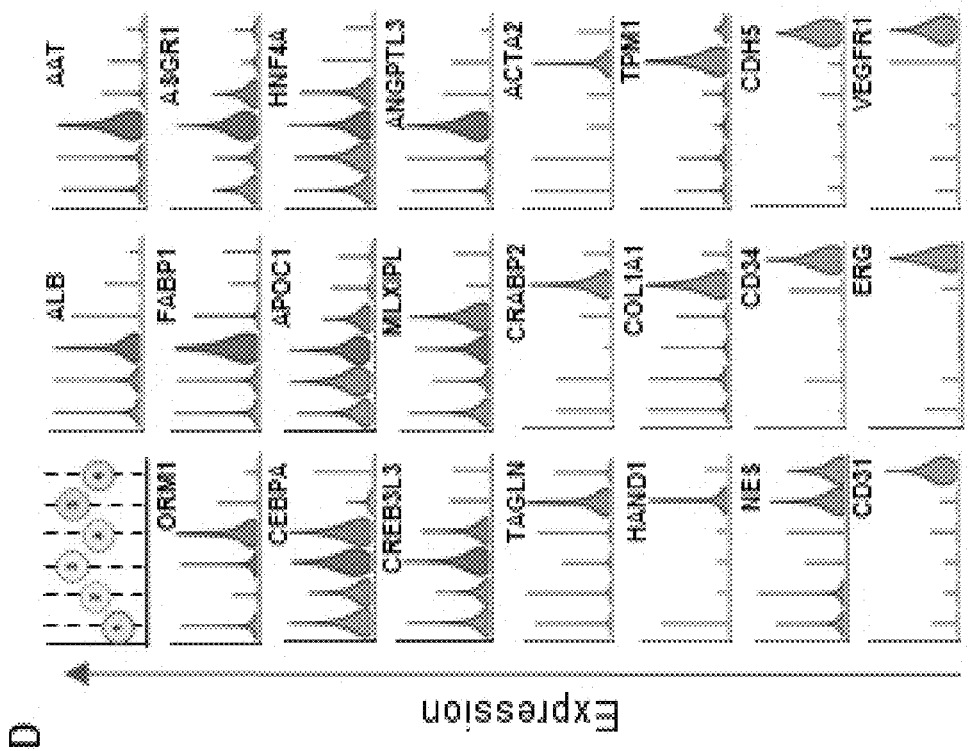

Comprehensive Single Cell Analysis Demonstrates Development of Hepatic-, Endothelial-, and Stellate-like Cell Types Having shown advanced maturation and liver identity in DesLO, we next interrogated development of non-parenchymal cell types such as endothelial or stellate-like cells in DesLO (FIG. 14A). We performed single cell analysis of DesLO at day 11, when there is a dynamic self-organization of heterotypic cell types. This time point also enables rapid and smooth generation of a single cell suspension with minimized collection of aggregates. Using single cell RNA sequencing (scRNA-Seq) we isolated and sequenced mRNA from a total of ~4500 cells with depth of ~120k reads per cell and applied Seurat scRNA-Seq analysis pipeline (Butler et al., 2018) to identify cluster diversity. After filtering of predicted dead cells and doublets, the data revealed 6 distinct clusters visualized by a T-distributed stochastic neighbor embedding (tSNE) dot plot (FIG. 14B). We identified well known hepatic and stromal genes significantly and uniquely upregulated in each cluster or redundantly across the same clusters with the exception of cluster 1 (FIGS. 14C-14D, 15A), which showed no genes distinctly upregulated greater than 1.6-fold above the average gene expression across the other clusters (FIG. 14C). The most elevated genes in cluster 1, however, did contain several G2M and S phase cell cycle-related genes such as TOP2A, TPX2, CDK1, and MKI67, and Seurat's cell cycle scoring showed the highest proportion of cells in S-phase of the cell cycle in cluster 1 (FIG. 15B). The overrepresentation of cell cycle genes can diminish the ability to detect cell specific gene expression. However regressing cell cycle genes shows cluster 1 contains cell sub-populations with the same identities as cluster 2 to 6 (data not shown).

Figure 14D:
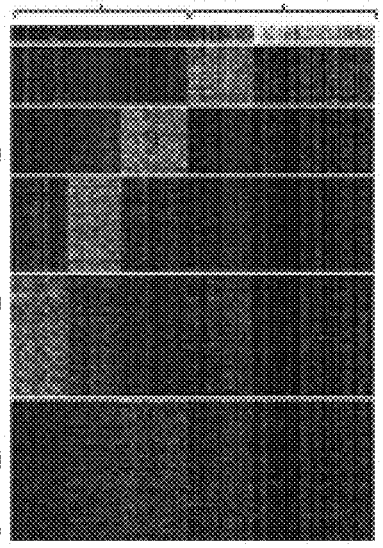
Figure 15E:
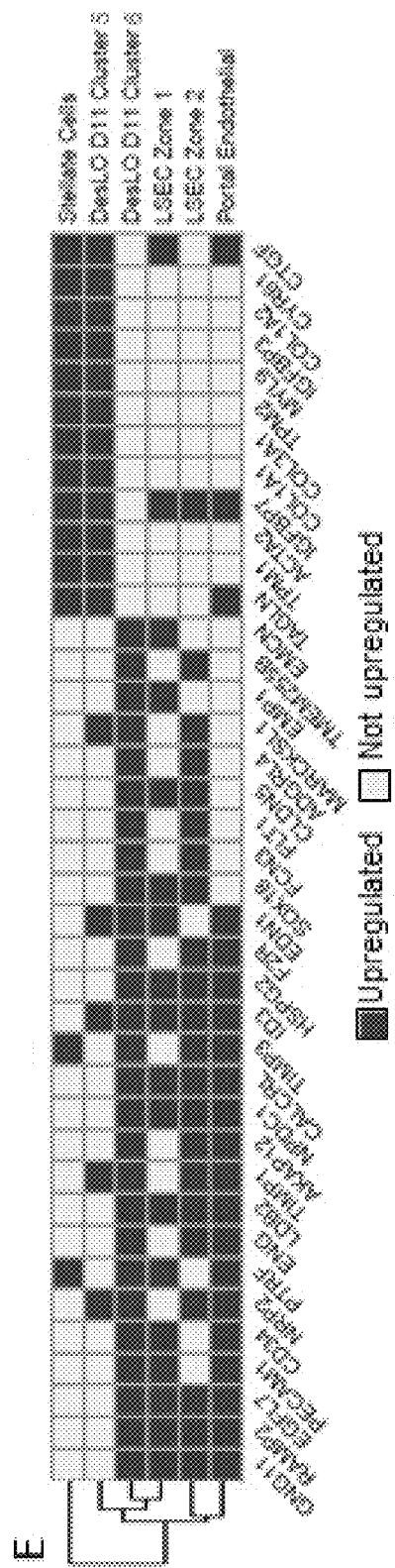

We were able to confirm our original cluster 2-6 assignments with an unbiased method through EnrichR analysis of differentially expressed genes from each cluster and comparison with available single cell data-sets of liver and fetal liver (FIGS. 15C-15E). We identified 3 distinct cell populations in DesLO resembling human liver cell types: hepatocyte, endothelial, and stellate (pericyte)-like cells (FIGS. 14B-14D, 15A, 15C-15D). The endothelial cell (EC) population expressed an array of EC-related genes including VEGFR1 (FLT1), ECSCR, CD34, ERG, and CD31 (PECAM) (FIGS. 14C-14D) which aligned strongly with vasculogenesis and angiogenesis gene ontology processes (FIG. 15D). The DesLO pericyte-like cell (PLC) gene signatures aligned closely with stellate cell markers delineated in a recent single cell report on primary isolated liver samples (FIG. 15E) (MacParland et al., 2018). These cells are highly enriched in genes important in retinoic acid metabolism such as cellular retinoic acid binding protein 2 (CRABP2), structural genes COL3A1, COLIA1, TAGLN (Transgelin), and ACTA2, and another marker of stellate cell identity Desmin (FIGS. 14C-14D, 15A, 15E).

Three clusters (2-4) aligned significantly with either bulk liver or hepatocyte identity by cross referencing cluster enriched gene lists across cell and tissue transcription libraries using EnrichR (FIG. 15C). All three populations express markers denoting general hepatic fate such as CEBPα, HNF4a, APOC1, CREB3L3, and MLXIPL1 (FIGS. 14C-14D, 15A). Cluster 2 showed alignment with hepatocyte and liver gene expression (FIG. 15C) and contains cells with enriched expression of coagulation factors FGA, FGB, FGG (data not shown). Cluster 3 showed the most significant alignment with liver and hepatocyte identity (FIG. 15C), with enrichment of ALB, AAT (SERPINA1), FABP1, ASGR1, and ANGPTL3 (FIG. 14D), markers highly specific to adult liver. We observed the lowest but still pronounced expression alignment with hepatocytes in cluster 4 which showed the highest expression of liver genes ORM1 and ATF5 (FIG. 14D).

Figures 14E, 14F, 14G, 14H, 14I, 14J, 14K, 14L:
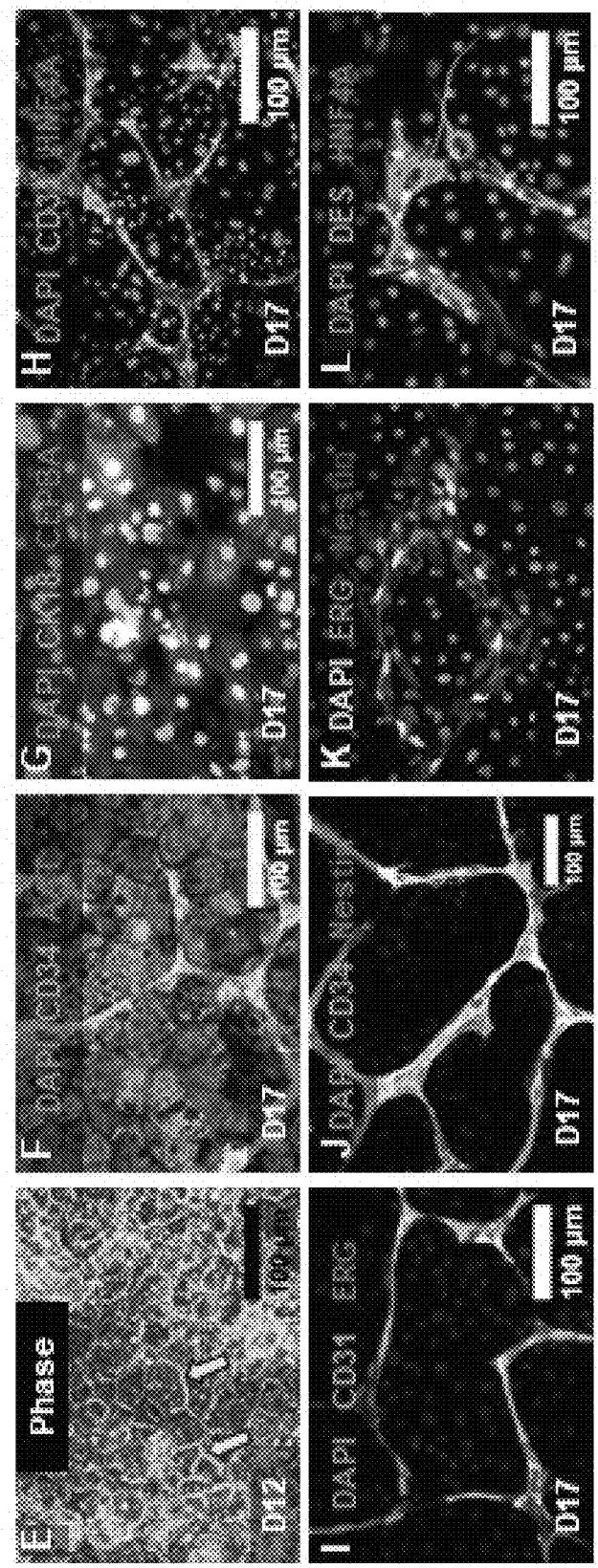
Figures 15F, 15G, 15H, 15I:
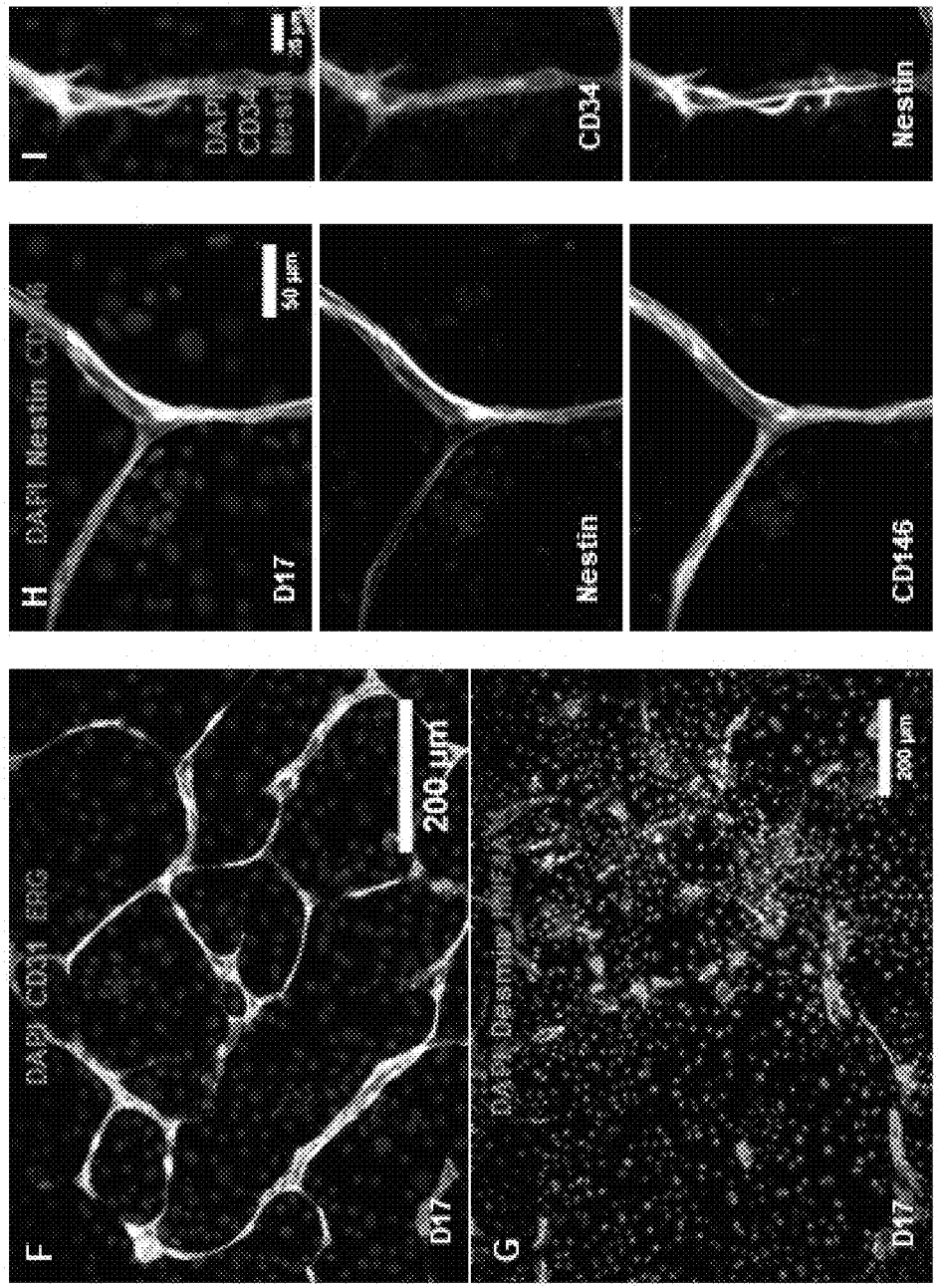

Finally, immunofluorescence staining of select markers on day 17 DesLO confirmed hepatic, stellate, and endothelial compartments that are self-organized in the form of hepatovascular units (FIGS. 14F-14L, 15F-15I). Our tissue analyses show hepatic cells organized in packed polygonal formation with visible tight junctions and vascular lumen (FIG. 14F). The cells express hepatic markers CK18, CEPBPA, and HNF4A (FIGS. 14G, 14H, 14L). Endothelial and stellate cells form a vascular network with stromal markers Desmin, Nestin, and CD146 (melanoma cell adhesion molecule; MCAM) alongside endothelial markers CD34, CD31, and ERG (FIGS. 14H, 14I, 14J, 14K, 14L, 15F-15I). Both the stellate and endothelial populations stain positive for CD146 and Nestin, as indicated in the literature and corroborated by our scRNA-Seq analysis (FIGS. 15H-15I).

Figures 16A, 16B, 16C, 16D, 16E:
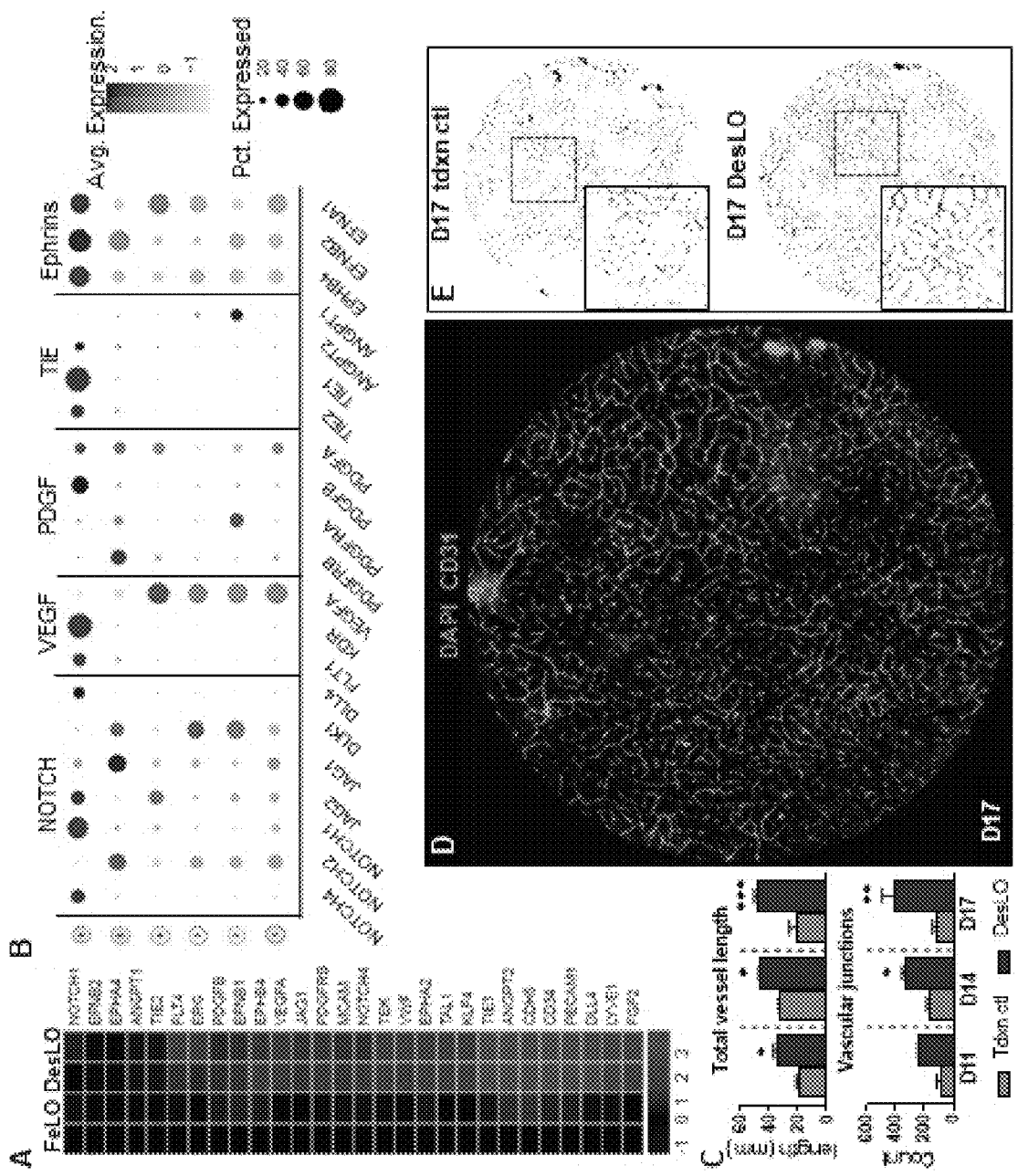
FIGS. 16A-16J. (A) Heatmap showing the upregulation of vasculature-related genes in DesLO over FeLO (n=2). (B) Dot plot showing average expression of receptor (red) and ligand (blue) pairs and percent expressed in D11 DesLO clusters 1-6 from the RNAseq data denotes intercellular signaling among distinct cell types. (C) Angiotool analysis of total vessel length and vascular junctions based on CD31 immunofluorescence staining of DesLO over transduction control FeLO. Significance relative to transduction control FeLO for each time point. *p<0.05; p<0.01; *p<0.001. (D) Immunofluorescence staining of Day 17 DesLO for CD31 showing extensive vascular network. (E) Binary image of immunofluorescence staining of Day 17 transduction control FeLO and DesLO for CD31 used for AngioTool analysis shows visual increase in vascular networks in DesLO. (F) Schematic of tissue preparation and transplantation into mouse. (G) Fibrin adhered DesLO tissue adhered to mesentery. (H) Harvested tissue after >4 weeks transplanted shows tissue growth and vascularization. (I) ELISA for human AAT and Albumin in serum shows detection of human AAT and Albumin between 40-50 days post transplantation of DesLO at mesentery site (n=5). (J) Kaplan Meier survival curve of FRGN mice with and without DesLO sub-renal transplantations. Kidney n=9 (7 beads, 2 mgel plug), Sham n=1. Asterisk denotes log-rank p-value.
Figures 16F, 16G, 16H, 16I, 16J:
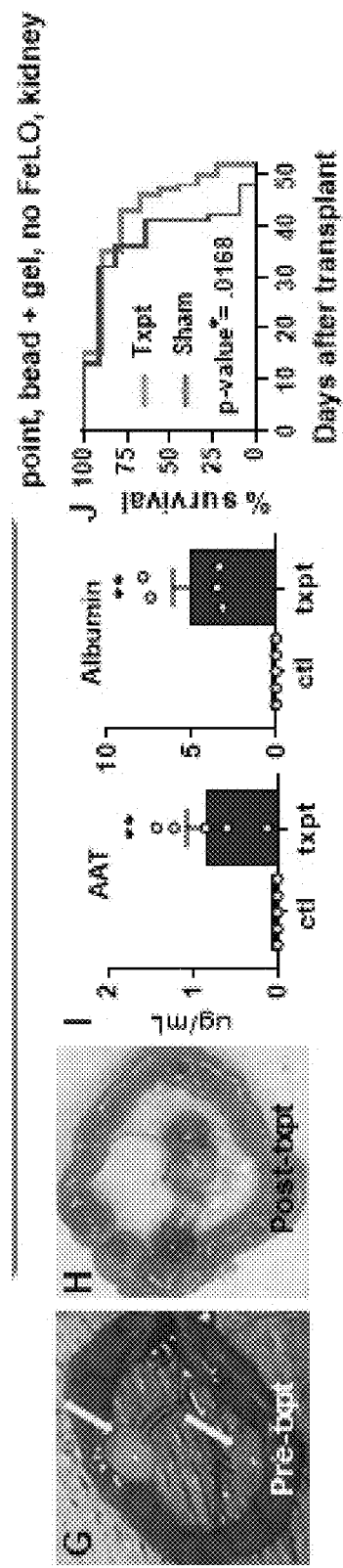
Figures 17A, 17B, 17C, 17D, 17E, 17F:
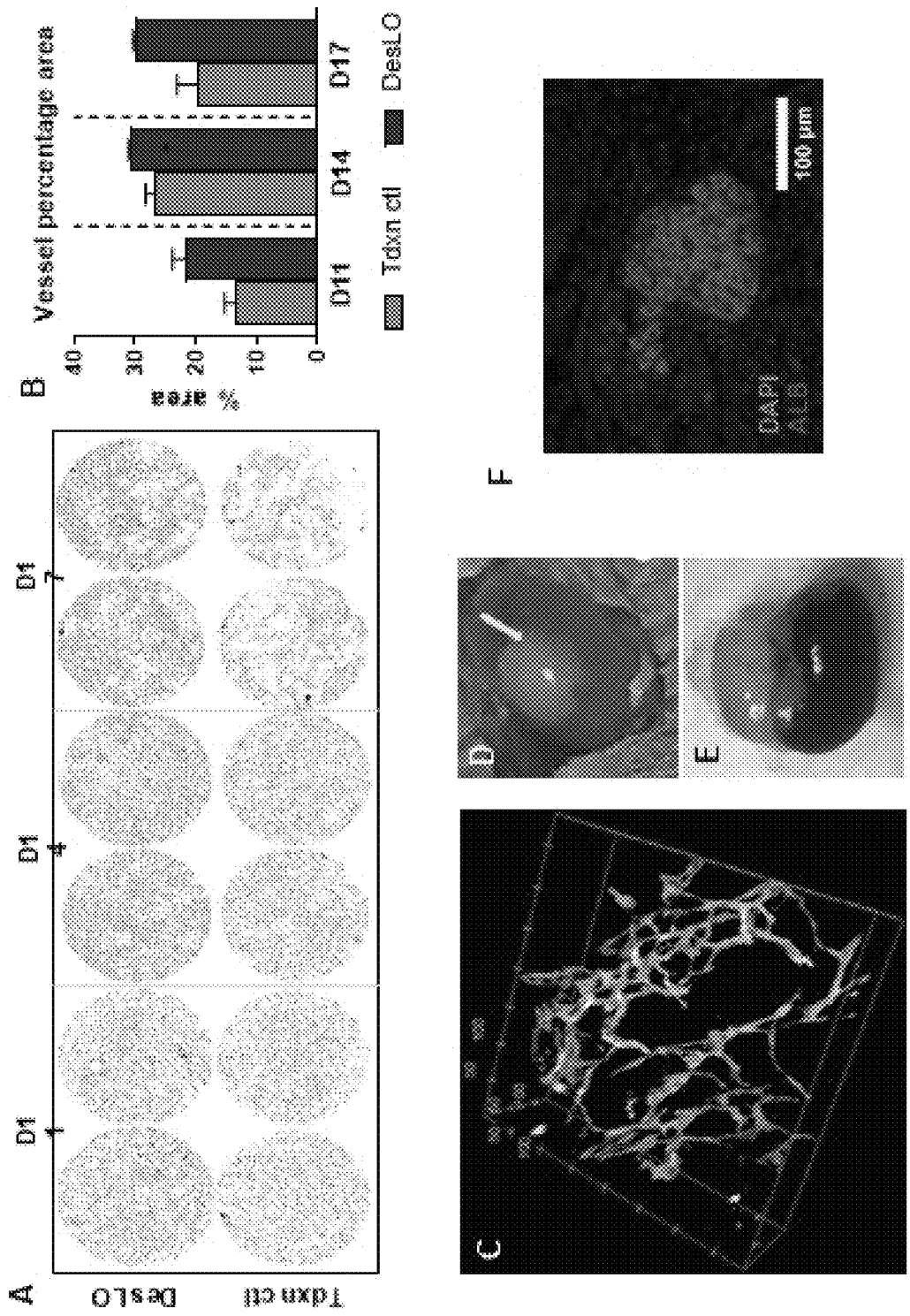
FIGS. 17A-17I. (A) Angiotool interpretation of vasculature from CD31 immunofluorescence staining of Day 11, Day 14, and Day 17 transduction control FeLO and DesLO highlights increased vascular network stability in DesLO. (B) Angiotool analysis of vessel percentage area based on CD31 immunofluorescence staining of DesLO over transduction control FeLO. Significance relative to transduction control FeLO for each time point. *p<0.05. (C) 3D rendering of CD31 stained vasculature of gel plug generated D17 DesLO tissue. (D) Fibrin secured DesLO tissue growth on Matrigel plug inserted beneath renal capsule. Transplant indicated by yellow arrow. (E) DesLO tissue growth and vascularization after 4 weeks of transplantation in FRGN liver injury mouse model. (F) Albumin staining of paraffin embedded tissue section from harvested renal capsule transplant. (G) Integration of human and mouse CD31 shown via immunofluorescence staining of paraffin section. Arrows indicate sites of overlap (Left). (Right) increased zoom of indicated selection denoted in left image by dotted rectangle. Lectin denotes vasculature from both species. (H) Albumin measurements in mouse serum of TK-NOG live injury model between 35-45 days post-transplant (blood taken on day of euthanization from survival study) (n=3). (I) Survival evaluation at day 19 post-GCV treatment completion of TK-NOG mice with and without mesentery site DesLO transplant shows significance by Fisher's exact test.
Figure 17G:
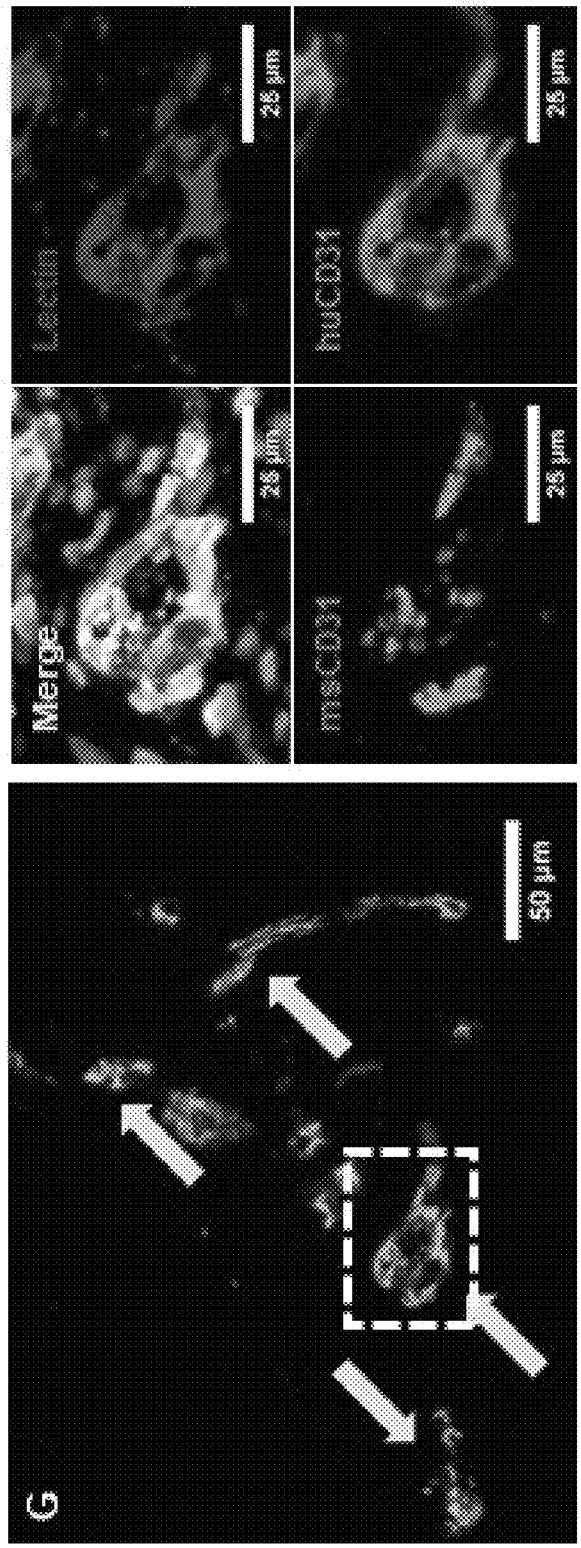
Figure 17H:
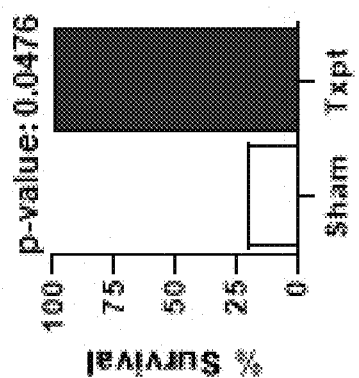
Figure 17I:
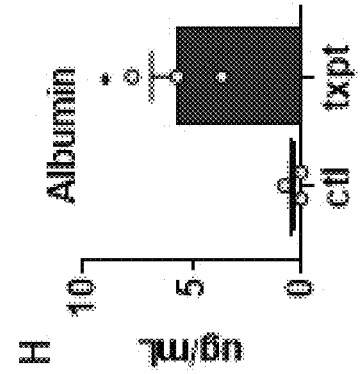

Investigating the function and therapeutic potential of engineered human organoids in vivo Experiments were performed to demonstrate the in vivo functionality of DesLO to produce human liver-specific proteins and support host liver function after injury. DesLO showed capability to maintain 3D integrity of vascular structures, indicating high potential for engraftment (FIG. 17C). Multiple DesLOs were combined using a fast-forming fibrin gel and secured over the mesentery vascular bed or packed beneath the renal capsule (FIGS. 16G, 17D). We took advantage of FRGN mice where liver injury is prevented upon addition of drug 2-(2-nitro-4-trifluoromethylbenzoyl)-1,3-cyclohexanedione (NTBC) to drinking water. The hepatocyte death and liver failure can be induced after removal of NTBC (see methods). Harvested DesLO shows vascularization at the site of implantation (FIGS. 16H, 17E). When we measure human proteins in mouse blood, significant levels of human albumin and AAT were detected in serum after 4 weeks post-implantation (FIG. 16I). Also patches of hepatic cells producing human albumin, were identified from whole mount confocal imaging of the recovered transplant (FIG. 17E). Upon harvest of the transplants, histology revealed human and mouse endothelial cell integration via species-specific markers for CD31, with lectin staining the endothelial cells from both species (FIG. 17G). When we examined survival of mice receiving DesLO following complete removal of NTBC we could observe a modest but significant increase over sham controls (FIG. 16J). To further test applicability of these findings to another model of liver injury, we used a second model of liver injury where mice albumin promoter drives thymidine kinase. Therefore, after Ganciclovir (GCV) challenge, hepatocyte death and liver damage can be triggered. Similarly, in TK-NOG transplants human albumin was detected in the serum. When assessed mice at day 19 after last GCV injection we detected 100% survival in transplanted group as compared with 20% in sham operated (P<0.05 by Fisher's Exact Test). Survival graph supported a trend in improved survival following implantations (FIG. 17I).

DesLO) Exhibits Augmented Vascular Formation: Next, we aimed to examine the vascular self-organization of endothelial cells in DesLO. We assessed angiogenesis-related transcriptional signatures in DesLO and found upregulation of angiogenic growth factors VEGFA, PDGFB, and FGF2, endothelial identity markers ERG, TIE1, PECAM1, VWF, and notably, the liver sinusoidal endothelial cell marker LYVE-1 (FIG. 16A). When we examined the angiogenic signaling cues to cell clusters from day 11, we observe distinct expression of cognate ligands and receptors indicative of the intercellular signaling networks in DesLO (FIG. 16B). Well characterized receptor-ligand paracrine interactions for intercellular signaling pathways involved in angiogenesis were also found between endothelial like-cells and pericyte-like cells and hepatocyte clusters. VEGFA is produced by all 4 hepatocyte clusters and shows receptors on endothelial cluster. Endothelial cluster in return communicates with pericyte cluster via PDGFRβ-PDGFβ signaling. The receptors NOTCH1 and NOTCH4 are highly upregulated in the endothelial cluster, while NOTCH2 is mostly expressed in non-endothelial clusters and specially PLC population. Pericytes express JAG1, and endothelial clusters are enriched for DLL4. In fact, Notch signaling has been shown to be important in vascular morphogenesis and stabilization, and DLL4-Notch signaling in particular has been implicated in vascular formation and angiogenesis.

In order to better assess the phenotypic impact of angiogenic gene signatures in DesLO, we performed quantitative image analysis of vascular networks in CD31-expressing cells on D11, D14, and D17 (FIGS. 16C-16E, 17A-17B). Our analysis revealed that the total vessel length, vessel percentage area, and number of vascular junctions were increased in DesLO relative to control FeLOs (FIG. 16C, 17B). For total vessel length, we observed statistically significant increases at each time point, and by D17, DesLO outperformed all other conditions substantially. Importantly, all vessel metrics have decreasing trends in the control conditions from D14 to D17, indicating instability of the vascular network, whereas the same measurements for DesLO cultures remain stable (FIGS. 16C, 16E, 17A, 17B). Taken together, these data confirm the improvements in vascular development conferred by our genetic engineering, resulting in a self-organized, spontaneously-formed vascular network co-developing from the same starting population of cells as the other hepatic tissue.

DesLO) Tissues Enable Modeling of Bile Acid Synthesis and Regulation via FXR Activation: Activation of Farnesoid X receptor (FXR) signaling in the liver maintains bile acid homeostasis, inhibits NF-KB mediated inflammation, and controls metabolic hemostasis. FXR agonists are being tested in clinical trials for controlling liver inflammation, non-alcoholic fatty liver disease and fibrosis. It has been shown that bile acids generated in the liver can activate the FXR pathway Bile acid binding to FXR results in the secretion of fibroblast growth factor 19 (FGF19), which binds to the FGFR4-beta Klotho complex and repress CYP7A1 metabolism of cholesterol in a small heterodimer partner (SHP, official gene symbol NROB2) dependent manner (FIG. 18B).

Figures 18A, 18B, 18C, 18D, 18E, 18F, 18G:
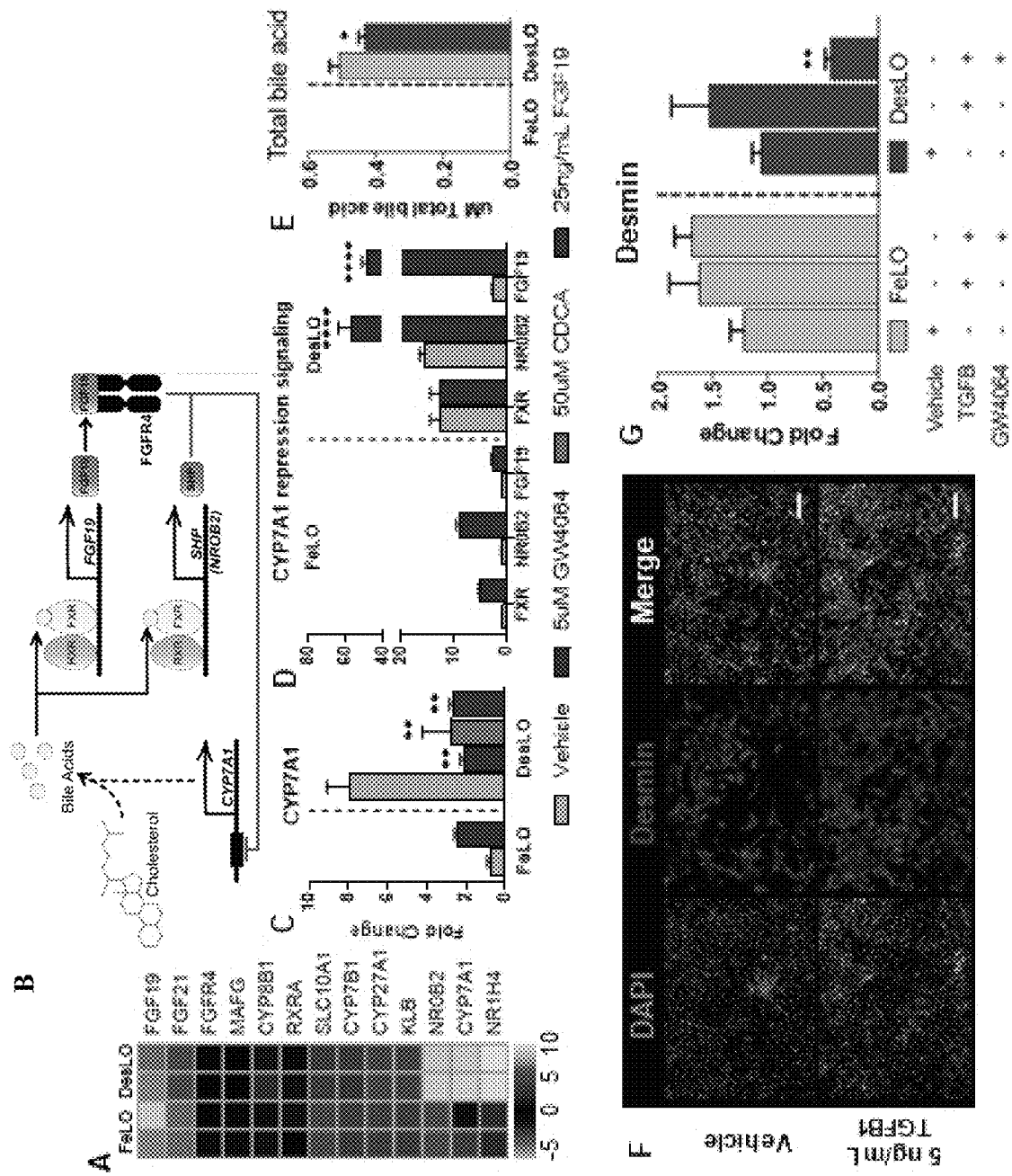
FIGS. 18A-18G. (A) Heatmap of gene expression in FeLO and DesLO from RNA sequencing data highlighting increased DesLO expression of genes involved in FXR signaling (n=2). (B) Schematic of FXR regulation of bile acid synthesis. (C) qRT-PCR for CYP7A1 in FeLO and DesLO with addition of GW4054, CDCA, and FGF19. Significance relative to DesLO vehicle control. p<0.01 (n=3). (D) qRT-PCR for FXR, NROB2, FGF19 in FeLO and DesLO with addition of GW4054. Significance relative to DesLO vehicle control for each target. **p<0.0001. (n=3). (E) Total bile acid secreted in FeLO and DesLO with addition of GW4054. Significance relative to DesLO vehicle control. *p<0.05 one-tail T-test (n=3). (F) Immunofluorescence staining for Desmin in DesLO reveals increase in expression after addition of 5 ng/mL TGFB1 for 3 days. (G) qRT-PCR for Desmin in FeLO and DesLO with addition of TGFB1 and GW4054. Significance relative to DesLO vehicle control. **p<0.01 (n=3).

Key mediators of the bile acid synthesis regulatory pathway are upregulated in our engineered DesLO including CYP7A1, NR1H4 (FXR), and NROB2 (SHP) (FIG. 18A). We therefore investigated whether the activation of this GRN network enhanced the capacity to model the physiological dynamics of the bile acid synthesis pathway. Real-time qPCR measurement of CYP7A1 expression confirmed increased expression of CYP7A1 in DesLO. Upon addition of a potent synthetic FXR agonist, GW4064, CYP7A1 was repressed 4-fold in DesLO, but was not repressed in FeLO cultures (FIG. 18C). DesLO were further tested with addition of the natural bile acid chenodeoxycholic acid (CDCA) and FGF19 to the media, which also resulted in the expected downregulation of CYP7A1 (FIG. 18C).

To further delineate the mechanism of FXR-mediated CYP7A1 repression, we tested FXR, NROB2, and FGF19 expression following GW4064 treatment. We show in DesLO a robust and potent (>40 folds) upregulation of SHP and FGF19 that were sufficient to repress CYP7A1 activity. Such events could not be captured using FeLO cultures, further supporting the advantage of our genetic engineering in shaping up DesLO identity and response to environmental perturbations (FIG. 18D). Finally, an assay of total bile acid in media revealed that, while FeLO were not able to generate detectable amounts of bile acid from cholesterol in the medium, DesLO were capable of both producing bile acid and successfully recapitulating the role of FXR activation in repression of bile acid synthesis with addition of GW4064 (FIG. 18E).

Figures 19A, 19B:
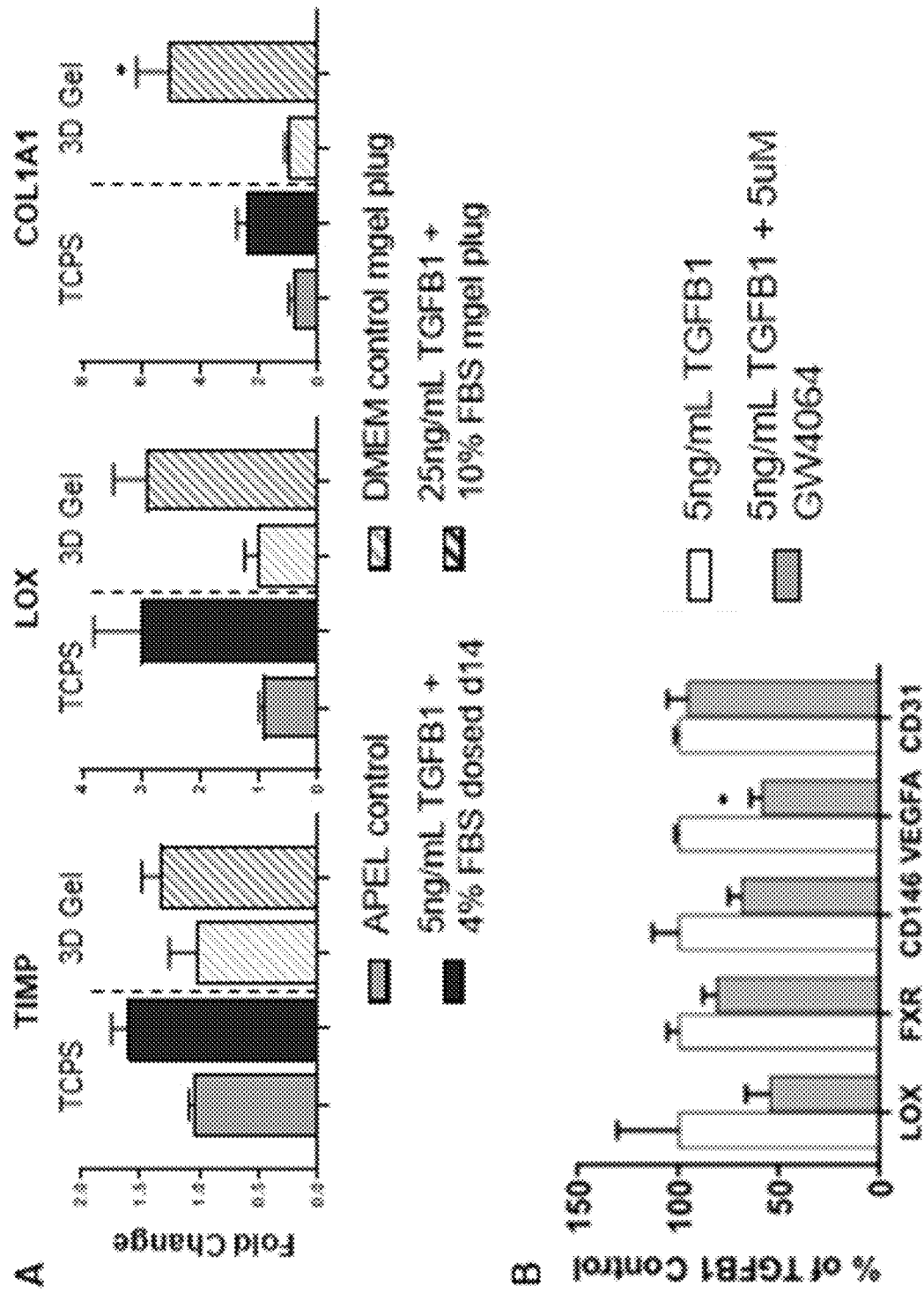
FIGS. 19A-19B. (A) qRT-PCR for TIMP, LOX, and COL1A1 in DesLO from 2D tissue culture polystyrene (TCPS) or 3D matrigel cultures with addition of TGFB1 and FBS. Significance relative to control for each target. *p<0.05 (n=3). (B) qRT-PCR for LOX, FXR, CD146, VEGFA, CD31 in DesLO with addition of TGFB1 and GW4064. Significance relative to TGFB1 condition for each target for each target. *p<0.05 (n=3 for TCPS conditions, n=2 for 3D gel conditions).

Multicellular DesLO as a Model for Fibrogenesis: Hepatic fibrosis is a maladaptive multicellular response of liver that is characterized by an excessive accumulation of extracellular matrix. It is a wound healing process, largely mediated by hepatic stellate cells (liver pericytes) which proliferate, deposit collagen, and generate scar tissue in response to injury. Since DesLOs contain a population of stellate-like cells we assessed whether this cell population respond to classical fibrotic stimuli. We induced fibrogenesis via transforming growth factor beta-1 (TGFβ1) or a combination of TGFβ1 and fetal bovine serum (FBS) supplementation to the culture medium. The Desmin positive population visibly expanded in comparison to the vehicle control (FIG. 18F) and qRT-PCR corroborates the increase in Desmin levels (FIG. 18G). Interestingly while both FeLO and DesLO responded modestly to TGFβ1 treatment, only DesLO could capture antifibrotic effect of FXR agonists (FIG. 18G). It is known that tissue culture treated polystyrene (TCTP) can increase cell stress and stellate cell proliferation. Thus, to improve sensitivity of DesLO to respond to fibrogenic stimulus we tested DesLOs seeded on soft Matrigel plugs. We show increased differential gene expression of TIMP1, LOX, and COL1A1 in DesLO developed in mechanically less stiff cultures (FIG. 19A). Collectively, our data provide potential of DesLO for detecting response to both fibrogenic and anti-fibrotic stimulus.

DISCUSSION

A rigorous quantitative assessment of organoid developmental stage is not frequently practiced in the field, making it difficult to perform side-by-side comparisons of organoids with their in vivo counterparts or organoids generated by an alternative method. This is while a systematic approach that takes into consideration the tissue's GRNs relative to their target organs will be essential for generation of standardized approaches towards understanding and engineering various organoids. Here we show a genetically guided framework that incorporates systematic assessment with rational genetic engineering of multicellular fetal liver organoids towards adult phenotypes.

In context of liver, epithelial-only organoids have been developed through supplementation of exogenous niche-related growth factors. Those studies focused on development of cultures that support long-term expansion and maintenance of hepatocyte and use cells isolated from adult human livers. Therefore, they do not include other liver cell populations from different germ layers such as vascular or stellate cells. Therapeutically functional human liver tissue has been generated in vivo through implantation of fetal liver buds developed through combining iPSC-derived hepatic endoderm cells with human mesenchymal and endothelial cells. While these studies capture self-organization of heterotypic cell types, these organoids can only mature after transplantation in vivo, a widespread issue that typically confound several other PSC-derived organoids too (i.e., kidney, brain or intestine). This notion emphasizes the need for techniques for ex vivo stimulation of tissue development in a rationally designed manner.

Lack of mature phenotypes can be partly explained by cells lacking interactions with co-developing cells and limitations in the time scale of in vitro culture. Reconstituting heterotypic cell-cell interactions can improve maturation, which was evident in liver bud maturation after implantation in vivo. For example, ex vivo, supplementing the flow could also increase co-development of endothelial progenitor cells in kidney organoids, improve vascular formation and improve maturation. The FeLOs generated through our past efforts and in this study employ an isogenic population of hiPSCs and the transcription factor GATA6 to initiate morphogenetic events. It uniquely captures the generation of mesoderm and endoderm tissue from pluripotency, and the subsequent co-differentiation towards a human fetal liver. However, despite its multicellularity, it still lacks adult stage maturity in vitro, suggesting the necessity for additional developmental triggers. We show that genetic engineering provides an effective means to promote maturation in multicellular systems such as FeLO. The presence of multiple cell types in FeLO can synergize with the genetic engineering to initiate a cascade of events, both cell autonomous and non-autonomous, that drive ex vivo organogenesis.

How GATA6, ATF5, and PROX1 together drive vascular morphogenesis of DesLO warrants future investigation. For instance, PROX1 is highly expressed in newly formed liver sinusoidal endothelial cells after revascularization of regenerated hepatocytes and also is an important regulator in the development of lymphoid endothelial vessels. The autonomous autocrine and paracrine signaling cues that drive DesLO vascularization provide a unique microenvironment to interrogate cell-cell communication during vascular morphogenesis in presence of surrounding epithelial tissue.

Engineering cell stage using transcription factors confers spatiotemporal control at the single cell population level and obviates the need for finding common media formulations to support heterotypic cells such as endothelial, pericyte, and hepatocyte-like cells. Additionally, such an approach may serve to accelerate the natural development process, potentially reducing the time in culture and cost necessary to produce a mature tissue. Specifically, here we showed the maturation of hepatic organoids across trimesters of pregnancy in a matter of days. The concept of identifying and steering multicellular systems through a core control module (i.e., a few regulatory nodes) is attractive for developing advanced organoids. In this study, we show that a combination of ATF5, PROX1, CYP3A4 effectively program global liver maturation. We expect there will be other combinations of genetic elements that can be devised with a specific tissue type or application in mind, spearheading a "tissue by genetic design" approach. Additionally, DesLOs can be further engineered through reconstitution of additional cells such as liver immune cells (i.e., Kupffer cells), through use of other technologies such as microfluidics, or through iterative genetic manipulation for additional modifications. Collectively, we demonstrate the potential for synthetic gene circuits to program developmental trajectories in multicellular systems to promote formation and maturity ex vivo, offering a powerful technique to advance organoid technologies.

Materials and Methods

Lentiviral production and titration: HEK293FT cells (Life Technologies) were grown according to the manufacturer's indication in a humidified incubator at 37° C. with 5% $CO_2$. The day before transfection we seeded 8 million HEK293FT cells on a collagen I-coated (Gibco A10483-01) 15 $cm^2$ cell culture dish. On the day of transfection, we replaced the cell culture medium and co-transfected the cells with 15 μg psPAX2 (Addgene Plasmid 12260), 3.75 μg pCMV-VSV-G (Addgene Plasmid 8454) and 11.25 μg of the plasmid to be packaged using 90 ug of linear polyethylenimine (Polysciences, Inc 23966-1). 24 hours post-transfection the medium was changed and 20 ml of fresh cell culture medium added to the cells. 48 hours post-transfection, supernatant was collected and stored at 4° C. A measure of 20 ml of fresh cell culture medium was added to the cells. 24 hours later, supernatant was collected and combined with previous day's stored supernatant, filtered through a 0.45 μm low protein binding filter (Corning) and then further concentrated in an Amicon Ultra 15 filter columns (100 kDa cutoff, Millipore) at 4,000 g to a final volume of ~200 pl. The concentrated virus was then aliquoted, snap frozen, and stored at −80° C. Lentiviral concentrate was titered via qRT-PCR using a commercially available kit (ABM LV900).

Vector Design and Construction sgRNA and SAM Lentiviral Vectors: The MS2-fused transcriptional activator plasmid (Synergistic activation mediator (SAM)) was purchased from Addgene (Addgene plasmid ID: 61423). The MS2-P65-HSF1-GFP was amplified from this vector and sub-cloned into a gateway entry vector for further cloning into a lentiviral gateway destination vector. To generate U6-gRNA-MS2 plasmids, 20 bp guide sequences were inserted into sgRNA-MS2 cloning backbone (Addgene plasmid ID: 61424) at BbsI site via golden gate-based reaction. After screening, U6-sgRNA-MS2 was amplified from this vector and sub-cloned into a gateway entry vector containing U6 sgRNA-MS2 for two target sites total. The U6-sgRNA-MS2 (x2) entry vector and MS2-P65-HSF1-GFP entry vector were cloned into a lentiviral destination vector via gateway cloning.

Transcription Factor and dCas9 Vectors: ATF5 transcript variant 1 cDNA was purchased from Origene (Cat #RC200081) and amplified from this vector and sub-cloned into a gateway entry vector. PROX1 transcript variant 2 cDNA was purchased from GeneCopoeia (Cat #F0925) and amplified from this vector and sub-cloned into a gateway entry vector. The ATF5 entry vector was cloned with entry vectors for either the hEFla or AAT promoter into a lentiviral gateway destination vector via gateway cloning. The PROX1 entry vector was cloned with an entry vector for the hEFla promoter into a lentiviral gateway destination vector via gateway cloning. The dCas9 entry vector was cloned with entry vectors for either the hEFla or AAT promoter into a lentiviral gateway destination vector using gateway cloning.

sgRNA Screening

Single guide RNAs (sgRNA) were designed to target the promoter region of the gene of interest. sgRNAs were screened in HEK293FT cells by transiently transfecting expression vectors for a single sgRNA (50 ng), the synergistic activation mediator (SAM) complex (100 ng), dCas9 (200 ng), and empty vector (150 ng) to bring the total amount of DNA transfected to 500 ng. Cells were harvested after 48 hours and qRT-PCR for the sgRNA target gene was performed. Cells transfected with empty vector in place of the sgRNA were used as reference samples. sgRNAs that yielded the highest level of activation were selected for use and cloned as previously described.

Magnetic Depletion of TRA-1-60 Expressing Cells

TRA-1-60 expressing cells were depleted using Miltenyi MACS separation system after 5 days of dox induction. The day 5 induced cultures were incubated for 12 minutes in accutase (Sigma). Dissociated cells were washed in DMEM/F-12 medium containing 10 µM Y-27632 dihydrochloride (Stem Cell Technologies, Vancouver) and centrifuged at 300 g for 5 minutes. Pellet was resuspended in DMEM/F-12 medium containing 10 µM Y-27632 dihydrochloride and TRA-1-60 antibody conjugated magnetic beads (MACS TRA-1-60 beads, Miltenyi Biotech) and incubated for 5 minutes at 4° C. The suspensions were then flowed through Miltenyi magnetic bead LS separation columns alongside a magnet to trap the positive cell population. The columns were washed with DMEM/F-12 medium containing 10 µM Y-27632 dihydrochloride. All flow through containing the negative cell population was collected, centrifuged at 300 g for 5 minutes, and counted using a hemocytometer.

Lentiviral Transduction

Pre-aliquoted lentiviral concentrate was thawed quickly and maintained on ice before use. hiPSCs were transduced as single-cell suspensions in Matrigel-coated 48-well cell culture plates in mTeSR-1 containing 8 µg/mL polybrene, 10 µM Y-27632, and 1 µg/mL doxycycline. The medium was changed the following day.

Cell Culture

Cells were cultivated under sterile conditions in mTeSR-1 (Stem Cell Technologies, Vancouver) in a humidified incubator at 37° C. and 5% $CO_2$ with medium exchanged daily. Tissue culture plates were coated for 1 h at room temperature with BD ES-qualified Matrigel (BD Biosciences) diluted according to the manufacturer's instructions in ice cold DMEM/F-12 with 15 mM HEPES medium (Stem Cell Technologies, Vancouver). Routine passaging was performed by incubating hiPSC colonies for 5 minutes in Accutase (Stem Cell Technologies, Vancouver) at 37° C., subsequently resuspending this single cell solution in DMEM/F-12 medium containing 10 µM Y-27632 dihydrochloride solubilized in cell culture grade DMSO (Sigma-Aldrich), centrifuging it at 300 g for 5 min and resuspending the pellet in DMEM/F-12 supplemented with Y-27632 at a final concentration of 10 µM for counting. Cells were seeded at a concentration of 32,000 cells per $cm^2$.

HEK293FT were cultured under sterile conditions in a humidified incubator at 37° C. and 5% $CO_2$. Cells were cultured in HEK cell maintenance medium DMEM basal medium supplemented with 2 mM GlutaMAX, 1% penicillin/streptomycin, and 5% fetal bovine serum with the medium being exchanged every 2 days. Cells were passaged every 3-4 days at 85% confluence by using 0.05% Trypsin-EDTA for dissociation and reseeding in HEK cell maintenance medium at a splitting ratio of 1:15.

GATA6 Engineered Cell Line Generation

PGP1 iPSCs were transfected using Lipofectamine 3000 (ThermoFisher Scientific) with PiggyBac transposon vectors encoding rtTA3 and GATA6 under control of the tetracycline responsive element promoter. Transfected cells selected by adding 0.5 µg/mL puromycin to the mTeSR1 maintenance medium over two passages before reverting to regular mTeSR1 medium with no puromycin.

Generation of FeLO and DesLO Tissues

The hiPSCs were seeded at a density of 300,000 cells per $cm^2$ in mTeSR-1 medium supplemented with 10 µM Y-27632. The next day, the medium was changed to mTeSR-1 with 1 µg/mL doxycycline and replaced daily for 5 days. For CRISPR-engineered FeLO and DesLO, day 5 cells were depleted of TRA-1-60 and transduced as described above. The next day, medium was replaced with mTeSR-1 with 1 µg/mL doxycycline. Subsequently the media was switched to APEL 2, a non-pluripotency supporting basal medium (Stem Cell Technologies, Vancouver) and replaced daily. For FeLO differentiation (without TRA-1-60 depletion or lentiviral transduction), medium was changed to APEL 2 on Day 5 and replaced daily. Reseeded FeLO were generated through the same protocol as DesLO but without transduction. Transduction controls were generated through the same protocol as DesLO but were transduced with dCas9 and mKate lentivirus. Tissues were harvested at Day 17 of culture unless otherwise indicated.

For transplantation, cells were seeded on 50% Matrigel plugs (1:1 matrigel and DMEM/F12) instead of Matrigel monolayer coated tissue culture polystyrene to allow contraction of cell layer into a dense tissue.

Tissue Harvest, RNA Extraction, qRT-PCR

Tissues were harvested and lysed by adding 500 µL Trizol (Life Technologies) directly to the tissue culture well and freezing at −80C. For extraction, lysate was thawed on ice, 100 μL chloroform was added, vortexed for 30 seconds, and centrifuged at 12,000 g for 15 minutes at 4° C. After centrifugation the aqueous phase was transferred to a Qiagen gDNA eliminator column and centrifuged at 10,000 g for 1 minute at 4° C. The flow-through was mixed with an equal volume of 70% EtOH and transferred to an RNEasy mini spin column. The manufacturer protocol for the RNEasy Plus Mini Kit (QIAGEN) was followed for the rest of the procedure. cDNA was synthesized using the high Capacity cDNA reverse transcription (Applied Biosystems). qRT-PCR was performed using the SYBR Green intercalating dye (ThermoFisher Scientific) and previously validated primers (IDT). Expression was normalized to 18S ribosomal RNA and relative gene expression was calculated using $2^{-\Delta\Delta CT}$ method.

Immunofluorescent Staining

Cells were grown on Matrigel-coated 8 mm or 12 mm diameter circular glass coverslips and fixed for 20 min in 4% paraformaldehyde (Electron Microscopy Sciences) at room temperature. Coverslips were then washed three times in 200 μl PBS droplets on Parafilm (Pechiney Plastic Packaging Company) followed by 15 min permeabilization in 100 μl of 0.2% Triton X-100 in PBS. Subsequently the coverslips were washed three times in 200 μl in washing buffer (0.05% Tween-20 in PBS) for 5 min and blocked for 20 min in 200 μl wash buffer plus 5% normal donkey serum (Jackson ImmunoResearch Laboratories). The incubation with the primary antibodies was performed for 1 h at room temperature in 30 μl of 5% normal donkey serum in PBS followed by three washes in 200 μl in PBS for 5 min each. The incubation with the secondary antibodies was performed for 1 h at room temperature in 30 μl of 5% normal donkey serum in PBS followed by three washes in 200 μl in PBS for 5 min. Finally, the coverslips were mounted on microscopy glass slides using ProLong Diamond Antifade (Life Technologies, USA), cured overnight at room temperature and then sealed with nail polish. Antibody list and concentrations are included in the supplement.

Image Acquisition and Processing

Images were acquired using the Leica DMi8 automated scanning microscope or Leica TCS SP5 confocal microscope, and processed using ImageJ software (NIH). AngioTool software (NIH) was used to quantify the vascular formation metrics. 3D reconstructions were generated using the Leica TCS SP5 confocal microscope to generate z-stacks spanning ~200 μm deep into the tissues, and using Image J to construct a 3D volume from the stacks.

ELISA Assays

Collected media were assayed for AAT (Genway Biotech), fibrinogen (Genway Biotech) and albumin (Bethyl Labs) using commercially available ELISA kits. Advanced DMEM/F12 was used as culture medium for samples used for the albumin ELISA due to the presence of human albumin in APEL 2 medium. Samples dilutions were optimized to attain detection in the linear range of the associated standard curve.

CYP3A4 Activity Assay

The CYP3A4 activity assay was performed using the luciferin-IPA substrate according to the manufacturer's instructions for Cell-based assays. (P450-Glo CYP3A4 Assay, Promega)

Total Bile Acid Assay

The total bile acid assay (Cell Biolabs) was used to measure the bile acid concentrations in FeLO and DesLO cultures. The cell supernatant was assessed at multiple dilutions to optimize detection, and the assay was performed according to the manufacturer's protocol.

LDL Uptake and Oil Red O Assays

Low density lipoprotein uptake (Thermo Fisher) and oil red O (Sigma) assays were performed according to the manufacturer's instructions.

Statistical Testing

For studies in which statistical analyses were performed, at least three biologically independent replicates were used. Statistical comparisons of three or more conditions were performed using one-way ANOVA and multiple comparisons testing on means using Tukey's method with a p-value <0.05 as the threshold for significance. For comparisons between two conditions, two tailed t-tests were performed with a p-value <0.05 as the threshold for significance.

Transplantation

DesLO tissues were collected from gel plug culturing technique, transplanted either beneath the renal capsule or on the mesentery, and secured in place using a fibrin gel supplemented with 50 ng/mL hHGF and 20 ng/mL h VEGF-165 to promote survival and angiogenesis of the tissue for integration with host vasculature. For survival studies, TK-NOG (Taconic) and FRGN (Yecuris) mice between 8 and 12 weeks old were transplanted. For the TK-NOG survival studies, ganciclovir (50 mg/kg, IP), which is innocuous to normal human and mouse cells, was administered to induce damage of the mouse transgenic liver parenchymal cells at day 7, 10, and 20 after transplantation of 12 DesLO tissues onto the mesentery. For FRGN survival studies, nitisinone (NTBC) was removed from the drinking water directly after transplantation of 4 DesLOs under the renal capsule, or 12 DesLO tissues onto the mesentery. The NTBC treatment was cycled once, being added to the drinking water at 16 mg/L after 14 days for 5 days, and then removed permanently. For control experiments, Sham surgeries were performed identical to the transplantations but with no transplanted tissues. As additional controls, FRGN mice transplanted with FeLO tissues depleted of TRA-1-60 and cultured in the same formate and timeline as DesLO tissues were also assessed. Kaplan-Meier survival analysis was performed with Prism 6 (GraphPad Software Inc.).

The mice were bred (FRGN only, TK-NOGs from Taconic cannot be bred), housed, fed, and monitored in accordance with the protocols approved by the Institutional Animal Care and Use Committee at Arizona State University and all animals were carefully monitored for signs of morbidity and discomfort by research and veterinary staff.

RNA Sequencing of FeLO and DesLO Time-Course Tissues

RNA was extracted from samples using TRIzol (Invitrogen) as described above and sent to the UCLA Technology Center for Genomics and Bioinformatics for library preparation and sequencing.

Libraries for RNA-Seq were prepared with KAPA Hyper Stranded RNA-Seq Kit. The workflow consists of mRNA enrichment, cDNA generation, and end repair to generate blunt ends, A-tailing, adaptor ligation and PCR amplification. Different adaptors were used for multiplexing samples in one lane. Sequencing was performed on Illumina NextSeq500 for a single read 75 bp run. Data quality check was done on Illumina SAV. Demultiplexing was performed with Illumina Bcl2fastq2 v 2.17 program.

A raw FASTQ quality check was performed using FASTQC[1]. Reads were then mapped to the latest UCSC transcript set using Bowtie2 version 2.1.0[2] and the gene expression level was estimated using RSEM v1.2.15[3]. EdgeR's[4] TMM (trimmed mean of M-values) algorithm was used to normalize the gene expression data. Reads were then mapped to the latest UCSC genome set using Bowtie2 and Tophat[5]. The resulting BAM file allowed for collection of information on the alignment via PicardTools[6] CollectRNASeqMetrics program. A Genebody analysis was performed using the ngsplot[7] toolkit.

EnrichR Analysis

Differential expression data was generated from the TMM normalized gene counts by dividing the average counts of each sample (FeLO D5, FeLO D10, FeLO D17, DesLO D17, DesLO D17 pAAT-ATF5) over the average counts for the non-induced hiPSC condition (DO) for each gene. The resulting fold change list was used to generate a list of genes for each condition with at least four reads and ≥2 fold change over the non-induced condition. The genes from each resulting list were imported into the EnrichR web browser application, and the results used to generate alignment scoring and significance data for cell, pathway, function, and ontology analyses.

For scRNAseq data. Geene liests were generated from Seruat generated lists for each cluster including genes with adj. p-values <0.05 and fold change expression of at least 1.6-fold over the average gene expression of the other clusters. The lists were then submitted to EnrichR.

10x Genomics Sample Preparation for Next-Generation Sequencing

Samples were prepared as described by the 10x Genomics Single Cell 3' v2 Reagent Kit user guide. Day 11 DesLO were in acquired in single cell suspension by incubation with Accutase for 10 minutes at 37C, followed by gentile pipetting using a serological pipette to dislodge and dissociate aggregates. Two washes in PBS −/−+0.04% BSA were performed with the cells resuspended at a final concentration of 1000 cells/uL in PBS −/−+0.04% BSA. A live cell count was performed with a hemocytometer using Trypan Blue to identify dead cells. Following counting, cells and 10x Genomics reagents were loaded into the single cell-A cassette, with a target of 6000 single cells for analysis, accounting for cell loss and doublets as laid out in the user guide for the Chromium Single-Cell 3' Reagent Kit (10x Genomics). After generation of GEMs, the cDNA library was prepared by ASU Genomics Core staff following the appropriate steps determined by the 10x Genomics user guide. Libraries were sent to Novogene and for sequencing by an Illumina HiSeq X for an intended read depth of 100,000 reads per cell (assuming 6000 cells) with 150 bp paired end reads. The sequencing data was returned in FASTQ format. The 10x Genomics Cell Ranger pipeline according to 10x genomics recommendations was used to process and map the samples, and generate the matrix and tsv files for downstream analysis using the Seurat R-package[9].

Single cell data was excluded based on high mitochondrial genome transcript ratio (>0.1 for our D11 DesLO sample) and small library size (<2000). Genes with UMI counts in fewer than 5 cells were removed from consideration.

scRNAseq Data Processing and Cluster Analysis Using Seurat

We used the following general standardized pipeline for processing the Cell Ranger output: Normalization, scaling, detection of variable genes, principal component analysis (PCA), and clustering. This assigned each cell to a cluster, and reported the fold change expression and percent expressing cells in each cluster compared to the average of all other clusters. Visualization was achieved by the used of tSNE plots identifying cells, clusters, and selected gene expression in each cell, as well as heatmaps and violin plots showing the expression level of genes by cluster.

We claim:

1. A method for producing a synthetic mature liver organoid, the method comprising the steps of
    introducing into cells of a fetal liver organoid one or more lentiviral constructs comprising an inducible transgene encoding at least one transcription factor selected from ATF5, Prox1, MLXIPL1, and CREB3L3, wherein, prior to introducing the one or more lentiviral constructs, the fetal liver organoid comprises a cell population comprising at least 70% CXCR4+ cells;
    inducing expression of the inducible transgene by contacting the fetal liver organoid to a small-molecule inducer of transgene expression;
    transducing cells of the fetal liver organoid with one or more CRISPR cassettes comprising a nucleic acid sequence encoding dCas9 and one or more gRNAs that bind to a target site in a human CYP3A4 locus, wherein the one or more gRNAs are selected from SEQ ID NO: 2 and SEQ ID NO: 3; and
    culturing the fetal liver organoid, thereby producing the synthetic mature liver organoid comprising albumin+/FGF21+/G6PC+/FXR+ hepatocytes and exhibiting CYP3A4 protein metabolizing activity, hepatic bile acid receptor FXR activity, and bile acid production.

2. The method of claim 1, wherein the small-molecule inducer of transgene expression is doxycycline.

3. The method of claim 1, wherein the one or more gRNAs is under control of a constitutively active phEF1a promoter.

4. The method of claim 1, wherein the one or more gRNAs is under control of a pAAT promoter.

5. The method of claim 1, further comprising culturing the fetal liver organoid for about 5 days after introducing the one or more lentiviral constructs into the cells and before transducing the cells with the one or more CRISPR cassettes.

6. The method of claim 1, wherein the steps of introducing into the cells one or more lentiviral constructs and transducing the cells with the one or more CRISPR cassettes are done in tandem.

7. The method of claim 1, wherein the method further comprises contacting exogenous TGFb protein to the mature liver organoid, whereby fibrogenesis and expression of Desmin increases in the contacted organoid relative to an uncontacted control.

8. The method of claim 1, wherein prior to introducing into cells of the fetal liver organoid one or more lentiviral constructs, the fetal liver organoid is obtained according to the following steps:

(a) introducing into human pluripotent stem cells (hPSCs) one or more lentiviral constructs comprising an inducible transgene encoding GATA-binding protein 6 (GATA6);
(b) inducing expression of the GATA6 transgene in the hPSCs; and
(c) culturing the induced human pluripotent stem cells (hiPSCs) in the presence of a pluripotency supporting medium for about 5 days, whereby a cell population comprising at least 70% CXCR4+ cells is obtained.

9. The method of claim 8, wherein the hPSCs are cultured in a chemically defined medium comprising a Rho Kinase (ROCK) inhibitor prior to step (a).

10. The method of claim 9, wherein the ROCK inhibitor is Y-27632.

11. The method of claim 8, wherein the human pluripotent stem cells are human embryonic stem cells or human induced pluripotent stem cells.

12. The method of claim 8, further comprising the step of (d) culturing the cell population of step (c) in a basal cell culture medium for about 10 days, whereby a cell population comprising CD34+/CD93+ endothelial-like cells, CD51+/NES+/PDGFRα+ mesenchymal stem cell-like cells, DES+ stellate-like cells, and CEBPα+ hepatocyte-like cells is obtained.

13. A synthetic mature liver organoid obtained according to the method of claim 1.

14. The method of claim 1, wherein the steps of introducing into the cells one or more lentiviral constructs and transducing the cells with the one or more CRISPR cassettes are done sequentially.

15. The method of claim 1, wherein the step of culturing the fetal liver organoids comprises culturing for at least 5 days.

* * * * *

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Tyr Ile Gly Ser Arg
1               5

<210> SEQ ID NO 2
<211> LENGTH: 20
<212> TYPE: DNA
<213> ORGANISM: Artificial Sequence
<220> FEATURE:
<223> OTHER INFORMATION: synthetic CYP3A4 g3 gRNA

<400> SEQUENCE: 2
actcaaagga ggtcagtgag                                           20

<210> SEQ ID NO 3
<211> LENGTH: 20
<212> TYPE: DNA
<213> ORGANISM: Artificial Sequence
<220> FEATURE:
<223> OTHER INFORMATION: synthetic CYP3A4 g4 gRNA

<400> SEQUENCE: 3
```

<210> SEQ ID NO 4
<211> LENGTH: 849
<212> TYPE: DNA
<213> ORGANISM: Artificial Sequence
<220> FEATURE:
<223> OTHER INFORMATION: synthetic ATF5 CDS seqeunce

<400> SEQUENCE: 4

```
atgtcactcc tggcgaccct ggggctggag ctggacaggg ccctgctccc agctagtggg      60
ctgggatggc tcgtagacta tgggaaactc cccccggccc ctgccccct ggctccctat      120
gaggtccttg ggggagccct ggagggcggg cttccagtgg ggggagagcc cctggcaggt     180
gatggcttct ctgactggat gactgagcga gttgatttca cagctctcct ccctctggag     240
cctcccctac cccccggcac cctcccccaa ccttccccaa ccccacctga cctggaagct     300
atggcctccc tcctcaagaa ggagctggaa cagatggaag acttcttcct agatgccccg     360
ctcctcccac accctcccc gccgccacta ccaccaccac cactaccacc agcccccctcc     420
ctcccctgt cctccctc ctttgacctc cccagcccc ctgtcttgga tactctggac        480
ttgctggcca tctactgccg caacgaggcc gggcaggagg aagtggggat gccgcctctg     540
cccccgccac agcagccccc tcctccttct ccacctcaac cttctcgcct ggccccctac     600
ccacatcctg ccaccacccg aggggaccgc aagcaaaaga gagagaccaa gaacaagtcg     660
gcggctctga ggtaccgcca gcggaagcgg cagagggtg aggccctgga gggcgagtgc      720
caggggctgg aggcacggaa tcgcgagctg aaggaacggg cagagtccgt ggagcgcgag     780
atccagtacg tcaaggacct gctcatcgag gtttacaagg cccggagcca gaggacccgt     840
agctgctag                                                            849
```

<210> SEQ ID NO 5
<211> LENGTH: 2214
<212> TYPE: DNA
<213> ORGANISM: Artificial Sequence
<220> FEATURE:
<223> OTHER INFORMATION: synthetic

<400> SEQUENCE: 5

```
atgcctgacc atgacagcac agccctctta agccggcaaa ccaagaggag aagagttgac      60
attggagtga aaaggacggt agggacagca tctgcatttt ttgctaaggc aagagcaacg     120
tttttttagtg ccatgaatcc ccaaggttct gagcaggatg ttgagtattc agtggtgcag    180
catgcagatg gggaaaagtc aaatgtactc cgcaagctgc tgaagagggc gaactcgtat    240
gaagatgcca tgatgccttt tccaggagca accataattt cccagctgtt gaaaaataac    300
atgaacaaaa atggtggcac ggagcccagt ttccaagcca gcggtctctc tagtacaggc    360
tccgaagtac atcaggagga tatatgcagc aactcttcaa gagacagccc ccagagtgt    420
ctttcccctt ttggcaggcc tactatgagc cagtttgata tggatcgctt atgtgatgag   480
cacctgagag caaagcgcgc ccgggttgag aatataattc ggggtatgag ccattccccc   540
agtgtggcat aaggggcaa tgaaaatgaa agagagatgc cccgcagtc tgtgagtccc     600
cgagaaagtt acagagaaaa caaacgcaag caaaagcttc cccagcagca gcaacagagt    660
ttccagcagc tggtttcagc ccgaaaagaa cagaagcgag aggagcgccg acagctgaaa    720
cagcagctgg aggacatgca gaaacagctg cgccagctgc aggaaaagtt ctaccaaatc    780
```

-continued

```
tatgacagca ctgattcgga aaatgatgaa gatggtaacc tgtctgaaga cagcatgcgc    840
tcggagatcc tggatgccag ggcccaggac tctgtcggaa ggtcagataa tgagatgtgc    900
gagctagacc caggacagtt tattgaccga gctcgagccc tgatcagaga gcaggaaatg    960
gctgaaaaca agccgaagcg agaaggcaac aacaaagaaa gagaccatgg gccaaactcc   1020
ttacaaccgg aaggcaaaca tttggctgag accttgaaac aggaactgaa cactgccatg   1080
tcgcaagttg tggacactgt ggtcaaagtc ttttcggcca agccctcccg ccaggttcct   1140
caggtcttcc cacctctcca gatccccag gccagatttg cagtcaatgg ggaaaaccac    1200
aatttccaca ccgccaacca gcgcctgcag tgctttggcg acgtcatcat tccgaacccc   1260
ctggacacct ttggcaatgt gcagatggcc agttccactg accagacaga agcactgccc   1320
ctggttgtcc gcaaaaactc ctctgaccag tctgcctccg gccctgccgc tggcggccac   1380
caccagcccc tgcaccagtc gcctctctct gccaccacgg gcttccacca gtccaccttc   1440
cgccacccct tccccttcc cttgatggcc tatccatttc agagcccatt aggtgctccc    1500
tccggctcct tctctggaaa agacagagcc tctcctgaat ccttagactt aactagggat   1560
accacgagtc tgaggaccaa gatgtcatct caccacctga gccaccaccc ttgttcacca   1620 gcacaccgc ccagcaccgc cgaagggctc tccttgtcgc tcataaagtc cgagtgcggc    1680
gatcttcaag atatgtctga aatatcacct tattcgggaa gtgcaatgca ggaaggattg   1740
tcacccaatc acttgaaaaa agcaaagctc atgttttttt atacccgtta tcccagctcc   1800
aatatgctga agacctactt ctccgacgta aagttcaaca gatgcattac ctctcagctc   1860
atcaagtggt ttagcaattt ccgtgagttt tactacattc agatggagaa gtacgcacgt   1920
caagccatca acgatggggt caccagtact gaagagctgt ctataaccag agactgtgag   1980
ctgtacaggc tctgaacat gcactacaat aaagcaaatg actttgaggt tccagagaga    2040
ttcctggaag ttgctcagat cacattacgg gagttttca atgccattat cgcaggcaaa    2100
gatgttgatc cttcctggaa gaaggccata tacaaggtca tctgcaagct ggatagtgaa   2160
gtccctgaga ttttcaaatc cccgaactgc ctacaagagc tgcttcatga gtag          2214
```